US007351819B2

(12) United States Patent
Kageyama et al.

(10) Patent No.: US 7,351,819 B2
(45) Date of Patent: Apr. 1, 2008

(54) METHOD OF DETECTING NORWALK-LIKE VIRUS (GII)

(75) Inventors: Tsutomu Kageyama, Saitama (JP); Shigeyuki Kojima, Saitama (JP); Shuetsu Fukushi, Saitama (JP); Fuminori Hoshino, Saitama (JP); Kazuhiko Katayama, Saitama (JP)

(73) Assignee: BML, Inc., Tokyo (JP)

( * ) Notice: Subject to any disclaimer, the term of this patent is extended or adjusted under 35 U.S.C. 154(b) by 200 days.

(21) Appl. No.: 10/381,813

(22) PCT Filed: Mar. 28, 2001

(86) PCT No.: PCT/JP01/02542

§ 371 (c)(1), (2), (4) Date: Oct. 24, 2003

(87) PCT Pub. No.: WO02/29120

PCT Pub. Date: Apr. 11, 2002

(65) Prior Publication Data

US 2004/0072145 A1 Apr. 15, 2004

(30) Foreign Application Priority Data

Sep. 29, 2000 (JP) ............................ 2000-300724

(51) Int. Cl.
*C07H 21/04* (2006.01)
*C12P 19/34* (2006.01)

(52) U.S. Cl. .................. 536/24.3; 536/24.32; 435/91.2

(58) Field of Classification Search .................... 435/5, 435/6; 536/24.33; 436/504
See application file for complete search history.

(56) References Cited

U.S. PATENT DOCUMENTS 6,380,370 B1 * 4/2002 Doucette-Stamm et al. ......................... 536/23.1
6,699,703 B1 * 3/2004 Doucette-Stamm et al. ....................... 435/252.3
6,783,961 B1 * 8/2004 Edwards et al. ........... 435/91.1
6,812,339 B1 * 11/2004 Venter et al. ............ 536/24.31
7,026,454 B1 * 4/2006 Shah ....................... 530/387.1

OTHER PUBLICATIONS

Wang et al. (J. Virol. 1994, vol. 68, No. 9, pp. 5982-5990.*
Kobayashi et al. J. Clin. Microbil. 2000, vol. 38, No. 9, pp. 3492-3494.*
Ando et al. J. Clin. Micro 1997, vol. 35, No. 3, pp. 570-577.*
Neol. et al. J. med. Virol. 1997, vol. 53, pp. 372-383.*
Carninci et al. Proc. Natl. Acad. Sci. USA, 1998, vol. 95, pp. 520-524.*
Wright et al, *J. of Med. Virol.*, 55(4):312-320 (1998).
NCBI printout for Accession No. AF145896, with citation to Seah et al. *J. Virol.* 73(12):10531-10535.

* cited by examiner

*Primary Examiner*—Bruce R. Campell
*Assistant Examiner*—Bao Qun Li
(74) *Attorney, Agent, or Firm*—Sughrue Mion, PLLC

(57) ABSTRACT

A method of detecting a virus in a specimen, whereby a Norwalk-like virus (GII) is detected by using as an index the nucleic acids of a complementary nucleotide sequence corresponding to the 4851- to 5450-positions of the nucleotide sequence of the cDNA of the prototype (standard strain) of the Norwalk-like virus (GII); and a detection kit for performing this method.

12 Claims, 22 Drawing Sheets

Fig. 2A

```
AF145896/Camberwell       4851 CTGAAACAATGATTCCACACTCCCAAAGACCCATACAATTAATGTCCCTA 4900
X86557/Lorsdale                .............A........................C.......TT.G
X81879-2/Melksham              T...GT.......C........T..G..G........GC.T.....A..C
U07611-2/Hawaii                .............A.....T........G........G..G.....T..G
U02030-2/Toronto(TV24)         G......C.....A.....TG.G..G......G.G..GC.C...G.A...
L23830-2/QTH-25/89/J           G......C.....A.....TA.G..G......G.G..GC.C...G.A..G
AF190817-2/Arg320              .............A...........G...........GC.......A..G
X76716-1/Bristol               .............A........................C.......TT.G
U22498-2/MX                    G......C.....A.....TG.G.TG......G.G..GC.C...G.A...
#U1/AB039775                   .............A..........................G.....TT.G
#U3/AB039776                   AC..G.GC...G....C..T..T..GC..G...C...GC.C...G....T
#U4/AB039777                   AC..G.GC...G....C..T..T..GC..G...C...GC.C...G....T
#U16/AB039778                  A.....GC...G.C..C.........C.GG...C....C.C...G....T
#U17/AB039779                  A.....GC...G.C..C.........C.GG...C....C.C...G....T
#U18/AB039781                  G......C.....A.....TG.G..G......G.G..GC.C...G.A...
#U25/AB039780                  T.....GC........C........G...G.A.CC..GC.....G....C
#U201/AB039782                 C......C.....A.....TG.G..G......G.G..GC.C...G.A...
#17                            A............A.T......T..G..G.........C.C...G.....
#19a                           A...G................T...G............C.......AT.G
#19f                           N......C...........N..N..G......N.N..GC.N...N.AN.N
#82                            A...G........A..C.....T..............GC.T...G.A..G
#83                            A...G........A..C.....T..............GC.T...G.A..G
#84a                           A...G....................G..G.........C.......AT.G
#84b                           A...G........A..C.....T..............GC.T...G.A..C
#89                            A...G........A.T......T..G..G..A......C.C.....T...
#105e                          ..................T.....................G.........
#105d                          ..................T.....................G.........
#16
#101
#105a
#105b
#105c
#111b
#18
#19b
#19c
#19d
#19e
#28
#27b
#31
#32
#34
#35
#36
#37a
#37b
#37c
#58b
#62
#63
#66
#68
#80a
#80b
#80c
#80d
#109
#80e
#80f
#85
#88
#9
#49
#93
#98
#99
                               ..**....***.*.**.**..*.*...*..*....**..*.***.*..*.
```

Tsutomu KAGEYAMA, et al
METHOD OF DETECTING NORWALK-LIKE VIRUS (GII)
Q74881
March 31, 2003
Bruce E. Kramer (202) 293-7060
Page 2 of 22

Fig. 2B

```
AF145896/Camberwell      4901 CTGGCAGAGGCCGCACTCCACGGCCCAGCATTCTACAGCAAAATTAGCAA 4050
X86557/Lorsdale               .....C............................................
X81879-2/Melksham             T.A..T..A..A.....G..T.AA...T.............G..C.....
U07611-2/Hawaii               ..A..T..A..T..T..G.....T....................C..T..
U02030-2/Toronto(TV24)        .........T..T.C..A..T..A..CT....T........GG.C.....
L28880-2/OTH-25/89/J          ........AT..T.C..A..T..A..CT....T........GG.......
AF190817-2/Arg320             T.A..T..A..A.....G..T..A...T..........T..G....TT..
X76716-1/Bristol              .....C............................................
U22498-2/MX                   ........AT..T.C..AA.T..A..CT....T........GG.C.....
#U1/AB039775                  .....C.....T................................C.....
#U3/AB039776                  ..T..T......T..T.G..T.....CCAG..T....AG...G.......
#U4/AB039777                  ..T..T......T..T.G..T.....CCAG..T....AG...G.......
#U16/AB039778                 ..T..T..A..TT..T.A.....A..CCA........AG..GG.C..T..
#U17/AB039779                 ..T..T..A..TT..T.A.....A..CCA........AG..GG.C..T..
#U18/AB039781                 ........AT..T.C..G..T..A..CT.............GG.C.....
#U25/AB039780                 ..T..G..A...T.GT.G..T..T..CCAG..T....AA..GG.G..T..
#U201/AB039782                ........AT..T.C..G..T..A..CT.............GG.C.....
#17                           ..T..T..A...T.T..A.....A..CT.T....................
#19a                          .....G..A..A...T.G..T..A.....T..T....AG...G.......
#19f                          .....N..NT.NT.NT.G..T..A..NN.N..T....A...GG.C.....
#82                           ..T..T......T.C..T.....A..CT.T...........G.....T..
#83                           ..T..T......T.C..T.....A..CT.T...........G.....T..
#84a                          .....G.....A...T.A.....A.....T.......AG...G.C..T..
#84b                          ..T..T......T.C..T.....A..CT.T...........G.....T..
#89                           ..T..T..A.....C..A.........T....T...........C.....
#105e                         ..................................................
#105d                         ..................................................
#16                                                                    ...C.....
#101                                                                   ...C.....
#105a                                                                  GG.C..T..
#105b                                                                  .........
#105c                                                                  .........
#111b                                                                  .........
#18                                                                    GG.C.....
#19b                                                                   GG.C.....
#19c                                                                   GG.C.....
#19d                                                                   .G.......
#19e                                                                   GG.C.....
#26                                                                    GG.C.....
#27b                                                                   GG.C.....
#31                                                                    ...C.....
#32                                                                    ...C.....
#34                                                                    GG.G..T..
#35                                                                    ...C.....
#36                                                                    ...C.....
#37a                                                                   ...C.....
#37b                                                                   ...C.....
#37c                                                                   ...C.....
#53b                                                                   .G.......
#62                                                                    GG.C..T..
#63                                                                    GG.C..T..
#66                                                                    GG.C..T..
#68                                                                    ...C.....
#80a                                                                   G.....T..
#80b                                                                   G.....T..
#80c                                                                   GG.C..T..
#80d                                                                   G.....T..
#109                                                                   .........
#80e                                                                   .T.A.....
#80f                                                                   GG.C..T..
#85                                                                    ...C.....
#88                                                                    ...C.....
#9                                                                     GG.C.....
#49                                                                    .G.......
#93                                                                    ...C.....
#98                                                                    ...C.....
#99                                                                    ...C.....
                              .*.**.**..*..*..*..*.*..**....**.****..**..*.*..**
```

Fig. 2C

| | | | |
|---|---|---|---|
| AF145896/Camberwell | 4951 | GCTACTCATTGCAGAGTTGAAGGAAGGCTGGCATGGACTTTTACGTGCCCA | 5000 |
| X86557/Lorsdale | | ...............AC...................T............. | |
| X81879-2/Melksham | | ...T..G..AT.T..AC....A........A.....T............. | |
| U07611-2/Hawaii | | A.........T....................................... | |
| U02030-2/Toronto(TV24) | | ...G..T..AT.T..AC.T.....G..A..A.....T.....T....... | |
| L23830-2/OTH-25/89/J | | ...G..T..AT.T..AC.T.....G..A..A...........T....... | |
| AF190817-2/Arg320 | | ......T.........C...............................T. | |
| X76716-1/Bristol | | ...............AC...................T............. | |
| U22498-2/MX | | ...G..T..AT.T..AC.T.....G..A..A.....T.....T....... | |
| #U1/AB039775 | | ...G............C...................T............. | |
| #U3/AB039776 | | .A.G.....CAAT...A.T...AGT.....TC....A.....T....... | |
| #U4/AB039777 | | .A.G.....CAAT...A.T...AGT.....TC....A.....T....... | |
| #U16/AB039778 | | .A.G..T..CAGT...A.C...AGT.....TC....G.....T....... | |
| #U17/AB039779 | | .A.C..T..CAGT...A.C...AGT.....TC....G.....T....... | |
| #U18/AB039781 | | ...G..T..AT.T..AC.T.....G..A..A.....T.....T....... | |
| #U25/AB039780 | | AA.G.....CAAT...A.C...AGT.....TC....G............. | |
| #U201/AB039782 | | ...G..T..AT.T..AC.T.....G..A..A.....T.....T....... | |
| #17 | | AT.G.....AA.T..AC.C...........A.....T...........A. | |
| #19a | | AT....T..CA.T...C.C..A..G.....G.....T..C..T..A..A. | |
| #19f | | NN.G..T..CT.T...C.N..N..G..N..A.....T.....T....... | |
| #82 | | AT.G.....AA.T..AC.C..A........G.....T...........A. | |
| #83 | | AT.G.....AA.T..AC.C..A........G.....T...........A. | |
| #84a | | AT....T..CA.T...C.C..A..G.....A.....T...........A. | |
| #84b | | AT.G.....AA.T..AC.C..A........G.....T...........A. | |
| #89 | | ...G..T..CA.....AC.A.................T............. | |
| #105e | | .T....T.........C.A..A..............T............. | |
| #105d | | .T....T.........C.A..A..............T............. | |
| #16 | | ...G............C...................T............. | |
| #101 | | ...G.....CA.....AC.A.................T............. | |
| #105a | | .A.G..T..CAGT...A.C...AGT.....TC....G.....T....... | |
| #105b | | .T....T.........C.A..A..............T............. | |
| #105c | | .T.G..T.........C.A..A..............T............. | |
| #111b | | .T....T.........C.A..A..............T............. | |
| #18 | | ...G..T..AT.T..AC.T.....G..A..A.....T.....T....... | |
| #19b | | ...G..T..AT.T..AC.T.....G..A..A.....T.....T....... | |
| #19c | | ...G..T..AT.T..AC.T.....G..A..A.....T.....T....... | |
| #19d | | AT....T..CA.T...C.C..A..G.....G.....T..C..T..A..A. | |
| #19e | | ...G..T..AT.T..AC.T.....G..A..A.....T.....T....... | |
| #26 | | ...G..T..AT.T..AC.T.....G..A..A.....T.....T....... | |
| #27b | | ......T..AT.T..AC.T.....G..A..A.....T.....T....... | |
| #31 | | ...G............C...................T............. | |
| #32 | | ...G............C...................T............. | |
| #34 | | AA.G.....CAAT...A.C...AGT.....TC....G............. | |
| #35 | | ...G............C...................T............. | |
| #36 | | ...G............C...................T............. | |
| #37a | | ...G............C...................T............. | |
| #37b | | ...G............C...................T............. | |
| #37c | | ...G............C...................T............. | |
| #59b | | AT....T..CA.T...C.C..A..G.....G.....T..C..T..A..A. | |
| #62 | | .A.G..T..CAGT...A.C...AGT.....TC....G.....T....... | |
| #63 | | .A.G..T..CAGT...A.C...AGT.....TC....G.....T....... | |
| #65 | | .A.G..T..CAGT...A.C...AGT.....TC....G.....T....... | |
| #68 | | ...G.....CA.....AC.A.................T............. | |
| #80a | | AT.G.....AA.T..AC.C..A........G.....T...........A. | |
| #80b | | AT.G.....AA.T..AC.C..A........G.....T...........A. | |
| #80c | | .A.G..T..CAGT...A.C...AGT.....TC....G.....T....... | |
| #80d | | AT.G.C...AA.T..AC.C..A........G.....T...........A. | |
| #109 | | .T....T.........C.A..A..............T............. | |
| #80e | | .T....T.........C.A..A..............T............. | |
| #80f | | .A.G..T..CAGT...A.C...AGT.....TC....G.....T....... | |
| #85 | | ...G..T..CA.....AC.A.................T............. | |
| #88 | | ...G..T..CA.....AC.A.................T............. | |
| #9 | | ...G..T..AT.T..AC.T.....G..A..A.....T.....T....... | |
| #49 | | AT....T..CA.T...C.C..A..G.....G.....T..C..T..A..A. | |
| #93 | | ...G..T..CA.....AC.A.................T............. | |
| #98 | | ...G.....CA.....AC.A.................T............. | |
| #99 | | ...G.....CA.....AC.A.................T............. | |
| | | ..*.*..**....**..*.**....**.**..****.**.**.**.**.* | |

Fig. 3A

| | | | |
|---|---|---|---|
| AF145896/Camberwell | 5001 | GACAAGAGCCAATCTTCAGATGGATGAGATTCTCAGATCTGAGCACGTGG | 5050 |
| X86557/Lorsdale | | .................................................. | |
| X81879-2/Melksham | | .G.....A..C...........................T........... | |
| U07611-2/Hawaii | | .G........G..........................C............ | |
| U02030-2/Toronto(TV24) | | ........T..........G........G...........A.....A... | |
| L23830-2/OTH-25/89/J | | ........T..........G........G...........A.....A... | |
| AF190817-2/Arg320 | | .......A.........C.G........G........CT........... | |
| X76716-1/Bristol | | .................................................. | |
| U22498-2/MX | | ........T..........G........G...........A.....A... | |
| #U1/AB039775 | | ............................G..................... | |
| #U3/AB039776 | | ........G.C.....T..G..............T..C..C.....A... | |
| #U4/AB039777 | | ........G.C.....T..G..............T..C..C.....A... | |
| #U16/AB039778 | | ........G.C.....T..G..............T..C..C.....A... | |
| #U17/AB039779 | | ........G.C.....T..G..............T..C..C.....A... | |
| #U18/AB039781 | | ........T.......T..G........G.................A... | |
| #U25/AB039780 | | ....G...G.C....................T.....C..C......... | |
| #U201/AB039782 | | ........T.......T..G........G...........A.....A... | |
| #17 | | ..........T.....T..G..............T..CT........... | |
| #19a | | ....G..A..C..........................C..C..T..T... | |
| #19f | | ........N.C.....T..N........N........C..C.....A... | |
| #82 | | ....G..A..T........G........G..T..T..C............ | |
| #83 | | ....G..A..T........G........G..T..T..C............ | |
| #84a | | .G..G..A..T.....T..G..............T..C..C.....T... | |
| #84b | | ....G..A..T........G........G..T..T..C............ | |
| #89 | | .G........C.....T..G.................CT........... | |
| #105e | | .................................................. | |
| #105d | | .................................................. | |
| #16 | | ............................G..................... | |
| #101 | | .G........C.....T..G.................CT........... | |
| #105a | | ........G.C.....T..G..............T..C..C.....A... | |
| #105b | | ..........................................A....... | |
| #105c | | .................................................. | |
| #111b | | .................................................. | |
| #18 | | ........T.......T..G........G...........A.....A... | |
| #19b | | ........T.......T..G........G...........A.....A... | |
| #19c | | ........T.......T..G........G...........A.....A... | |
| #19d | | ....G..A..C..........................C..C..T..T... | |
| #19e | | ........T.......T..G........G...........A.....A... | |
| #26 | | ........T.......T..G........G...........A.....A... | |
| #27b | | ........T.......T..G........G...........A.....A... | |
| #31 | | .G........T.................G..T.................. | |
| #32 | | .G........T.................G..T.................. | |
| #34 | | ....G...G.C........G...........T.....C..C......... | |
| #35 | | .G........T.................G..T.................. | |
| #36 | | .G........T.................G..T.................. | |
| #37a | | .G........T.................G..T.................. | |
| #37b | | .G........T.................G..T.................. | |
| #37c | | .G........T.................G..T.................. | |
| #53b | | ....G..A..C..........................C..C..T..T... | |
| #62 | | ........G.C.....T..G..............T..C..C.....A... | |
| #63 | | ........G.C.....T..G..............T..C..C.....A... | |
| #66 | | ........G.C.....T..G..............T..C..C.....A... | |
| #68 | | .G........C.....T..G.................CT........... | |
| #80a | | .G..G..A..T........G........G..T..T..CT........... | |
| #80b | | .G..G..A..T........G........G..T..T..CT........... | |
| #80c | | ........G.C.....T..G..............T..C..C.....A... | |
| #80d | | .G..G..A..T........G........G..T..T..CT........... | |
| #109 | | .................................................. | |
| #80e | | .................................................. | |
| #80f | | ........G.C.....T..G..............T..C..C.....A... | |
| #85 | | .G........C.....T..G.................CT........... | |
| #88 | | .G........C.....T..G.................CT........... | |
| #9 | | ........T.......T..G........G...........A.....A... | |
| #49 | | ....G..A..C..........................C..C..T..T... | |
| #93 | | .G........C.....T..G.................CT........... | |
| #98 | | .G........C.....T..G.................CT........... | |
| #99 | | .G........C.....T..G.................CT........... | |
| #27a | | | |

Fig. 3A(Continuation)

#53a
#111a
U46039 Auckland
U75682-1/Snow Mountain strain
AB032758 Chitta virus
AF080549-1/1996/SC
AF080550-1/345-2/96002737/1996/
AF080551-1/004/95M-14/1995/AU
AF080552-1/358/96015107/1996/FL
AF080553-1/364/96019537/1996/AZ
AF080554-1/366/96019554/1996/ID
AF080555-1/373/96019743/1996/SC
AF080556-1/379/96019984/1996/AZ
AF080557-1/384/96025046/1996/FL
AF080558-1/408/97003012/1996/FL
AF080559-1/416/97003156/1996/LA
AF195847-1/Alphatron/98-2/1998/
AF195848-1/Amsterdam/98-18/1998
AJ004864-1/Grimsby
HCA277606/Girlington/93/UK
HCA277607/Hillingdon/90/UK
HCA277608/Leeds/90/UK
HCA277611/Bham132/95/UK
HCA277613/Parkroyal/95/UK
HCA277617/Rbh/93/UK
HCA277618/Wortley/90/UK
HCA277619/Symgreen/95/uk
HCA277620/Seacroft/90/UK
U70059-1/Snow Mountain strain
AB005260-1/SA1/89/Japan
AB005261-1//SA2/91/Japan
AB020547-1/TOB-93-Japan
AB020549-1/TOC1-93-J
AB020551-1/TOC2-93-J
AB020552-1/I210-94-J
AB020563-1/MH22-82-J
AB028244/NLV36
AB028245/NLV21
AB028246/NLV114

```
AF145896/Camberwell       5051 GAGGGCCATCGCAATCTGGCTCCCAGTTTTGTGAATGAAGATGCCCTCGA 5100
X86557/Lorsdale                ..........................C.......................
X81879-2/Melksham              .................T.........C......................
U07611-2/Hawaii                ..................................................
U02030-2/Toronto(TV24)         ....................C.............................
L23830-2/OTH-25/89/J           ..................................................
AF190817-2/Arg320              ..........................C.......................
X76716-1/Bristol               ..........................C.......................
U22498-2/MX                    ....................CT............................
#U1/AB039775                   ..................................................
#U3/AB039776                   .................T.....GAGGG......................
#U4/AB039777                   .................T.....GAGGG......................
#U16/AB039778                  .................T.....GAGAC......................
#U17/AB039779                  .................T.....GAGAC......................
#U18/AB039781                  ..................................................
#U25/AB039780                  .......................GAGAA......................
#U201/AB039782                 ..................................................
#17                            ..................................................
#19a                           .................T.....GAAGG......................
#19f                           .................N......ANNG......................
#82                            ..................................................
#83                            ..................................................
#84a                           .................T.....GAAGG......................
#84b                           ..................................................
#89                            ..................................................
#105e                          ..................................................
#105d                          ..................................................
#16                            ..................................................
#101                           ..................................................
#105a                          .................T.....GAGAG......................
#105b                          ..................................................
#105c                          ..................................................
#111b                          ..................................................
#18                            ..................................................
#19b                           ..................................................
#19c                           ..................................................
#19d                           .................T.....GAAGG......................
#19e                           ..................................................
#26                            ..................................................
#27b                           ..................................................
#31                            ..................................................
#32                            ..................................................
#34                            .......................GAGAA......................
#35                            ..................................................
#36                            ..................................................
#37a                           ..................................................
#37b                           ..................................................
#37c                           ..................................................
#53b                           .................T.....GAAGG......................
#62                            .................T.....GAGAG......................
#63                            .................T.....GAGAG......................
#66                            .................T.....GAGAG......................
#68                            ..................................................
#80a                           ..................................................
#80b                           ..................................................
#80c                           .................T.....GAGAG......................
#80d                           ..................................................
#109                           ..................................................
#80e                           ..................................................
#80f                           .................T.....GAGAG......................
#85                            ..................................................
#88                            ..................................................
#9                             ..................................................
#49                            .................T.....GAAGG......................
#93                            ..................................................
#98                            ..................................................
#99                            ..................................................
#27a                                            T.....GAAGG......................
```

Fig. 3B(Continuation)

| | |
|---|---|
| #53a | T.....GAAGG.................... |
| #111a | T.....GAAGG.................... |
| U46039 Auckland | .................................................. |
| U75682-1/Snow Mountain strain | .................................. |
| AB032758 Chitta virus | ................ |
| AF080549-1/1996/SC | ................ |
| AF080550-1/345-2/96002737/1996/ | ................ |
| AF080551-1/004/95M-14/1995/AU | ................ |
| AF080552-1/358/96015107/1996/FL | ................ |
| AF080553-1/364/96019537/1996/AZ | ................ |
| AF080554-1/366/96019554/1996/ID | ................ |
| AF080555-1/373/96019743/1996/SC | ................ |
| AF080556-1/378/96019984/1996/AZ | ................ |
| AF080557-1/384/96025046/1996/FL | ................ |
| AF080558-1/408/97003012/1996/FL | ................ |
| AF080559-1/416/97003156/1996/LA | ................ |
| AF195847-1/Alphatron/98-2/1998/ | ................ |
| AF195848-1/Amsterdam/98-18/1998 | ................ |
| AJ004864-1/Grimsby | ................ |
| HCA277606/Girlington/93/UK | .....R.......... |
| HCA277607/Hillingdon/90/UK | ................ |
| HCA277608/Leeds/90/UK | ................ |
| HCA277611/Bham132/95/UK | ................ |
| HCA277613/Parkroyal/95/UK | ................ |
| HCA277617/Rbh/93/UK | ................ |
| HCA277618/Wortley/90/UK | ................ |
| HCA277619/Symgreen/95/uk | ................ |
| HCA277620/Seacroft/90/UK | .....R.......... |
| U70059-1/Snow Mountain strain | ................ |
| AB005260-1/SA1/89/Japan | |
| AB005261-1//SA2/91/Japan | |
| AB020547-1/TUB-93-Japan | |
| AB020549-1/TOC1-93-J | |
| AB020551-1/TOC2-93-J | |
| AB020552-1/I210-94-J | |
| AB020563-1/MH22-82-J | |
| AB028244/NLV36 | |
| AB028245/NLV21 | |
| AB028246/NLV114 | |
| | ****************.**..**....********************* |

Fig. 3C

```
AF145896/Camberwell      5101 GTGACGCCAACCCATCTGATGGGTCCGCAGCCAACCTCGTCCCAGAGGTC 5150
X86557/Lorsdale               A.................................................
X81879-2/Melksham             A.......GCT......AC..ATGGT......GG......G.....AAGT
U07611-2/Hawaii               A.......GC.......A...ATGGT......GGT.....A.........
U02030-2/Toronto(TV24)        A......TGCT......A...ATGGT..C...TG.............A..
L23880-2/OTH-25/89/J          A......TGCT......A...ATGGT..C...GG.............A..
AF190817-2/Arg320             A........CT......A...ATGGT..C...GG.............A..
X76716-1/Bristol              A.................................................
U22498-2/MX                   A.CG...TGCT......A...ATGGT..C...TG.............A..
#U1/AB039775                  ........GCT......A...ATGGT......GGT..T..A.......CT
#U3/AB039776                  A.......GCT.....GA...ATGGT..T...........A.......C.
#U4/AB039777                  A.......GCT.....GA...ATGGT..T...........A.......C.
#U16/AB039778                 A......TGCT.....GA...ATGGT..T...........A.......C.
#U17/AB039779                 A......TGCT.....GA...ATGGT..T...........A.......C.
#U18/AB039781                 A......TGCT......A...ATGGT..C...GG.............A..
#U25/AB039780                 A......AGCT.....GA...ATGG...G..TGG......A......A..
#U201/AB039782                A......TGCT......A...ATGGT..C...GG.............A..
#17                           A......TGCT.....AA...ATGGT..C...GG......G.....AAGT
#19a                          A......TGCT......A...ATGGT..C...GG.............A..
#19f                          A......TGCT......A...ATGGT..C...GG.............A..
#82                           A.......GCT......A...ATGGT......GGT.....A.........
#83                           A.......GCT......A...ATGGT......GGT.....A.........
#84a                          A......T.CT.....AA...ATGGT..T...GG......G.....AAGT
#84b                          A.......GCT......A...ATGGT......GGT.....A.........
#89                           A.......GCT......AC..ATGGT......GG......G.....AAGT
#105e                         A........................A........................
#105d                         A........................A........................
#16                           ........GCT......A...ATGGT......GGT..T..A.......CT
#101                          A.......GCT......AC..ATGGT......GG......G.....AAGT
#105a                         A......TGCT.....GA...ATGGT..T...........A.......C.
#105b                         A........................A........................
#105c                         A........................A........................
#111b                         A........................A........................
#18                           A......TGCT......A...ATGGT..C...GG.............A..
#19b                          A......TGCT......A...ATGGT..C...GG.............A..
#19c                          A......TGCT......A...ATGGT..C...GG.............A..
#19d                          A......TGCT......A...ATGGT..C...GG.............A..
#19e                          A......TGCT......A...ATGGT..C...GG.............A..
#26                           A......TGCT......A...ATGGT..C...GG.............A..
#27b                          A......TGCT......A...ATGGT..C...GG.............A..
#31                           A.......GCT......A...ATGGT......GG......G.....AAGT
#32                           A.......GCT......A...ATGGT......GG......G.....AAGT
#34                           A......AGCT.....GA...ATGG...G..TGG......A......A..
#35                           A.......GCT......A...ATGGT......GG......G.....AAGT
#36                           A.......GCT......A...ATGGT......GG......G.....AAGT
#37a                          A.......GCT......A...ATGGT......GG......G.....AAGT
#37b                          A.......GCT......A...ATGGT......GG......G.....AAGT
#37c                          A.......GCT......A...ATGGT......GG......G.....AAGT
#53b                          A......TGCT......A...ATGGT..C...GG.............A..
#62                           A......TGCT.....GA...ATGGT..T...........A.......C.
#63                           A......TGCT.....GA...ATGGT..T...........A.......C.
#66                           A......TGCT.....GA...ATGGT..T...........A.......C.
#68                           A.......GCT......AC..ATGGT......GG......G.....AAGT
#80a                          A.......GCT......A...ATGGT......GGT.....A.........
#80b                          A.......GCT......A...ATGGT......GGT.....A.........
#80c                          A......TGCT.....GA...ATGGT..T...........A.......C.
#80d                          A.......GCT......A...ATGGT......GGT.....A.........
#109                          A........................A........................
#80e                          A........................A........................
#80f                          A......TGCT.....GA...ATGGT..T...........A.......C.
#85                           A.......GCT......AC..ATGGT......GG......G.....AAGT
#88                           A.......GCT......AC..ATGGT......GG......G.....AAGT
#9                            A......TGCT......A...ATGGT..C...GG.............A..
#49                           A......TGCT......A...ATGGT..C...GG.............A..
#93                           A.......GCT......AC..ATGGT......GG......G.....AAGT
#98                           A.......GCT......AC..ATGGT......GG......G.....AAGT
#99                           A.......GCT......AC..ATGGT......GG......G.....AAGT
#27a                          A......TGCT......A...ATGGT..C...GG.............A..
```

Fig. 3C(Continuation)

```
#53a                                      A......TGCT......A...ATGGT..C...GG.............A..
#111a                                     A......TGCT......A...ATGGT..C...GG.............A..
U46039 Auckland                           A......TGCT......A...ATGGT..C...GG.............A..
U75682-1/Snow Mountain strain             A.......GCT......AC..ATGGT......GG......G.....AAGT
AB032758 Chitta virus                     A.......GCT......A...ATGGT......GGT..T..A.......CT
AF080549-1/1996/SC                        A.........................A........................
AF080550-1/345-2/96002737/1996/           A.........................A........................
AF080551-1/004/95M-14/1995/AU             A.........................A........................
AF080552-1/358/96015107/1996/FL           A.........................A........................
AF080553-1/364/96019537/1996/AZ           A.........................A........................
AF080554-1/366/96019554/1996/ID           A.........................A........................
AF080555-1/373/96019743/1996/SC           A........................AA........................
AF080556-1/379/96019984/1996/AZ           A.........................A........................
AF080557-1/384/96025046/1996/FL           A.........................A........................
AF080558-1/403/97003012/1996/FL           A.........................A........................
AF080559-1/416/97003156/1996/LA           A.........................A....................A...
AF195847-1/Alphatron/98-2/1998/           .......TGCT.......CG.ATGGT..G.G..................ACT
AF195848-1/Amsterdam/98-18/1998           A......AGCT.....GA...ATGG...G..TGG......A.......A..
AJ004864-1/Grimsby                        A.........................A........................
HCA277606/Girlington/93/UK                A.......GCT......A...ATGGT......GGT.....A...N.....
HCA277607/Hillingdon/90/UK                A......T.CT.....AA...ATGGT..C...GG......G.....AAGT
HCA277608/Leeds/90/UK                     A......AGCT......A...ATGGT.....AGG......A.....RA..
HCA277611/Rbami32/95/UK                   A......TGCT......A...ATGGT..C...GG.....CT.......A..
HCA277613/Parkroyal/95/UK                 A.S.......................A..............Y........
HCA277617/Rbh/93/UK                       A......TGCT......A...ATGGT..C...GG.............A..
HCA277618/Wortley/90/UK                   ........GCT......A...ATGGT......GGT.....A.......CT
HCA277619/Syngreen/95/uk                  A.........................A........................
HCA277620/Seacroft/90/UK                  A......TGCT.....GA...ATGGT..T...........A.......C.
U70059-1/Snow Mountain strain             A.......GCT......AC..ATGGT......GG......G.....AAGT
AB005260-1/SA1/89/Japan                     ..TGCT..G...A...ATGGT..T...GG......T......A..
AB005261-1//SA2/91/Japan                    ..TGCT......A.C.ATGGT..C...GG.............A..
AB020547-1/TOB-93-Japan                     ..T.CT.....AA...ATGGT..C...GG......G.....AAGT
AB020549-1/TOC1-93-J                        ...GCT......A...ATGGT......GGT.....G.........
AB020551-1/TOC2-93-J                        ..T.CT.....AA...ATGGT..C...GG......G.....AAGT
AB020552-1/IZ10-94-J                        ..T.CT.....AA...ATGGT..C...GG......G.....AAGT
AB020563-1/MH22-82-J                        ..TGCT......A.C.ATGGT..C...GG.............A..
AB028244/NLV36                                TGCT......A...ATGGT..C...GG.............A..
AB028245/NLV21                                TGCT......A...ATGGT..C...GG.............A..
AB028246/NLV114                               AGCT.....GA...ATGG...G..TGG......A......A..
                                          .*..***....**.**....*......*.*.....**.*...**.*...
```

Fig. 4A

```
AF145896/Camberwell      5151 AACAATGAGGTTATGGCTCTGGAGCCCGTTGTTGGTGCCGCTATTGCGGC 5200
X86557/Lorsdale               ..T...............................................
X81879-2/Melksham             ..T........C........T..A.....G.C...C.....CT.G..A..
U07611-2/Hawaii               .....C...ACG.....C..C..A..G..G.C...G..TT....A..C..
U02030-2/Toronto(TV24)        ..........CA.....G..A.....A..G.CC...T.A..G..A..A..
L23830-2/OTH-25/89/J          ..........CA.....G..A..T..A..G.CG.....A..C..A..A..
AF190817-2/Arg320             ..........CA.....G..A..C..A..G.CG.....A..G..A..A..
X76716-1/Bristol              ..T...............................................
U22498-2/MX                   ..........CA.....G..A.....A..G.CG.....A..G..A..A..
#U1/AB039775                  .........ACC.....A..T..A..G..G.C...G..TT.A..A..C..
#U3/AB039776                  .................A..T..A..G..G..A..A...T.A..C..A..
#U4/AB039777                  .................A..T..A..G..G..A..A...T.A..C..A..
#U16/AB039778                 .................A..T..A..G..G..C..A...T.A.....A..
#U17/AB039779                 .................A..T..A..G..G..G..A...T.A.....A..
#U18/AB039781                 ..........CA.....G..A.....A..G.CG..C..A..G..A..A..
#U25/AB039780                 ...C.......C.....CA.A..A..T.....CA.G...T..T.A..A..
#U201/AB039782                ..........CA.....G..A.....A..G.CG..C..A..G..A..A..
#17                           ..T.......CA.....C.....A.....G..G..G.TGT..T.A..C..
#19a                          ..........CA.....G..A..C..A..G.CG.....A..A..A..A..
#19f                          ..........CA.....G..A..N..A..G.CG.....A..N..A..A..
#82                           .....C...ACA.....A..T.....A....CG..A..TT.A..C..C..
#83                           .....C...ACA.....A..T.....A....CG..A..TT.A..C..C..
#84a                          ..........CA...........A.....G..G..G..GT..T.A..C..
#84b                          .....C...ACA.....A..T.....A....CG..A..TT.A..C..C..
#89                           ..T........C........T..A.....G.C..........T.G..A..
#105e                         ..................T...............................
#105d                         ..................T...............................
#16                           .........ACC.....A..T..A..G..G.C...G..TT.A..A..C..
#101                          ..T........C........T..A.....G.C..........T.G..A..
#105a                         .................A..T..A..G..G..G..A...T.A.....A..
#105b                         ..................T...............................
#105c                         ..................T...............................
#111b                         ..................T...............................
#18                           ..........CA.....G..A.....A..G.CG..C..A..G..A..A..
#19b                          ..........CA.....G..A.....A..G.CG..C..A..G..A..A..
#19c                          ..........CA.....G..A.....A..G.CG..C..A..G..A..A..
#19d                          ..........CA.....G..A..C..A..G.CG.....A..A..A..A..
#19e                          ..........CA.....G..A..C..A..G.CG.....A..A..A..A..
#26                           ..........CA.....G..A.....A..G.CG..C..A..G..A..A..
#27b                          ..........CA.....G..A.....A..G.CG..C..A..G..A..A..
#31                           ....................T..A..T....C...G..AT..T.A..T..
#32                           ....................T..A..T....C...G..AT..T.A..T..
#34                           ...C.......C.....CA.A..A..T.....CA.G...T..T.A..A..
#35                           ....................T..A..T....C...G..AT..T.A..T..
#36                           ....................T..A..T....C...G..AT..T.A..T..
#37a                          ..............C.....T..A..T....C...G..AT..T.A..T..
#37b                          ....................T..A..T....C...G..AT..T.A..T..
#37c                          ....................T..A..T....C...G..AT..T.A..T..
#53b                          ..........CA.....G..A..C..A..G.CG.....A..A..A..A..
#62                           .................A..T..A..G..G..G..A...T.A.....A..
#63                           .................A..T..A..G..G..G..A...T.A.....A..
#66                           .................A..T..A..G..G..G..A...T.A.....A..
#68                           ..T........C........T..A.....G.C..........T.G..A..
#80a                          .....C...ACA.....A..T..A..A....CG..A..TT.A..C..T..
#80b                          .....C...ACA.....A..T..A..A....CG..A..TT.A..C..T..
#80c                          .................A..T..A..G..G..G..A...T.A.....A..
#80d                          .....C...ACA.....A..T..A..A....CG..A..TT.A..C..T..
#109                          ..................T...............................
#80e                          ..................T...............................
#80f                          .................A..T..A..G..G..G..A...T.A.....A..
#85                           ..T........C........T..A.....G.C..........T.G..A..
#88                           ..T........C........T..A.....G.C..........T.G..A..
#9                            ..........CA.....G..A.....A..G.CG.....A..C..A..A..
#49                           ..........CA.....G..A..C..A..G.CG.....A..A..A..A..
#93                           ..T........C........T..A.....G.C..........T.G..A..
#98                           ..T........C........T..A.....G.C..........T.G..A..
#99                           ..T........C........T..A.....G.C..........T.G..A..
#27a                          ..........CA.....G..A..C..A..G.CG.....A..A..A..A..
```

Fig. 4A(Continuation)

```
#53a                                  ..........CA.....G..A..C..A..G.CG.....A..A..A..A..
#111a                                 ..........CA.....G..A..C..A..G.CG.....A..A..A..A..
U46039 Auckland                       ..........CA.....G..A.....A..G.CG.....A..G..A..A..
U75682-1/Snow Mountain strain         ..T........C........T........G.C......T..CT.G..A..
AB032758 Chitta virus                 .........ACC.....A..T..A..G..G.C...G..TT.A..A..C..
AF080549-1/1996/SC                    .................T................................
AF080550-1/345-2/96002737/1996/       .................T.............C..................
AF080551-1/004/95M-14/1995/AU         .................T................................
AF080552-1/358/96015107/1996/FL       .................T................................
AF080553-1/364/96019537/1996/AZ       .................T................................
AF080554-1/366/96019554/1996/ID       .................T................................
AF080555-1/373/96019743/1996/SC       .................T................................
AF080556-1/379/96019984/1996/AZ       .................T................................
AF080557-1/384/96025046/1996/FL       .................T................................
AF080558-1/408/97003012/1996/FL       .................T.......................C........
AF080559-1/416/97003156/1996/LA       .................T................................
AF195847-1/Alphatron/98-2/1998/       C.AC.A....AT..C.C..C.CC........CG..C..T..AC.A.....
AF195848-1/Amsterdam/98-18/1998       ...C.......C.....CA.A..A..T....CA..G...T..T.A..A..
AJ004864-1/Grimsby                    .................T....A...........................
HCA277606/Girlington/93/UK            .....C..BACR.....A..C..A..G..G.C...G..TT.C..A..C..
HCA277607/Hillingdon/90/UK            ..T.......CA...........A.....G..G..G..GT..T.A..C..
HCA277608/Leeds/90/UK                 ...........C...C.C..T.........G.C......AT.GC.G...A
HCA277611/Bham132/95/UK               ..........CA.....G..A.....A..G.CG.....A..G..A..A..
HCA277613/Parkroyal/95/UK             .................T..............................A..
HCA277617/Rbh/93/UK                   ..........CA.....G..A.....A..G.CG.....A..G..A..A..
HCA277618/Wortley/90/UK               ...GW....ACC.....A..T..A..G..G.C...G..TT.A..A..C..
HCA277619/Symgreen/95/uk              .................T...........................C....
HCA277620/Seacroft/90/UK              .G...............A..T..A..G..G..G..A...T.A..C..A..
U70059-1/Snow Mountain strain         ..T........C........T........G.C......T..CT.G..A..
AB005260-1/SA1/89/Japan               ..........CA.....G..A.....A..A.CG.....A..A..A..A..
AB005261-1//SA2/91/Japan              ..........CA.....G..A..C..A..G.CG.....A..G..A..A..
AB020547-1/TOB-93-Japan               ..T.......CA...........A.....G..G..G..GT..T.A..C..
AB020549-1/TOC1-93-J                  .....C...ACG.....A..C..A..G..G.C...G..TT.C..A..C..
AB020551-1/TOC2-93-J                  ..T.......CA...........A.....G..G..G..GT..T.A..C..
AB020552-1/IZ10-94-J                  ..T.......CA...........A.....G..G..G..GT..T.A..C..
AB020563-1/MH22-82-J                  ..........CA.....G..A.....A..G.CA.....A..A..A..A..
AB028244/NLV36                        ..........CA.....G..A..C..A..G.CG.....A..G..A..A..
AB028245/NLV21                        ..........CA.....G..A..C..A..G.CG.....A..G..A..A..
AB028246/NLV114                       ...C.......C.....CA.A..A..T....CA..G...T..T.A..A..
                                      ......**.....*.*..*.*..**.**.*..**.....*..*.**..*
```

Fig. 4B

```
AF145896/Camberwell      5201 ACCTGTAGCGGGCCAACAAAATATAATTGACCCCTGGATTAGAAATAATT 5250
X86557/Lorsdale               ......G..............CG......................C....
X81879-2/Melksham             C..G..CA.C..T...AC.........A....T.........GCA....
U07611-2/Hawaii               C...C..A.C..T...A.T...G.G..A................TG..C.
U02030-2/Toronto(TV24)        T..CC.CA.T.....G..............T..........TG.......
L23880-2/OTH-25/89/J          ...CC.CA.T.....G..............T..........TG.....C.
AF190817-2/Arg320             ...CC.CA.T..T..G.....C........T..........TG.......
X76716-1/Bristol              ......G..............CG......................C....
U22498-2/MX                   G..CC.CA.T.....G..............T..........TG.......
#U1/AB039775                  C..AC.CA.C..T...A.C.....T..A...............TTA....
#U3/AB039776                  T.....T.TC..T..G...........................G.A....
#U4/AB039777                  T.....T.TC..T..G...........................G.A....
#U16/AB039778                 T.....C.TC..T..............................G.A....
#U17/AB039779                 T.....C.TC..T..............................G.A....
#U18/AB039781                 G..CC.CA.T.....G..............T..........TG.......
#U25/AB039780                 C.....C.TA..A...TC............T...................
#U201/AB039782                G..CC.CA.T.....G..............T..........TG.......
#17                           C.....CA.T......ACT........A...............C.....
#19a                          ...CC.TA.T.....G..............T..........TG.....C.
#19f                          G..CC.CA.T.....G..............T..........TG.....N.
#82                           C...T..A.T..T...A.C...G....A...............TTA....
#83                           C...T..A.T..T...A.C...G....A...............TTA....
#84a                          C.....CA.T......ACT........A...............C.....
#84b                          C...T..A.T..T...A.C...G....A...............TTA....
#89                           C..G..CA.C......AC......T..A....T.........GCA....
#105e                         ......................G...........................
#105d                         ......................G...........................
#16                           C..AC.CA.C..T...A.C.....T..A...............TTA....
#101                          C..G..CA.C......AC......T..A....T.........GCA....
#105a                         T.....C.TC..T..............................G.A....
#105b                         ......................G...........................
#105c                         ......................G...........................
#111b                         ......................G...........................
#18                           G..CC.CA.T.....G..............T..........TG.......
#19b                          G..AC.CA.T.....G..............T..........TG.......
#19c                          G..CC.CA.T.....G..............T..........TG.......
#19d                          ...CC.TA.T.....G..............T..........TG.....C.
#19e                          ...CC.TA.T.....G..............T..........TG.....C.
#26                           G..CC.CA.T.....G..............T..........TG.......
#27b                          G..CC.CA.T.....G..............T..........TG.......
#31                           C.....GA.T..T...ACT..............A....C...TG....
#32                           C.....GA.T..T...ACT..............A....C...TG....
#34                           C.....C.TA..A...TT..C.........T...................
#35                           C.....GA.T..T...ACT..............A....C...TG....
#36                           C.....CA.T..T...ACT..............A....C...TG....
#37a                          C.....GA.T..T...ACT.............TA...CC...TG...C
#37b                          C.....GA.T..T...ACT..............A....CG..TG....
#37c                          C.....GA.T..T...ACT..............A....C...TG....
#53b                          ...CC.TA.T.....G..............T..........TG.....C.
#62                           T.....C.TC..T..............................G.A....
#63                           T.....C.TC..T..............................G.A....
#66                           T.....C.TC..T..............................G.A....
#68                           C..G..CA.C......AC......T..A....T.........GCA....
#80a                          C..CT..A.T..T...A.C...G....A...............TTA....
#80b                          C..CT..A.T..T...A.C...G....A..........C....TTA..C
#80c                          T.....C.TC..T..............................G.A....
#80d                          C..CT..A.T..T...A.C...G....A...............TTA....
#109                          ......................G...........................
#80e                          ......................G...........................
#80f                          T.....C.TC..T..............................G.A....
#85                           C..G..CA.C......AC......T..A....T.........GCA....
#88                           C..G..CA.C......AC......T..A....T.........GCA....
#9                            G..CC.CA.T.....G..............T..........TG.......
#49                           ...CC.TA.T.....G..............T..........TG.....C.
#93                           C..G..CA.C......AC......T..A....T.........GCA....
#98                           C..G..CA.C......AC......T..A....T.........GCA....
#99                           C..G..CA.C......AC......T..A....T.........GCA....
#27a                          ...CC.TA.T.....G..............T..........TG.....C.
```

Fig. 4B(Continuation)

```
#53a                                      ...CC.TA.T.....G..............T.........TG......C.
#111a                                     ...CC.TA.T.....G..............T.........TG......C.
U46039 Auckland                           G..CC.GA.T.....G..............T.........TG........
U75682-1/Snow Mountain strain             C..G..CA.C..T..AC.......T..A.....T........GCA.....
AB082758 Chitta virus                     C..AC.CA.C......A.C.....T..A..............TTA.....
AF080549-1/1996/SC                        ......................G...........................
AF080550-1/345-2/96002787/1996/           ......................G...........................
AF080551-1/004/95M-14/1995/AU             ......................G...........................
AF080552-1/358/96015107/1996/FL           ......................G...........................
AF080553-1/364/96018537/1996/AZ           ......................G...........................
AF080554-1/366/96018554/1996/ID           ......................G...........................
AF080555-1/373/96019743/1996/SC           ......................G...........................
AF080556-1/379/96019984/1996/AZ           ......................G...........................
AF080557-1/384/96025046/1996/FL           ......................G...........................
AF080558-1/408/97003012/1996/FL           ......................G...........................
AF080559-1/416/97003156/1996/LA           ......................G...........................
AF195847-1/Alphatron/98-2/1998/           ...C....T...G..GAC...C...................A.G.A....
AF195848-1/Amsterdam/98-18/1998           C.....C.TA..A....TT...........T...................
AJ004864-1/Grimsby                        ......................G...........................
HCA277606/Girlington/93/UK                C...C..A.C..T...A.C...G.G..A................TG..C.
HCA277607/Hillingdon/90/UK                C.....CA.T.......ACT.......A................C.....
HCA277608/Leeds/90/UK                     ...A..T.TT..G........C........T........A..........
HCA277611/Bham132/95/UK                   G..CC.CA.T.....G..............T.........TG........
HCA277613/Parkroyal/96/UK                 ......................G...........................
HCA277617/Rbh/93/UK                       G..CC.CA.T.....G..............T.........TG........
HCA277618/Wortley/90/UK                   C..AC.CA.C......A.C.....T..A.............R.TTA..C.
HCA277619/Symgreen/95/uk                  ......................C.....................G.....
HCA277620/Seacroft/90/UK                  T.....T.TC..T..G...........................G.A....
U70059-1/Snow Mountain strain             C..G..CA.C..T..AC.......T..A.....T........GCA.....
AB005260-1/SA1/89/Japan                   ...CC.CA.T..T..G..............T.........TG........
AB005261-1//SA2/91/Japan                  G..CC.CA.T..A..G.....C........T.........TG........
AB020547-1/TOB-93-Japan                   C.....CA.T.......ACT.......A................C.....
AB020549-1/TOC1-93-J                      C...C..A.C..T...A.C...G.G..A..............G.TG..C.
AB020551-1/TOC2-93-J                      C.....CA.T.......ACT.......A................C.....
AB020552-1/IZ10-94-J                      C.....CA.T.......ACT.......A................C.....
AB020563-1/MH22-82-J                      ....C.CA.T.....G..............T.........TG......C.
AB028244/NLV36                            ...CC.CA.T..T..G.....C........T.........TG........
AB028245/NLV21                            ...CC.CA.T..T..G.....C........T.........TG........
AB028246/NLV114                           C.....C.TA..A....TT...........T...................
                                          .**..*....**.**....**..*.**.**.*..****........**..
```

Fig. 4C

| | | | |
|---|---|---|---|
| AF145896/Camberwell | 5251 | TTCTACAAGCCCCTGGTGGAGAGTTTACAGTGTCCCCTAGAAACGCTCCA | 5300 |
| X86557/Lordsdale | | .........................C........................ | |
| X81879-2/Melksham | | ....C..G......AA...T..A........T..T..CC.C..T..C..T | |
| U07611-2/Hawaii | | ....C........AAA......A..C........T..CC.C..TT....T | |
| U02030-2/Toronto(TV24) | | ..........A........T..............A..C..G..TT.C..T | |
| L23830-2/OTH-25/89/J | | ....G.....A........T..............A.....G..TT.C..T | |
| AF190817-2/Arg320 | | ....G.....A........T.....................G..TC.C..T | |
| X76716-1/Bristol | | .........................C........................ | |
| U22498-2/MX | | ....G.....A........T..............A..C..G..TT.C..T | |
| #U1/AB039775 | | ....G..G..T..CAA...G.....C..G..T..A..CC.C...T.G..C | |
| #U3/AB039776 | | ....C.....A..ACAG..C........T..T..G..A..G..TT.G..T | |
| #U4/AB039777 | | ....C.....A..ACAG..C........T..T..G..A..G..TT.G..T | |
| #U16/AB039778 | | ....T..G..A..ACAG..T........T..T..A..A......T.G..T | |
| #U17/AB039779 | | ....T..G..A..ACAG..T........T..T..A..A......T.G..T | |
| #U18/AB039781 | | ....G.....A........T..............A.....G..TT.C..T | |
| #U25/AB039780 | | ....G..........C......A.....T..T..A........T...... | |
| #U201/AB039782 | | ....G.....A........T..............A.....G..TT.C..T | |
| #17 | | ....C.........AA...T..A........T............TT.C..T | |
| #19a | | ....G.....A........T.....C........A........TT....T | |
| #19f | | ....G.....A........T.....N........A.....N..TT.N..T | |
| #82 | | .............CAA...T.....C..G..T.....CC.....T.G..T | |
| #83 | | .............CAA...T.....C..G..T.....CC.....T.G..T | |
| #84a | | ....C.........AA...T..A..C.....T............TT.C..T | |
| #84b | | .............CAA...T.....C..G..T.....CC.....T.G..T | |
| #89 | | ....C..G......AA...T..A........T..T..CC.T..T..C..T | |
| #105e | | ...............................A.................G | |
| #105d | | ...............................A.................G | |
| #16 | | ....G..G..T..CAA...G.....C..G..T..A..CC.C...T.G..C | |
| #101 | | ....C..G......AA...T..A........T..T..CC.T..T..C..T | |
| #105a | | ....T..G..A..ACAG..T........T..T..A..A......T.G..T | |
| #105b | | ...............................A.................G | |
| #105c | | ...............................A.................G | |
| #111b | | ...............................A.................G | |
| #18 | | ....G.....A........T..............A.....G..TT.C..T | |
| #19b | | ....G.....A........T..............A.....G..TT.C..T | |
| #19c | | ....G.....A........T..............A.....G..TT.C..T | |
| #19d | | ....G.....A........T.....C.T......A........TT....T | |
| #19e | | ....G.....A........T.....C........A........TT....T | |
| #25 | | ....G.....A........T..............A.....G..TT.C..T | |
| #27b | | ....G.....A........T..............A.....G..TT.C..T | |
| #31 | | ....T........AAA......A..C..T..T.....A.....TT.C..T | |
| #32 | | ....T........AAA......A..C..T..T.....A.....TT.C..T | |
| #34 | | ....G..........C......A.....T..T..A..C.....T...... | |
| #35 | | ....T........AAA......A..C..T..T.....A.....TT.C..T | |
| #36 | | ....T........AAA......A..C..T..T.....A.....TT.C..T | |
| #37a | | ....T........AAA......A..C..T..T.....A.....TT.C..T | |
| #37b | | ....T........AAA......A..C..T..T.....A.....TT.C..T | |
| #37c | | ....T........AAA......A..C..T..T.....A.....TT.C..T | |
| #58b | | ....G.....A........T.....C........A........TT....T | |
| #62 | | ....T..G..A..ACAG..T........T..T..A..A......T.G..T | |
| #63 | | ....T..G..A..ACAG..T........T..T..A..A......T.G..T | |
| #66 | | ....T..G..A..ACAG..T........T..T..A..A......T.G..T | |
| #68 | | ....C..G......AA...T..A........T..T..CC.T..T..C..T | |
| #80a | | .............CAA...T.....C..G..T.....CC.....T.G..T | |
| #80b | | .............CAA...T.....C..G..T.....CC.....T.G..T | |
| #80c | | C...T..G..A..ACAG..T........T..T..A..A......T.G..T | |
| #80d | | .............CAA...T.....C..G..T.....CC.....T.G..T | |
| #108 | | ...............................A.................G | |
| #80e | | ...............................A.................G | |
| #80f | | ....T..G..A..ACAG..T........T..T..A..A......T.G..T | |
| #85 | | ....C..G......AA...T..A........T..T..CC.T..T..C..T | |
| #88 | | ....C..G......AA...T..A........T..T..CC.T..T..C..T | |
| #9 | | ....G.....A........T..............A.....G..TT....T | |
| #49 | | ....G.....A........T.....C........A........TT....T | |
| #93 | | ....C..G......AA...T..A........T..T..CC.T..T..C..T | |
| #98 | | ....C..G......AA...T..A........T..T..CC.T..T..C..T | |
| #99 | | ....C..G......AA...T..A........T..T..CC.T..T..C..T | |
| #27a | | ....G.....A........T.....C........A........TT....T | |

Fig. 4C(Continuation)

```
#59a                             ....G.....G........T.....C........A........TT....T
#111a                            ....G.....A........T....C.........A........TT....T
U46039 Auckland                  ....G.....A........T..............A....G..TT.C..T
U75682-1/Snow Mountain strain    ....C..G......AA...T..A........T..T..CC.T..T..C..T
AB082758 Chitta virus            ....G..G..T..CAA........C...G..T..A..CC.C...T.A..C
AF080549-1/1996/SC               ................................A.................G
AF080550-1/345-2/96002737/1996/  ................................A.................G
AF080551-1/004/95M-14/1995/AU    ................................A.................G
AF080552-1/358/96015107/1996/FL  ................................A.................G
AF080553-1/364/96019537/1996/AZ  ................................A.................G
AF080554-1/366/96018554/1996/ID  ....G...........................A.................G
AF080555-1/373/96019743/1996/SC  ................................A.................G
AF080556-1/379/96019984/1996/AZ  ................................A.................G
AF080557-1/384/96025046/1996/FL  ................................A.................G
AF080558-1/408/97003012/1996/FL  ........................G..........................G
AF080559-1/416/97003156/1996/LA  ...................................................G
AF195847-1/Alphatron/98-2/1998/  ....T........CCAG..T...........C..A....A...TT....T
AF195848-1/Amsterdam/98-18/1998  .............C.....A....T..T..A........T.....C
AJ004864-1/Grimsby               ................................A.................G
HCA277606/Girlington/93/UK       ....T........AAA...T..A........T..CC.T...T....T
HCA277607/Hillingdon/90/UK       ....C........AA....T..A..C....T........A..TT.C..T
HCA277608/Leeds/90/UK            ....C........CA..T........C........G..TT.C..C
HCA277611/Bham192/95/UK          ....G.....A........T...........A....G..TT....T
HCA277613/Parkroyal/95/UK        ...........................A.....A.................G
HCA277617/Rbh/93/UK              ...CG.....A........T...........A.....G....T.C..T
HCA277618/Wortley/90/UK          ....G..G..T..CAA....R...C..G..T..A..CC.C...T.A..T
HCA277619/Symgreen/95/uk         .............................A.....................
HCA277620/Seacroft/90/UK         ....C......A..ACAC..C.....C..T..T..A..A..G..TT.G..T
U70059-1/Snow Mountain strain    ....C..G......AA...C..A........T..T..CC.T..T..C..T
AB005260-1/SA1/89/Japan          ....G..G..A........T.............A..C......T.C..T
AB005261-1//SA2/91/Japan         ....G.....A........T...........A.....G..TT.C..T
AB020547-1/TOB-93-Japan          ....C........AA....T..A..C....C..........TT.C..T
AB020549-1/TOC1-93-J             ....T........AAA...T..A........A..T..CC.T..TT....T
AB020551-1/TOC2-93-J             ....C........AA....T..A..C....C..........TT.C..T
AB020552-1/IZ10-94-J             ....C........CAA...T..A........T...........TT.C..T
AB020563-1/MH22-82-J             ....G.....A........T...........A.....G...T.C..T
AB028244/NLV36                   ....G.....A........T...................G..TT.C..T
AB028245/NLV21                   ....G.....A........T...................G..TT.C..T
AB028246/NLV114                  ....G........C.....A....T..T..A........T......
                                 .##..##.##.##....##..#.##.#..##.##.##.....##..#.##.
```

Fig. 5A

```
AF145896/Camberwell       5301 GGTCAGATACTATGGAGCGCGCCCTTGGCCCCTGATTTGAATCCCTATCT 5350
X86557/Lorsdale                ...........G.........................C....C........
X81879-2/Melksham              .....AG.G...T..ATCTAGAG.....T..A..A........T.....
U07611-2/Hawaii                .....A..CT.GCTA.ATTT.GAA..A.........A..A.....A.TCT.
U02030-2/Toronto(TV24)         .....AG.G..TCTT.A.TT.GAG..A..T..A..AA.A.....T...T.
L23830-2/OTH-25/89/J           .....AG.G..TCTT.ATTT.GAA..A..T..A..AA.A..........T.
AF190817-2/Arg320              .....AG.G..TCTT.ATTT.GAA........A..AA.A..C.......T.
X76716-1/Bristol               ...........G.........................C....C........
U22498-2/MX                    .....AG.G..TCTT.ATTT.CAA..A..T..A..AA.A.....T...T.
#U1/AB039775                   ..G..AG.C....TA.A.TT.GAA..A.....C..AC.A.....A..C..
#U8/AB039776                   ........G..T.TA.A.CTTGAG........A..AC.T..C.......T.
#U4/AB039777                   ........G..T.TA.A.CTTGAG........A..AC.T..C.......T.
#U16/AB039778                  ........G..T.TA.ATCTTGAA..A.....A..GC.C.....T..C..
#U17/AB039779                  ........G..T.TA.ATCTTGAA..A.....A..GC.C.....T..C..
#U18/AB039781                  .....AG.G..TCTT.ATTT.GAA..A..T..A..AA.A..C.......T.
#U25/AB039780                  .....AT.TT...TAGATCTAGAG..A.........G.....C.....C..
#U201/AB039782                 .....AG.G..TCTT.ATTT.GAA..A..T..A..AA.A..C.......T.
#17                            ..A......T.GGTC.ATTT.GAG.....T..A..AC........T.....
#19a                           .....AG.GT..CTT.ATTT.GAA.....T..A..AA.A.........CT.
#19f                           .....AG.G..TCTT.ATTT.GAA..A..T..A..AA.N.........CTG
#82                            .....A..TT.G.TA.ATTT.GAG..A..G.....A.........A...T.
#83                            .....A..TT.G.TA.ATTT.GAG..A..G.....A.........A...T.
#84a                           ..A......T.GGTC.ATTT.GAG.....T..A..AC....C..T.....
#84b                           .....A..TT.G.TA.ATTT.GAG..A..G.....A.........A...T.
#89                            .....AG.G....T..ATCTAGAG.....T..A..A..A.....T.....
#105e                          .....................................AT..GA.CC..TACCT.
#105d                          ..........................................C.....C..
#16                            ..G..AG.C....TA.A.TT.GAA..A.....C..AC.A.....A..C..
#101                           .....AG.G....T..ATCTAGAG.....T..A..A..A....TT.....
#105a                          ........G..T.TA.ATCTTGAA..A.....A..GC.C.....T..C..
#105b                          ..........................................C.....C..
#105c                          ..........................................C.....C..
#111b                          ..........................................C.....C..
#18                            .....AG.G..TCTT.ATTT.GAA..A..T..A..AA.A..C.......T.
#19b                           .....AG.G..TCTT.ATTT.GAA..A..T..A..AA.A..C.......T.
#19c                           .....AG.G..TCTT.ATTT.GAA..A..T..A..AA.A..C.......T.
#19d                           .....AG.GT..CTT.ATTT.GAA.....T..A..AA.A.........CT.
#19e                           .....AG.GT..CTT.ATTT.GAA..A..T..A..AA.A..C.......T.
#26                            .....AG.G..TCTT.ATTT.GAA..A..T..A..AA.A..C.......T.
#27b                           .....AG.G..TCTT.ATTT.GAA..A..T..A..AA.A..C..T....T.
#31                            ..A..AG....CCTA.ATTT.GAA.....T.....A..A..C..T.....
#32                            ..A..AG....CCTA.ATTT.GAA.....T.....A..A..C..T.....
#34                            .....AT.TT.G.TAGATTTAGAG..A.........A.....C.....C..
#35                            ..A..AG....CCTA.ATTT.GAA.....T.....A..A..C..T.....
#36                            ..A..AG....CCTA.ATTT.GAA.....T.....A..A..C..T.....
#37a                           ..A..AG....CCTA.ATTT.GAA.....T.....A..A..C..T.....
#37b                           ..A..AG....CCTA.ATTT.GAA.....T.....A..A..C..T.....
#37c                           ..A..AG....CCTA.ATTT.GAAC....T.....A..A..C..T.....
#53b                           .....AG.GT..CTT.ATTT.GAA.....T..A..AA.A.........CT.
#62                            ........G..T.TA.ATCTTGAA..A.....A..GC.C.....T..C..
#63                            ........G..T.TA.ATCTTGAA..A.....A..GC.C.....T..C..
#66                            ........G..T.TA.ATCTTGAA..A.....A..GC.C.....T..C..
#68                            .....AG.G....T..ATCTAGAG.....T..A..A..A.....T.....
#80a                           .....A..TT.G.TA.ATTT.GAG..A..A.....A.....C..A...T.
#80b                           .....A..TT.G.TA.ATTT.GAG..A..A.....A.....C..A...T.
#80c                           ........G..T.TA.ATCTTGAA..A.....A..GC.C.....T..C..
#80d                           .....A..TT.G.TA.ATTT.GAG..A..A.....A.....C..A...T.
#109                           ..........................................C.....C..
#80e                           ..........................................C.....C..
#80f                           ........G..T.TA.ATCTTGAA..A.....A..GC.C.....T..C..
#85                            .....AG.G....T..ATCTAGAG.....T..A..A..A.....T.....
#88                            .....AG.G....T..ATCTAGAG.....T..A..A..A.....T.....
#9                             .....AG.G..TCTC.ATTT.GAA..A..T..A..AA.A..........T.
#49                            .....AG.GT..CTT.ATTT.GAA.....T..A..AA.A.........CT.
#93                            .....AG.G....T..ATCTAGAG.....T..A..A..A.....T.....
#98                            .....AG.G....T..ATCTAGAG.....T..A..A..A.....T.....
#99                            .....AG.G....T..ATCTAGAG.....T..A..A..A.....T.....
#27a                           .....AG.GT..CTT.ATTT.GAA.....T..A..AA.A.........CT.
```

Fig. 5A(Continuation)

| | |
|---|---|
| #53a | .....AG.GT..CTT.ATTT.GAA.....T..A..AA.A.......CT. |
| #111a | .....AG.GT..CTT.ATTT.GAA.....T..A..AA.A.......CT. |
| U46039 Auckland | .....AG.G..TCTT.ATTT.GAG..A..T..A..AA.A..C......T. |
| U75682-1/Snow Mountain strain | .....AG.G....TA.ATCTAGAA.....T..A..A..A....T..... |
| AB032758 Chitta virus | ..G..AG.C....TA.ATTT.GAA..A.....C..AC.A.....A..C.. |
| AF080549-1/1996/SC | ..........................A..............C.....C.. |
| AF080550-1/345-2/96002737/1996/ | .........................................C.....C.. |
| AF080551-1/004/95M-14/1995/AU | .........................................C..T..C.. |
| AF080552-1/358/96015107/1996/FL | ..........................A..............C.....C.. |
| AF080553-1/364/96019537/1996/AZ | ..........................A..............C.....C.. |
| AF080554-1/366/96019554/1996/ID | ..........................A..............C.....C.. |
| AF080555-1/373/96019743/1996/SC | ..........................A..............C.....C.. |
| AF080556-1/379/96019984/1996/AZ | ..........................A..............C.....C.. |
| AF080557-1/384/96025046/1996/FL | ..........................A........C.....C.....C.. |
| AF080558-1/408/97003012/1996/FL | .........................................C.....C.. |
| AF080559-1/416/97003156/1996/LA | .....A...................................C.....C.. |
| AF195847-1/Alphatron/98-2/1998/ | .....A..TT..GTC.ATTT.GAA.....A..CA.AC.C..C........ |
| AF195848-1/Amsterdam/98-18/1998 | .....AT.TT.G.TAGATTTAGAGC.A........A..A..C........ |
| AJ004864-1/Grimsby | .........................................C.....C.. |
| HCA277606/Girlington/93/UK | .....A..T..G.TA.ATTTAGAA..A..T.....A..A.....A.TCT. |
| HCA277607/Hillingdon/90/UK | ..A.....T.GGTC.ATTT.GAG.....T..A..AC....C..T..... |
| HCA277608/Leeds/90/UK | .....A..C..GCTTGATTTAGAG.....A..A..A.....C.....C.. |
| HCA277611/Bham132/95/UK | .....AG.G..TCTT.ATTT.GAA..A..T..A..AA.A.........T. |
| HCA277613/Parkroyal/95/UK | .........................................C.....C.. |
| HCA277617/Bbh/93/UK | .....AG.G..TCTT.ATTT.GAA..A..T..A..AA.A.........T. |
| HCA277618/Wortley/90/UK | ..G..AG.C...CTA.ATTT.GAA..A.....C..AC.A.....A..... |
| HCA277619/Symgreen/95/uk | .........................................C.....C.. |
| HCA277620/Seacroft/90/UK | ........G..C.TA.A.CTTCAG........A..AC.T.........T. |
| U70059-1/Snow Mountain strain | .....AG.G....TA.ATCTAGAA.....T..A..A..A.....T..... |
| AB005260-1/SA1/89/Japan | .....AG.G..TCTT.ATTTAGAA..A..T..A..AA.A.........T. |
| AB005261-1//SA2/91/Japan | .....AG.G..TCTA.ATTTAGAA..A.....A..AA.A..C........ |
| AB020547-1/TOB-93-Japan | ..A.....T.GGTC.ATTT.GAG.....T..A..AC....C..T..... |
| AB020549-1/TOC1-93-J | .....A..T..G.TA.ATTTAGAA..A..T.....A..A.....A.TCT. |
| AB020551-1/TOC2-93-J | ..G......TCGGTC.ATTT.GAG.....T..A..AC..G.C..T..... |
| AB020552-1/IZ10-94-J | ..A......T.GGTC.ATTT.GAG.....T..A..AC....C..T..... |
| AB020563-1/MH22-82-J | .....AG....TCTC.ATTTAGAA..A..T..A..AA.A..C..T...T. |
| AB028244/NLV36 | .....AG.G..TCTT.ATTT.GAA........A..AA.A..C..T...T. |
| AB028245/NLV21 | .....AG.C..TCTT.ATTT.GAA........A..AA.A..C..T...T. |
| AB028246/NLV114 | .....AT.T..G.TAGATCTAGAG..A........A.....C.....C.. |
| | **.**..*.................*.**.**...........**.*...* |

Fig. 5B

| | | | |
|---|---|---|---|
| AF145896/Camberwell | 5351 | TTCTCACTTGTCCAGAATGTATAATGGTTATGCAGGTGGTTTTGAAGTGC | 5400 |
| X86557/Lorsdale | | ......T..............C............................ | |
| X81879-2/Melksham | | GG.A..T..AG.A...........C..G.....C.....GA.G..G.... | |
| U07611-2/Hawaii | | AG.A...C.T..A......................C..C..GG......... | |
| U02030-2/Toronto(TV24) | | GG....TC.CG.T........G.................A.......... | |
| L23830-2/OTH-25/89/J | | GG....TC.TG.T........C.................G.......... | |
| AF190817-2/Arg320 | | GG.C..TC.TG.T..........................A.......... | |
| X76716-1/Bristol | | ......T..............C............................ | |
| U22498-2/MX | | GG....TC.TG.T........C.................A.......... | |
| #U1/AB039775 | | AG.A...C.T..T..........................GG....G.... | |
| #U3/AB039776 | | GAG...T......CCC.....C..C..A.....T.....CA.GC.G..T. | |
| #U4/AB039777 | | GAG...T......CCC.....C..C..A.....T.....CA.GC.G..T. | |
| #U16/AB039778 | | GAG...T..A...C.C.................T.....CA.GC.G..T. | |
| #U17/AB039779 | | GAG...T..A...C.C.................T.....CA.GC.G..T. | |
| #U18/AB039781 | | GG....TC.TG.T........C.................A.......... | |
| #U25/AB039780 | | .C.....C.TG.AC.C...........GC...........A.G..G.... | |
| #U201/AB039782 | | GG....TC.TG.T........C.................A.......... | |
| #17 | | GG.A..T | |
| #19a | | GG.C..TC.TG.T | |
| #19f | | GCTCT | |
| #82 | | AG.C..T..AG.A... | |
| #83 | | AG.C.. | |
| #84a | | GG.A..G..AG | |
| #84b | | AG.C..T..AG | |
| #89 | | GG.A..T..AG.A.. | |
| #105e | | C...TGGC | |
| #105d | | ..........G. | |
| #16 | | AG.A...C | |
| #101 | | GG...TT..AG. | |
| #105a | | GAG...T..A... | |
| #105b | | ......T...G.. | |
| #105c | | ......T...G.. | |
| #111b | | . | |
| #18 | | GG....TC.TG.T | |
| #19b | | GG....TC.TG.T | |
| #19c | | GG....TC.TG.T | |
| #19d | | GG.C..TC.TG.T | |
| #19e | | GG....TC.TG.T | |
| #26 | | GG....TC.TG.T | |
| #27b | | GG....TC.TG.T | |
| #31 | | GG.A...C. | |
| #32 | | GG.A...C. | |
| #34 | | .G.....C.TG.A | |
| #35 | | GG.A...C.T | |
| #36 | | GG.A...C | |
| #37a | | GG.A...C.A..T | |
| #37b | | GG.A...C.A..T | |
| #37c | | GG.A...C.A..T | |
| #53b | | GG.C..T | |
| #62 | | GAG...T.. | |
| #63 | | GAG...T.. | |
| #66 | | GAG...T.. | |
| #68 | | GG.A..T.. | |
| #80a | | AG.C..T..AG.A | |
| #80b | | AG.C..T..AG.A | |
| #80c | | GAG...T..A... | |
| #80d | | AG.C..T..AG.A | |
| #109 | | | |
| #80e | | ......T...G.. | |
| #80f | | GAG...T..A... | |
| #85 | | GG.A..T..AG.A | |
| #88 | | GG.A..T..AG.A | |
| #9 | | GG....TC.TG.T | |
| #49 | | GG.C..TC.TG.T | |
| #93 | | GG.A..T..AG.A | |
| #98 | | GG.A..T..AG.A | |
| #99 | | GG.A..T..AG.A | |
| #27a | | GG.C..TC.TG.T | |

Fig. 5B(Continuation)

```
#53a                              GG. C.. TC. TG. T
#111a                             GG. C.. TC. TG. T
046039 Auckland                   GG..... C. TG. T.........C..............A........
U75682-1/Snow Mountain strain     GG. A. T.. AG. A........C.. C.. G......C.....GA. G.. G....
AB032758 Chitta virus             AG. A... C. T.. T.....................GG.....G....
AF080549-1/1996/SC                .......T... G..........C.........................
AF080550-1/345-2/96002737/1996/   .......T... G..........C.........................
AF080551-1/004/95M-14/1995/AU     .......T... G..........C.........................
AF080552-1/358/96015107/1996/FL   .......T.. G..........C.........................
AF080553-1/364/96019537/1996/AZ   .......T... G..........C.........................
AF080554-1/366/96019554/1996/ID   .......T... G..........C.........................
AF080555-1/373/96019743/1996/SC   .......T... G..........C.........................
AF080556-1/379/96019984/1996/AZ   .......T... G..........C.........................
AF080557-1/384/96025046/1996/FL   .......T... G..........C.........................
AF080558-1/408/97003012/1996/FL   ........... G..........................
AF080559-1/416/97003155/1996/LA   ... C.. T... G..........C.........................
AF195847-1/Alphatron/98-2/1998/   GGA..... C. C.. AC. C..... C... TCA.....T.......A. A.. T.. TA
AF195848-1/Amsterdam/98-18/1998   . G..... C. TG. AC. C............GC.....T......A. G.. G....
AJ004864-1/Grimsby                .......T... G..........C.........................
HCA277606/Girlington/93/UK        AG. A.... C. T.. A.. G.... W.............T.....GG......A...
HCA277607/Hillingdon/90/UK        GG. A.. T.. AG. T.. G.....C............G......A. G.. G....
HCA277608/Leeds/90/UK             . G..... T... G. TC. T...........AC. C.. T.....CA. G.......
HCA277611/Bham32/95/UK            GG..... TC. TG. T........C..............A..........
HCA277613/Parkroyal/95/UK         .......T... G..........C.........................
HCA277617/Rbh/93/UK               GG..... TC. TG. T........C..............A..........
HCA277618/Wortley/90/UK           GG. A... C. T.. T. A...................GG.....G....
HCA277619/Symgreen/95/uk          .......T... G..........C.................C..........
HCA277620/Seacroft/90/UK          GAG... T......C. C.....C.. C.. A....T.....CA. GC. G.. T.
U70059-1/Snow Mountain strain     GG. A.. T.. AG. A.......C.. C.. G......C.....GA. G.. G....
AB005260-1/SA1/89/Japan           GG..... C. TG. T..........................C.. G..........
AB005261-1//SA2/91/Japan          GG..... C. TG. T.. G......C..............A..........
AB020547-1/TOB-93-Japan           GG. A.. T.. AG. T.. G.....C............G......A. G.. G....
AB020549-1/TOC1-93-J              AG. A.... C. T.. A.. G....C.............T. C... GG........
AB020551-1/TOC2-93-J              GG. A.. T.. AG. T.. G.....C............G......A. G.. G....
AB020552-1/IZ1G-94-J              GG. A.. T.. AG. T.. G.....C............G......A. G........
AB020553-1/WH22-82-J              GG..... C. TG. T.. G......C...................G.....G....
AB028244/NLV36                    GG. C.. TC. TG. T........................A..........
AB028245/NLV21                    GC. C.. TC. TG. T........................A..........
AB028246/NLV114                   . G..... C. TG. AC. C............GC...........A. G.. G....
                                  ....##.. #.. #.... ####..##......#. ##.##. ##.. #.. #.. #.
```

Fig. 5C

| | | | |
|---|---|---|---|
| AF145896/Camberwell | 5401 | AAGTCATCCTTGCGGCGGAACGCGTTCACCGCCCGGAAAGTTATATTTGCA | 5450 |
| X86557/Lorsdale | | ....A.....C........T....................C......... | |
| X81879-2/Melksham | | .G..C..GT.G..T..............A.....C...T.GG.C..C..C | |
| U07611-2/Hawaii | | .G..AC.A..C..T..............A..G..A...C.GG.G...... | |
| U02030-2/Toronto(TV24) | | .....G....A..T..A..T.....T..A..A..A..GA....C...... | |
| L23830-2/OTH-25/89/J | | .....G....G..T..A..T.....T..A..A.CA..G..G..C...... | |
| AF190817-2/Arg320 | | .G..AG....G..T.....T.....T..A..A..A..GA.A..C...... | |
| X76716-1/Bristol | | ....A.....C.............................C......... | |
| U22498-2/MX | | .....G....G..T..A..T.....T..A..A.CA...A....C...... | |
| #U1/AB039775 | | ....AC.A..G..T.....T........A..T..A...T.GG.G.....G | |
| #U3/AB039776 | | .G...G....A..T.....T........A..T......A.C..C.....C | |
| #U4/AB039777 | | .C...C....A..T.....T........A..T......A.C..C.....C | |
| #U16/AB039778 | | .G...G....A..T..............A..T..T...A.C..C.....C | |
| #U17/AB039779 | | .G...G....A..T..............A..T..T...A.C..C.....C | |
| #U18/AB039781 | | .....G....A..T..A..T.....T..G..A..A..G.....C...... | |
| #U25/AB039780 | | .GA.AG.G.....T.....T........A..G..C...A.CC.G...... | |
| #U201/AB039782 | | .....G....A..T..A..T.....T..A..A..A..G.....C...... | |
| #17 | | | |
| #19a | | | |
| #19f | | | |
| #82 | | | |
| #83 | | | |
| #84a | | | |
| #84b | | | |
| #89 | | | |
| #105e | | | |
| #105d | | | |
| #16 | | | |
| #101 | | | |
| #105a | | | |
| #105b | | | |
| #105c | | | |
| #111b | | | |
| #18 | | | |
| #19b | | | |
| #19c | | | |
| #19d | | | |
| #19e | | | |
| #26 | | | |
| #27b | | | |
| #31 | | | |
| #32 | | | |
| #34 | | | |
| #35 | | | |
| #36 | | | |
| #37a | | | |
| #37b | | | |
| #37c | | | |
| #53b | | | |
| #62 | | | |
| #63 | | | |
| #66 | | | |
| #68 | | | |
| #80a | | | |
| #80b | | | |
| #80c | | | |
| #80d | | | |
| #109 | | | |
| #80e | | | |
| #80f | | | |
| #85 | | | |
| #88 | | | |
| #9 | | | |
| #49 | | | |
| #93 | | | |
| #98 | | | |
| #99 | | | |
| #27a | | | |

Fig. 5C(Continuation)

| | |
|---|---|
| #53a | |
| #111a | |
| U46039 Auckland | .....G....A..T..A..T.....T..A..A..A..G.....C...... |
| U75682-1/Snow Mountain strain | .G..C..G..A..T..............A..T..C...T.GG.C..C..T |
| AB082758 Chitta virus | ....AC.A..G..T.....T........A..T..A...T.GG.G.....C |
| AF080549-1/1996/SC | .G..A.....C..........................A.C......... |
| AF080550-1/345-2/96002737/1996/ | .G..A.....C..........................A.C......... |
| AF080551-1/004/95M-14/1995/AU | .G..A.....C..........................A.C......... |
| AF080552-1/358/96015107/1996/FL | .G..A.....C..........................A.C......... |
| AF080553-1/364/96019537/1996/AZ | .G..A.....C..........................A.C......... |
| AF080554-1/368/96019554/1996/ID | ....A.....C..........................A.C......... |
| AF080555-1/373/96019743/1996/SC | .G..A.....C..........................A.C......... |
| AF080556-1/379/96019984/1996/AZ | .G..A.....C..........................A.C......... |
| AF080557-1/384/96025046/1996/FL | .G..A.....C..........................A.C......... |
| AF080558-1/408/97003012/1996/FL | .G..A.....C..........................A.C......... |
| AF080559-1/416/97003156/1996/LA | .G..A.....C..........................A.C......... |
| AF195847-1/Alphatron/98-2/1998/ | TG...G.GT.G.....T.....C.....A.....T..G...C..A.A... |
| AF195848-1/Amsterdam/98-18/1998 | .GA.AG.G.....T.....T........A..G..C...A.CC.G...... |
| AJ004864-1/Grimsby | .G..A.....C..........................A.C......... |
| HCA277606/Girlington/93/UK | .G...C.A.....T...............A..A..A...C.AC.G...... |
| HCA277607/Hillingdon/90/UK | .......G.....................T..T..C..GA.C..C.....C |
| HCA277608/Leeds/90/UK | ..A.TG.GT.G..T.....T........A..T..C..GA.CG.......T |
| HCA277611/Bham132/95/UK | .....G....A..T..A..T...C.T..A..A..A..G.G...C...... |
| HCA277613/Parkroyal/95/UK | .G..A.....C..........................A.C......... |
| HCA277617/Bbh/93/UK | .....G....A..T..A..T.....T..A..A..A..G.....C...... |
| HCA277618/Wortley/90/UK | ....AC.A..G..T...W..........A..T..A...T.GG.G..C..C |
| HCA277619/Symgreen/95/uk | .G..AG....C.....A.....................A.C......... |
| HCA277620/Seacroft/90/UK | .G...G....A..T.....T....K...A..T......A.C..C.....C |
| U70059-1/Snow Mountain strain | .G..C..G..A..T..............A..T..C...T.GG.C..C..T |
| AB005260-1/SA1/89/Japan | .G..AG....G..T..T..T........A..A..A..GA.A..C...... |
| AB005261-1//SA2/91/Japan | .G..AG....G..T..A..T.....T..A..A..A..G..G..C...... |
| AB020547-1/TOB-93-Japan | ...A...G..C..................T..T..C..GA.C..C.....C |
| AB020549-1/TOC1-93-J | .G...C.A.....T...............A..A..A...C.AG.G...... |
| AB020551-1/TOC2-93-J | .......G..C..................T..T..C..G..C..C.....C |
| AB020552-1/IZ10-94-J | .......G..C..................T..T..C..GA.C..C.....C |
| AB020553-1/MH22-82-J | .G..AG....G..T..A..T.....T..A..A..A..G..G..C...... |
| AB028244/NLV86 | .G...G....G..T.....T........A..A..A..GA.A..C...... |
| AB028245/NLV21 | .G...G....G..T.....T........A..A..A..GA.A..C...... |
| AB028246/NLV114 | .GA.AG.G.....T.....T........A..G..C...A.CC.G...... |
| | ......*..*.**.**..*.**....**.**.*..**.....*..*.**. |

METHOD OF DETECTING NORWALK-LIKE VIRUS (GII)

TECHNICAL FIELD

The present invention relates to a method of detecting a virus.

BACKGROUND ART

The term "food poisoning" generally brings to mind bacterial food poisoning caused by bacteria such as *Salmonella, Vibrio parahaemolyticus*, and pathogenic *E. coli*, or natural toxin food poisoning caused by natural toxins contained in, for example, globefish or mushrooms. In addition, a very large number of food poisoning cases are caused by viruses, such as Norwalk-like viruses (hereinafter referred to as NLVs), rotavirus, astrovirus, enterovirus, adenovirus, and hepatitis A virus. Recent epidemiological research has revealed that, among other viruses, Norwalk-like viruses are typical food-poisoning viruses.

Norwalk virus was first identified in 1972 after an outbreak of gastrointestinal illness in the U.S.A. Under an electron microscope, the virus is observed as a small spherical virus of about 30 nm in diameter having an unclear surface structure, and since then viruses having similar shapes have been collectively called "small round structured viruses" (SRSVs). In the meantime, in 1974, calicivirus, which had been well known in veterinary medicine and which measures about 30 nm in diameter and assumes a unique surface structure resembling a "Star of David," was first identified in a human patient; specifically, in a patient suffering winter vomiting disease, which was at that time epidemic in Britain. Since then, viruses having a shape similar to the above have been called classical human caliciviruses.

These viruses are very difficult to grow in tissue culture cells or in experimental animals, and therefore, for some time the only feasible method was to isolate and culture the viruses on volunteers by use of stool specimens. Thus, characterization of the viruses was quite difficult. In 1990, a research group led by X. Jiang cloned the genome of Norwalk virus, and since then, gene analysis of these viruses has been energetically performed. Such efforts have revealed that an SRSV and a classical human calicivirus both belong to the family of Caliciviridae, having a single stranded "plus" RNA (plus-stranded). In the XIth International Congress of Virology, the family Caliciviridae was reported to comprise four different genera.

Thus, a group of viruses that had been called SRSVs was determined to belong to the genus Norwalk-like viruses (NLVs), and another group that had been called classical human caliciviruses was determined to belong to the genus Sapporo-like viruses (SLVs). Moreover, from an accumulation of data of genomic nucleotide sequences of viruses collected from a vast number of clinical specimens, NLVs have been confirmed to be classified into two genogroups I and II; i.e., genogroup I (GI) encompassing Norwalk viruses and Southampton viruses, and similar viruses; and genogroup II (GII) encompassing Hawaii viruses, Snow Mountain viruses, and similar viruses.

NLV infections in humans primarily occur by the mediation of foods (fish, shellfish, and water). Most of the viral food-poisoning cases that frequently occur during winter are believed to be caused by ingestion of shellfish such as oysters, and in fact, in a great number of study reports, oysters are identified as the source of infection with NLtVs.

Some reports describe that ingestion of a sandwich contaminated with NLVs caused infection. Thus, presumably, NLV infection readily spreads through feces from an infected patient. (This virus is known to have strong infectivity and to cause infection even in a case where several to about one hundred viruses are present in a food product).

Once food poisoning has occurred, needless to say, identification of the cause and the contamination source is a critical issue. That is, the food-poisoning patients must be treated as quickly as possible through appropriate selection of a therapeutic method, which would be realized by identifying the cause of the food poisoning, and simultaneously, spreading of food poisoning must be stopped by identifying the contamination source as early as possible.

In particular, in order to identify the cause and the contamination source of food poisoning caused by pathogenic microorganisms, the following are required: detection and identification of the pathogenic microorganism that caused the illness (i.e., identification of the cause of the food poisoning); and identification of the food and the food manufacturing facility that caused the food poisoning, on the basis of, for example, the diet history of the patient suffering food poisoning (identification of the contamination source of the food poisoning).

Conventionally, an electron microscope has been employed to detect the above-mentioned NLVs. However, methods employing an electron microscope require an intricate procedure, and in addition, rapid and accurate detection of viruses is difficult in cases where the quantity of the viruses is small. In particular, since a very small amount of NLV particles exhibit infectivity, rapid and accurate detection of NLVs in, for example, contaminated foods is keenly desired, and yet, realization has been difficult Moreover, detection methods employing an electron microscope require a large facility for accommodating the electron microscope, and thus, detection through electron microscopy has been possible in only a limited number of facilities.

By keeping pace with the recent progress in gene analysis techniques, more sensitive, more rapid gene analysis through RT-PCR has now been performed frequently. In order to detect a virus through use of this method, primers for amplifying a specific region of the gene (hereinafter referred to as gene amplification primers) and primers used in the process of detecting a gene amplification product of interest on the basis of the presence of the specific region serving as an index (hereinafter referred to as detection primers) must be designed and employed. Particularly in the case of viruses such as NLVs, design of such primers encounters a problem which is very difficult to solve. That is, viruses easily undergo mutation and therefore, even in the case in which the virus responsible for the previous outbreak of food poisoning falls within the same group of the virus that is now epidemic, there is a high risk that detection may be disabled unless primers different from those employed for detection of the virus in previous outbreaks are used for the current food poisoning. Needless to say, attaining accurate identification of the source of contamination will still require use of detection primers each individually specific to viral mutation variants. However, this would only be required for the purpose of verification and would suffice if performed after identification of the causative virus of the food poisoning and identification of the source of infection is almost complete. More importantly, rapid identification should be given a high priority so as to establish a therapeutic regimen for the food-poisoning patient and to prevent spreading of contamination.

In order to solve the above problem, a need exists for discovering a highly conserved region in genes of a virus of interest, and designing, among other things, detection primers which correspond to the region, thus providing means for detecting the virus through use of such tools.

Accordingly, an object of the present invention is to identify a highly conserved region in genes of NLVS, and, on the basis of the information thus obtained, to provide rapid, accurate means for detecting NLVs.

DISCLOSURE OF THE INVENTION

In order to attain the above object, the present inventors have conducted careful studies and have successfully identified a highly conserved region (bridging the vicinity of the C-terminus of the ORP 1 region and the vicinity of the N-terminus of the ORF 2 region) in a gene of NLV genogroup II, and, on the basis of this finding, have devised rapid, accurate means for detecting viruses belonging to genogroup II of NLVS, among other NLVs, leading to completion of the present invention.

First, there will be described an essential discovery that constitutes the basis for the present invention; i.e., a highly conserved region commonly found in genes of Norwalk-like viruses (NLVs) belonging to genogroup II (hereinafter also referred to as NLVs (GII)).

In order to identify the above-mentioned highly conserved region in the gene of an NLV (GII), the present inventors performed the following test.

Details of the Test (1) Stool Specimens and Preparation of RNA Samples

Gene analysis of NLVs (GII) was performed on stool specimens collected from 44 cases of non-bacterial gastroenteritis from which NLV particles were detected through electron microscopy in the Saitama Institute of Public Health during 1998-2000.

Briefly, each of the stool specimens was suspended in sterilized distilled water so as to attain a concentration of about 10% (W/V), and the suspension was subjected to centrifugation at 3000×g for 5 minutes. From the supernatant (140 μL), nucleic acid was extracted in accordance with the manufacturer's protocol of an RNA extraction kit (QIA Viral RNA, Qiagen), and suspended in 50 μL sterilized distilled water, whereby an RNA sample was obtained.

(2) Determination of Full Length Sequences of NLV Genes and Analysis of the Genes cDNA was synthesized from each of the thus-prepared RNA samples by use of an oligo dT primer, and amplified through LongRT-PCR. The nucleotide sequence of each of the gene amplification products was determined through direct sequencing by use of the primer walking method (Nucleic Acids Res. 1989 17(15):6087-6102). Sequencing of the genomic 5'-terminus was performed using three types of RACE (rapid amplification of cDNA ends).

Through the gene analysis employing the above RNA samples, the entire nucleotide sequences of 8 new NLV strains (#U1/AB039775, #U3/AB039776, #U4/AB039777, #U16/AB039778, #U17/AB039779, #U18/AB039781, #U25/AB039780, #U201/AB039782) were determined, and partial nucleotide sequences (53 sequences) of 33 strains were also determined (#17, #19a, #19b, #19c, #19d, #19f, #19e, #82, #83, #84a, #84b, #89, #105a, #105b, #105c, #105d, #105e, #16, #101, #111a, #111b, #18, #26, #27a, #27b, #31, #32, #34, #35, #36, #37a, #37b, #37c, #53a, #53b, #62, #63, #66, #68, #80a, #80b, #80c, #80d, #80e, #80f, #109, #85, #88, #9, #49, #93, #98, #99). Genome diversity was investigated by use of the nucleotide sequences of a number of NLV variants, including these new variants, a prototype (standard strain; AF145896/Camberwell), and known NLV (GII) variants which had already been registered in Genbank (X86557/Lorsdale, X81879-2/melksham, U07611-2/Hawaii, U02030-2/Tronto(TV24), L23830-2/OTH-25/89/J, AF190817-2/Arg320, X76716-1/Bristol, U22498-2/MK, U46039 Auckland, U75682-1/Snow Mountain Strain, AB032758 Chitta virus, AF080549-1/1996/SC, AF080550-1/345-2/96002737/1996/, AF080551-1/004/95M-14/1995/AU,AF080552-1/358/96015107/1996/FL, AF080553-1/364/96019537/1996/AZ, AF080554-1/366/96019554/1996/ID, AF080555-1/373/96019743/1996/SC, AF080556-1/379/96019984/1996/AZ, AF080557-1/384/96025046/1996/FL, AF080558-1/408/97003012/1996/FL, AF080559-1/416/97003156/1996/LA, AF195847-1/Alphatron/98-2/1998/, AF195848-1/Amsterdam/98-18/1998, AJ004864-1/Grimsby, HCA277606/Girlington/93/UK,HCA277607/Hillingdon/90/UK, HCA277608/Leeds/90/UK, HCA277611/Bhaml32/95/UK, HCA277613/Parkroyal/95/UK, HCA277617/Rbh/93/UK, HCA277618/Wortley/90/UK, HCA277619/Symgreen/95/UK, HCA277620/Seacroft/90/UK, 070059-1/Snow Mountain strain, AB005260-1/SA1/89/Japan, AB005261-1/SA2/91/Japan, AB020547-1/TOB-93-Japan, AB020549-1/TOC1-93-J, AB020551-1/TOC2-93-J,AB020552-1/IZ10-94-J, AB020563-1/MH22-82-J, AB028244/NLV36, AB028245/NLV21, AB028246/NLV114), and the most highly conserved gene region was searched.

In the present invention, the reference employed as a basis for describing a gene region is the nucleotide sequence (cDNA sequence) of a gene of the above-mentioned prototype (standard strain), AF145896/Camberwell. FIG. 1 shows the results of the investigation of genome diversity. In chart i) of FIG. 1, the X-axis represents the base number—as counted from the 5'-terminus—of the gene (cDNA) of the above-mentioned prototype of NVLs (GII), and the Y-axis represents the degree of conservation (the greater the Y-axis value, the more analogous the nucleotide sequences of respective strains, meaning that the gene is highly conserved, and conversely, the smaller the Y-axis value, the more varied the nucleotide sequences of respective strains, meaning that the gene is less conserved). Chart ii) of FIG. 1 shows functions, in NLVs (GII), of the gene having the above-described nucleotide sequences.

Analysis of the genes of NLVs (GII) shown in FIG. 1 revealed that the region in which the genes from respective strains exhibit the highest homology lies between the vicinity of the C-terminus of the ORF1 region and the vicinity of the N-terminus of the ORF2 region, where the maximum value of homology was found to be 90% or more.

FIGS. 2 to 5 show, in an orderly arranged form for the purpose of comparison, nucleotide sequences of the respective strains of NLVs (GII), spanning from the vicinity of the C-terminus of ORF1 (FIGS. 2A to 2C) to the vicinity of the N-terminus of ORF2 (FIGS. 4A and 4D, and 5A to 5C; Note that FIGS. 3A to 3C show nucleotide sequences of a region that bridges ORF1 and ORF2). In FIGS. 2 to 5, the names of the respective strains of NLVs (GII) employed are shown in the left column, and the nucleotide sequence of the prototype (standard strain) is shown in the uppermost row, As described hereinabove, in the present invention, the base number of the prototype shown in the uppermost row is employed as a reference. In the nucleotide sequences of respective strains (excepting the prototype), the symbol "." represents that the base at that position is the same as that of the prototype (standard strain), and the vacancies indicate that the bases found at the corresponding positions in the prototype are absent. The symbol "*" in the lowermost row indicates that the base at that position is in common throughout the strains, and the symbol "." in the lowermost row indicates the presence of any difference in base among the strains.

(3) Conclusion

The investigation on gene conservation of NLVs (GII) has clarified that the nucleotide sequence region exhibiting gene conservation of such a degree that enables use of that region in detection of NLVs (GII) is a region corresponding to the 4851- to 5450-positions of the nucleotide sequence of the cDNA of the prototype (standard strain) of NLVs (GII); that a region corresponding to the 4919- to 5389-positions of the nucleotide sequence exhibits a particularly high level of conservation, and a region corresponding to the 4988- to 5107-positions of the nucleotide sequence exhibits an exceptionally high conservation (in particular, a region corresponding to the 5042- to 5067-positions exhibits the highest conservation (hereinafter this region may be referred to as the significantly highly conserved region). [Within this context, the expression "corresponding to" is used to describe a relation between two corresponding nucleotide sequence regions, one being from the cDNA of the above-mentioned prototype and the other being from a variant, which relation is elucidated through gene analysis of NLVs (GII), including variants. Specific examples include nucleotide sequences of NLVs (GII) shown in FIGS. 2 to 5, which correspond to the gene region represented by the above-mentioned nucleotide sequence of the cDNA of the prototype.]

The present invention is directed to means for rapidly and accurately detecting NLVs (GII) by making use of the nucleotide sequence of a nucleic acid in a highly conserved gene region (i.e., the region corresponding to the 4851- to 5450-positions of the nucleotide sequence of the cDNA of the prototype (standard strain) of NLVs (GII), hereinafter such a gene region is also referred to as a "conserved region"), which is determined through gene analysis regarding gene conservation of NLVs (GII). Specifically, the present invention provides a viral detection method for Norwalk-like viruses (GII) in a specimen (hereinafter also referred to as "the present detection method") by use of, as an index, the nucleic acid fragment of a complementary nucleotide sequence or complementary nucleotide sequences (hereinafter collectively called "a complementary nucleotide sequence") corresponding to the 4851- to 5450-positions (preferably 4919- to 5389-positions (hereinafter also referred to as the highly conserved region), more preferably 4988- to 5107-positions (hereinafter also referred to as the special conserved region)) of the nucleotide sequence of the cDNA of the prototype (standard strain) of NLVs (GII).

As used herein, the word "complementary" is used to describe a relation where a nucleic acid fragment having a certain nucleotide sequence exhibits such a degree of complementation that enables hybridization with another nucleic acid fragment under stringent conditions (56 to 68° C., in the presence of 50 mM or more sodium ions), and the expression "complementary nucleotide sequence" encompasses the following incidences: The "complementary nucleotide sequence" is minus-stranded with respect to a plus-stranded fragment of the nucleotide sequence; the "complementary nucleotide sequence" is plus-stranded with respect to a minus-stranded fragment of the nucleotide sequence; and one "complementary nucleotide sequence" is minus-stranded with respect to a plus-stranded fragment of the nucleotide sequence and the other "complementary nucleotide sequence" is plus-stranded with respect to a minus-stranded fragment of the nucleotide sequence.

BRIEF DESCRIPTION OF THE DRAWINGS

FIGS. 2A to 2C show nucleotide sequences identified in respective strains of NLVs (GII), arranged for facilitating comparison, the sequences coding for the vicinity of the C-terminus of the ORF1 region.

FIG. 2A shows the following nucleotide sequences, ordered from top to bottom in the figure: nucleotides 1-50 of SEQ ID NOs:14-40.

FIG. 2B shows the following nucleotide sequences, ordered from top to bottom in the figure: nucleotides 5 1-100 of SEQ ID NOs:14-40, and nucleotides 1-9 of SEQ ID NOs:41-80.

FIG. 2C shows the following nucleotide sequences, ordered from top to bottom in the figure: nucleotides 101-150 of SEQ ID NOs:14-40, and nucleotides 10-59 of SEQ ID NOs:41-80.

FIGS. 3A to 3C show nucleotide sequences identified in respective strains of NLVs (GII), arranged for facilitating comparison, the sequences coding for the region from the vicinity of the C-terminus of the ORF1 region to the vicinity of the N-terminus of the ORF2 region.

FIG. 3A shows the following nucleotide sequences, ordered from top to bottom in the figure: nucleotides 151-200 of SEQ ID NOs:14-40, nucleotides 60-109 of SEQ ID NOs:41-80, and nucleotides 1-3 of SEQ ID NO:84.

FIG. 3B shows the following nucleotide sequences, ordered from top to bottom in the figure: nucleotides 201-250 of SEQ ID NOs:14-40, nucleotides 110-159 of SEQ ID NOs:41-80, nucleotides 1-33 of SEQ ID NOs:81-83, nucleotides 4-53 of SEQ ID NO:84, nucleotides 1-34 of SEQ ID NO:85, and nucleotides 1-16 of SEQ ID NOs:86-110.

FIG. 3C shows the following nucleotide sequences, ordered from top to bottom in the figure: nucleotides 251-300 of SEQ ID NOs:14-40, nucleotides 160-209 of SEQ ID NOs:41-80, nucleotides 34-83 of SEQ ID NOs:81-83, nucleotides 54-103 of SEQ ID NO:84, nucleotides 35-84 of SEQ ID NO:85, nucleotides 17-66 of SEQ ID NOs:86-110, nucleotides 1-45 of SEQ ID NOs:111-117, and nucleotides 1-43 of SEQ ID NOs:118-120.

FIGS. 4A to 4C show nucleotide sequences identified in respective strains of NLVs (GII), arranged for facilitating comparison, the sequences coding for the vicinity of the N-terminus of the ORF2 region (part 1 of 2).

FIG. 4A shows the following nucleotide sequences, ordered from top to bottom in the figure: nucleotides 301-350 of SEQ ID NOs:14-40, nucleotides 210-259 of SEQ ID NOs:41-80, nucleotides 84-133 of SEQ ID NOs:81-83, nucleotides 104-153 of SEQ ID NO:84, nucleotides 85-134 of SEQ ID NO:85, nucleotides 67-116 of SEQ ID NOs:86-110, nucleotides 46-95 of SEQ ID NOs:111-117, and nucleotides 44-93 of SEQ ID NOs:118-120.

FIG. 4B shows the following nucleotide sequences, ordered from top to bottom in the figure: nucleotides 351-400 of SEQ ID NOs:14-40, nucleotides 260-309 of SEQ ID NOs:41-80, nucleotides 134-183 of SEQ ID NOs:81-83, nucleotides 154-203 of SEQ ID NO:84, nucleotides 135-184 of SEQ ID NO:85, nucleotides 117-166 of SEQ ID NOs:

Figure 1:
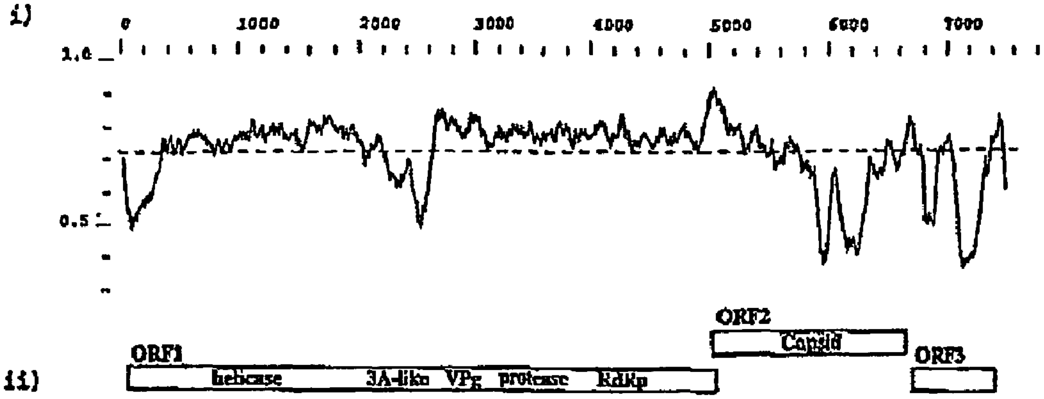
FIG. 1 shows the results of the investigation of genome diversity of NLVs (GII).

86-110, nucleotides 96-145 of SEQ ID NOs:111-117, and nucleotides 94-143 of SEQ ID NOs:118-120.

FIG. 4C shows the following nucleotide sequences, ordered from top to bottom in the figure: nucleotides 401-450 of SEQ ID NOs:14-40, nucleotides 310-359 of SEQ ID NOs:41-80, nucleotides 184-233 of SEQ ID NOs:81-83, nucleotides 204-253 of SEQ ID NO:84, nucleotides 185-234 of SEQ ID NO:85, nucleotides 167-216 of SEQ ID NOs: 86-110, nucleotides 146-195 of SEQ ID NOs:111-117, and nucleotides 144-193 of SEQ ID NOs:118-120.

FIGS. 5A to 5C shows nucleotide sequences identified in respective strains of NLVs (GII), arranged for facilitating comparison, the sequences coding for the vicinity of the N-terminus of the ORF2 region (part 2 of 2).

FIG. 5A shows the following nucleotide sequences, ordered from top to bottom in the figure: nucleotides 451-500 of SEQ ID NOs:14-40, nucleotides 360-409 of SEQ ID NOs:41-80, nucleotides 234-283 of SEQ ID NOs:81-83, nucleotides 254-303 of SEQ ID NO:84, nucleotides 235-284 of SEQ ID NO:85, nucleotides 217-266 of SEQ ID NOs: 86-110, nucleotides 196-245 of SEQ ID NOs:111-117, and nucleotides 194-243 of SEQ ID NOs:118-120.

FIG. 5B shows the following nucleotide sequences, ordered from top to bottom in the figure: nucleotides 501-550 of SEQ ID NOs:14-30, nucleotides 501-507 of SEQ ID NO:31, nucleotides 501-513 of SEQ ID NO:32, nucleotides 501-505 of SEQ ID NO:33, nucleotides 501-516 of SEQ ID NO:34, nucleotides 501-506 of SEQ ID NO:35, nucleotides 501-511 of SEQ ID NOs:36-37, nucleotides 501-515 of SEQ ID NO:38, nucleotides 501-508 of SEQ ID NO:39, nucleotides 501-512 of SEQ ID NO:40, nucleotides 410-417 of SEQ ID NO:41, nucleotides 410-421 of SEQ ID NO:42, nucleotides 410-422 of SEQ ID NOs:43-45, nucleotide 410 of SEQ ID NO:46, nucleotides 410-422 of SEQ ID NOs: 47-53, nucleotides 410-418 of SEQ ID NOs:54-55, nucleotides 410-422 of SEQ ID NO:56, nucleotides 410-419 of SEQ ID NO:57, nucleotides 410-419 of SEQ ID NO:57, nucleotides 410-417 of SEQ ID NO:58, nucleotides 410-422 of SEQ ID NOs:59-61, nucleotides 410-416 of SEQ ID NO:62, nucleotides 410-418 of SEQ ID NOs:63-66, nucleotides 410-422 of SEQ ID NOs:67-70, nucleotide 410 of SEQ ID NO:71, nucleotides 410-422 of SEQ ID NOs:72-80, nucleotides 284-296 of SEQ ID NOs:81-83, nucleotides 304-353 of SEQ ID NO:84, nucleotides 285-334 of SEQ ID NO:85, nucleotides 267-316 of SEQ ID NOs:86-110, nucleotides 246-295 of SEQ ID NOs:111-117, and nucleotides 244-293 of SEQ ID NOs:118-120.

FIG. 5C shows the following nucleotide sequences, ordered from top to bottom in the figure: nucleotides 551-600 of SEQ ID NOs:14-30, nucleotides 354-403 of SEQ ID NO:84, nucleotides 335-384 of SEQ ID NO:85, nucleotides 317-366 of SEQ ID NOs:86-110, nucleotides 296-345 of SEQ ID NOs:111-117, and nucleotides 294-343 of SEQ ID NOs:118-120.

BEST MODE FOR CARRYING OUT THE INVENTION

Modes for carrying out the present invention will next be described.

In order to make use of the finding on conserved regions of NLVs (GII) as an index for detecting NLVs (GII), any of the mentioned conserved regions (hereinafter collectively referred to as "Conserved Regions"; including the "highly conserved region," "special conserved region," and "significantly highly conserved region"; the convention applies hereafter) must be amplified through a nucleic acid amplification method, to thereby produce gene amplification products of the Conserved Regions. Examples of such an amplification method include PCR and other methods, such as RT-PCR, NASBA (nucleic acid sequence based amplification), and SDA (strand displacement amplification). In any of these methods, gene amplification primers must be designed and prepared so as to be adapted to the method. Generally, gene amplification primers are designed such that a gene region is amplified in both directions of forward (5'→3') and reverse, with the gene region being sandwiched by +/−primers. Since the gene amplification primers must properly bind to the intended regions of the gene serving as a template for attaining complementary binding, it is necessary that any of such primers contain at least a minimum number of bases forming a nucleotide sequence complementary only to characteristic nucleotide sequence(s). Such a gene amplification primer has at least 10 bases, preferably about 15 to 30 bases. In addition, for 5 bases counted from the 3'-terminus in a region that is to achieve a complementary binding, the primer is preferably designed to be as precisely complementary as possible.

Moreover, the gene region which is employed as a basis for establishing gene amplification primers must at least meet the requirement that the resultant gene amplification product contains a complementary nucleotide sequence corresponding to Conserved Regions. From this viewpoint, a preferred gene amplification primer comprises a complementary nucleotide sequence corresponding to consecutive 10 or more bases, preferably consecutive 15 to 30 bases, of a nucleotide sequence selected, as a benchmark, from the group consisting of nucleotide sequences of the 4988- to 5028-positions of the nucleotide sequence of the cDNA of the prototype (standard strain) of NLVs (GII), the 5080- to 5107-positions thereof, the 4919- to 4941-positions thereof, and the 5367- to 5389-positions thereof.

Nucleic acids having nucleotide sequences that correspond to a conserved region—the nucleic acids serving as indices in detection of NLVs (GII) in the present invention—are obtained as follows: at least two nucleotide sequences having 10 or more consecutive bases (preferably a complementary nucleotide sequence having 15 to 30 bases) are selected from the conserved region; and through use of gene amplification primers established on the basis of the selected nucleotide sequences, genes obtained from specimens are subjected to the above-mentioned amplification means, to thereby yield the target nucleic acids as the gene amplification products. Preferably, the gene amplification products include a region corresponding to the 4942- to 5366-positions of the nucleotide sequence of the cDNA of the prototype of NLVs (GII), which is a highly conserved region within the aforementioned conserved regions. Most preferably, the nucleotide sequence to be included in the gene amplification products obtained from the highly conserved region is a segment corresponding to the 5042- to 5067-positions of the complementary nucleotide sequence of the cDNA of the prototype of NLVs (GII), which is the significantly highly conserved region.

That is, through use of the gene amplification primers of any of the above combinations, the resultant gene amplification products originating from NLVs (GII) will contain at least a nucleotide sequence corresponding to the 5042- to 5067-positions of the nucleotide sequence of the cDNA of the prototype of NLVs (GII). Therefore, through use of Means which enables detection of the nucleotide sequences of the mentioned highly conserved regions, most typically, through use of nucleic acid probes complementary to a complementary nucleotide sequence containing a portion of or the entirety of the highly conserved regions falling within the nucleic acid of the detection target, detection and quantitation of the resultant gene amplification product, which is the target of detection, can be attained, and using the quantitation/detection results as indices, NLVs (GII) can be detected rapidly and accurately.

Notably, in order to obtain a gene amplification product containing a nucleotide sequence of the significantly highly conserved region, the at least two nucleotide sequences based on which gene amplification primers are established, each nucleotide sequence being composed of 10 or more consecutive bases, are preferably selected from the cDNA nucleotide sequence set of 4988- to 5028-positions and 5080- to 5107-positions of the nucleotide sequence of the cDNA of the prototype (standard strain) of Norwalk-like viruses (GII).

Through use of the gene amplification primers falling within the above combinations, the resultant gene amplification products originating from NLVS (GII) will contain a nucleotide sequence corresponding to the 5042- to 5067-positions of the nucleotide sequence of the cDNA of the prototype of NLVs (GII). Therefore, through use of means which enables detection of the nucleotide sequences of the mentioned significantly highly conserved regions, most typically, through use of nucleic acid probes complementary to a complementary nucleotide sequence containing a portion of or the entirety of the significantly highly conserved regions falling within the nucleic acid of the detection target, detection and quantitation of the resultant gene amplification product, which is the target of detection, can be attained, and using the quantitation/detection results as indices, NLVs (GII) can be detected rapidly and accurately.

Each of the above-described gene amplification primers may be employed as a component of the detection kit of the present invention described hereinbelow.

Notably, the present detection method can be applied to any specimen in which NLVS (GII) are to be detected. For example, when NLVs (GII) are to be detected in a food-poisoning patient, stool of the patient is typically employed as a specimen, and depending on the case, vomitus, blood, etc. may be employed. When NLVs (GII) are to be detected in food or a food production facility, the food itself, deposits collected from the food production facility, clothing of food production workers, etc. may be employed as a specimen. Moreover, the specimen may be obtained from watery sources, such as various types of sewage or discharging water, seawater, river water, and lake water. In order to obtain genes from the aforementioned specimens, suitable methods are selected according to the type of the specimen to be employed. Generally, a specimen is immersed or suspended in water or a similar medium, and from a supernatant fraction obtained therefrom, viral RNA is extracted, through a conventional method such as the acid phenol method (e.g., the acid guanidinum-phenol-chloroform (AGPC) method). The thus-obtained viral RNA is processed through a suitably selected gene amplification method. For example, through preparation of cDNA having a nucleotide sequence complementary to the nucleotide sequence of the viral RNA using a reverse transcriptase—to thereby obtain a nucleic acid sample. The nucleic acid sample is then subjected to gene amplification by use of the aforementioned gene amplification primers, whereby a gene amplification product of interest can be obtained (generally, the presence of the product of interest can be confirmed through electrophoresis on the basis of size of the target product).

Conventional means may be employed to detect, as an index of the presence of NLVs (GII), a certain specific nucleotide sequence of a gene amplification product. Typically, through use of nucleic acid probes for detection (for example, nucleic acid fragments which have been labeled with a fluorophore or a radioisotope) containing nucleotide sequences complementary to the aforementioned complementary nucleotide sequence(s) that serve(s) as an index of virus detection, the presence or absence of the nucleotide sequence of the gene amplification product can be confirmed by hybridization or a similar method (as a negative result or positive result). Generally, such detection means is performed on the amplification product after the gene amplification process has completed. However, such a procedure involves a drawback in that since a technician must open a tube to remove the analytical sample after gene amplification reaction, there will be increased chances where experimental facilities or reagents may be polluted with the gene amplification product, and in addition, extra time and labor may be required. Moreover, the polluting gene amplification product may invite the risk of false positive results, raising critical problems in the field of detection. Accordingly, in order to avoid risks such as pollution and to minimize the time required for detection, it is recommended to use, during gene amplification, means enabling monitoring of the presence of a specific nucleotide sequence of the gene amplification product. Examples of typical methods employing such means include, but are not limited to, 1) a detection method by use of a molecular beacon probe, and 2) a detection method by use of a Taq-Man probe.

1) The detection method by use of a molecular beacon probe makes use of a hair-pin shaped hybridization probe (molecular beacon probe) for allowing fluorescent monitoring of a gene amplification product obtained by PCR during or after an amplification procedure (Nature Biotechnology, 1998, 16: 49-53). Terminal sequences of the nucleic acid fragment constituting the molecular beacon probe are complementary to each other. Typically, the terminal portions are bonded to each other, whereby a “stem-loop structure” is formed. The loop portion of the stem-loop structure is designed so as to be complementary to a region of interest (i. ., Conserved Regions) of the gene amplification product. Moreover, to one end of the nucleic acid of the probe, a fluorophore is bound, and to the other end of the nucleic acid of the probe, a non-fluorescent quencher dye is bound. When the probe is present in a solution in a free state, the probe has a hairpin structure, whereby the fluorophore and the quencher interact each other, and fluorescence is not detected. However, when the solution contains the gene amplification product having a nucleotide sequence complementary to the nucleotide sequence of the probe, the loop portion is bound to the complementary nucleotide sequence portion. As a result, the overall structure of the probe varies, resulting in a separation of the fluorophore and the quencher from each other, and thus quenching effect of the quencher for the fluorophore is canceled. Therefore, fluorescence emitted from the fluorophore can be observed. Increase in fluorescence intensity caused by canceling of the quenching effect is proportional to the increment in the amount of the gene amplification product having the nucleotide sequence complementary to the sequence of the nucleic acid that forms the probe. Through monitoring the increase in the fluorescence intensity, the presence of the target nucleotide sequences (e.g., sequences of Conserved Regions) can be detected not only after completion of gene amplification, but also during gene amplification. That is, NLVs (GII) in a specimen can be detected through use of the results of the aforementioned increase in fluorescence intensity as an index.

Labeling of a molecular beacon probe through use of the aforementioned fluorophore and the quencher is typically performed as follows. The 5'-terminus of the nucleic acid probe is labeled with a fluorescein fluorophore (such as 6-carboxyfluorescein (6-FAM) or 6-carboxy-4,7,2',7'-tetrachlorofluorescein (TET)) or a rhodamine fluorophore (such as 5-carboxytetramethylrhodamine (TAMARA)), and the 3'-terminus of the probe is labeled with a quencher (such as 4-(4'-dimethylaminophenylazo)benzoic acid (DABCYL)) (see, for example, Nature Biotechnology, 1996, 14: 303-308).

2) The detection method by use of a Taq-Man probe makes use of a hybridization probe (Taq-Man probe) for allowing fluorescent monitoring of a gene amplification product obtained by PCR during the amplification procedure (see, for example, Experimental Medicine, Vol. 15, No. 7 (extra issue), pp. 46-51, 1997). The Taq-Man probe is a nucleic acid fragment bearing a fluorescein fluorophore label (reporter dye) and a rhodamine fluorophore label (quencher dye) at the 5'-terminus and 3'-terminus of the fragment, respectively. When the reporter dye and the quencher dye are linked to each other via the nucleic acid fragment, due to Forster resonance energy, the quencher dye inhibits fluorescence emission of the reporter dye. However, as elongation proceeds along with the progress of annealing of a nucleic acid (in the gene amplification product) which is complementary to the nucleic acid of the Taq-Man probe performed through use of primers and the Taq-Man probe, hydrolysis occurs from the 5'-terminus of the Taq-Man probe under 5'→3' endonuclease activity of Taq DNA polymerase. As a result, the 5'-terminal reporter dye is released from the 3'-terminal quencher dye, resulting in an increase in fluorescence intensity of the reporter dye which has been suppressed. The increase in fluorescence intensity caused by the reporter dye is proportional to the increase in the amount of the gene amplification product having the nucleotide sequence complementary to the sequence of the nucleic acid that forms the probe Through monitoring the increase in fluorescence intensity, the presence of the nucleotide sequence of interest (e.g., Conserved Regions) can be detected not only after completion of gene amplification, but also during gene amplification. Thus, NLVs (GII) in a detection specimen can be detected through use of the results of the aforementioned increase in fluorescence intensity as an index.

Labeling of a Taq-Man probe with the aforementioned fluorophore is typically performed in accordance with a conventional method by labeling the 5'-terminus of the probe with a fluorescein fluorophore (such as 6-FAM or TET), and the 3'-terminus of the probe with a rhodamine fluorophore (such as TAMARA) (see, for example, Nucleic Acids Research, 1993, 21 (16): 3761-3776).

All the aforementioned nucleic acid probes to be used for detection purposes (hereinafter also referred to as nucleic acid probes for detection) may be employed as components of the detection kit of the present invention which will be described below.

In relation to the detection of NLVs (GII) according to the present detection method, detection of a gene amplification product or a similar product having a nucleotide sequence of interest may be performed by way of quantitation of the nucleic acid fragment of interest through use of the aforementioned means. Alternatively, instead of quantitation, NLVs (GII) may be detected in the form of qualitative (e.g., positive or negative) information. By use of the detection results of the gene amplification products (quantitative value or qualitative information) as an index, and by correlating the index to the presence/absence or the amounts of the NLVs (GII) in the specimen, the NLVs (GII) of interest can be detected.

The present invention also provides a kit for detecting NLVs (GII) (hereinafter, the kit will be referred to as the present detection kit) for performing the present detection method.

The present detection kit typically contains primers for amplifying—by RT-PCR or any other suitable method—a nucleic acid fragment having any of Conserved Regions of NLVs (GII), and/or one or more probes for detecting the Conserved Regions of a gene amplification product. Preferably, the kit contains both; primers and probes.

The gene amplification primers are nucleic acid fragments capable of producing gene amplification products through amplification of a Conserved Region of an NLV (GII) gene by use of gene amplification means such as RT-PCR. The nucleic acid probes for detection contain nucleic acid fragments having nucleotide sequences complementary to sequences corresponding to the nucleotide sequences of a Conserved Region. As described above, one may employ nucleic acid probes for detection of a basic mode comprising complementary nucleotide sequences labeled with a fluorophore or a radioisotope. In particular, when NLVs (GII) are detected in the course of gene amplification, preferably, there may be employed such nucleic acid probes for detection produced by incorporating nucleic acids of a complementary nucleotide sequence into the aforementioned molecular beacon probe or Taq-Man probe.

Details of the gene amplification primers and the nucleic acid probes for detection which may be included in the present detection kit have already been described in relation to the present detection method. Specific examples of such primers and probes are also described in the Example section below.

EXAMPLE

The present invention will next be described by way of example, which should not be construed as limiting the technical scope of the invention.

[Preparation of Primers and Probes]

Detection of NLVs (GII) in the present example was performed by use of the following nucleic acid primers for gene amplification and nucleic acid probes for gene detection. The nucleic acids described below were chemically synthesized by use of a full-automated ABI 3948 Nucleic Acid Synthesis and Purification System (Applied Biosystems).

Gene Amplification Primers

[Forward Primers (Used in the Form of a Mixture or Individually]

For amplification of a special conserved region:

G2FA: 5' CARGARBCNATGTTYAGRTGGATGAG 3' (SEQ ID NO; 1, corresponding to the 5003- to 5028-positions of the nucleotide sequence of the prototype)

For amplification of a highly conserved region:

G2FB1: 5' GGHCCMBMDTTYTACAGCAA 3' (SEQ ID NO: 2, corresponding to the 4922- to 4941-positions of the nucleotide sequence of the prototype)

G2FB2: 5' GGHCCMBMDTTYTACAAGAA 3' (SEQ ID NO: 3, corresponding to the 4922- to 4941-positions of the nucleotide sequence of the prototype)

G2FB3: 5' GGHRCCMBMDTTYTACARNAA 3' (SEQ ID NO: 4, corresponding to the 4922- to 4941-positions of the nucleotide sequence of the prototype)

[Reverse Primers (Used in the Form of a Mixture or Individually]

For amplification of a special conserved region:

G2RA1: 5' TCGACGCCATCTTCATTCACA 3' (SEQ ID NO: 5, corresponding to a nucleotide sequence that is complementary to the 5080- to 5100-positions of the nucleotide sequence of the prototype)

G2RA2: 5' TCAYTCGACGCCATCTTCAT 3' (SEQ ID NO: 6, corresponding to a nucleotide sequence that is complementary to the 5085- to 5104-positions of the nucleotide sequence of the prototype)

For amplification of a highly conserved region:

G2RB1: 5' CCACCWGCATAACCATTRTACAT 3' (SEQ ID NO: 7, corresponding to a nucleotide sequence that is complementary to the 5367- to 5389-positions of the nucleotide sequence of the prototype)

G2RB2: 5' CCACCWGCATGCCCATTRTACAT 3' (SEQ ID NO: 8, corresponding to a nucleotide sequence that is complementary to the 5367- to 5389-positions of the nucleotide sequence of the prototype)

G2RB3: 5' CCRCCNGCATRHCCRTTRTACAT 3' (SEQ ID NO: 9, corresponding to a nucleotide sequence that is complementary to the 5367- to 5389-positions of the nucleotide sequence of the prototype)

Nucleic Acid Probes for Gene Detection

[Taq-Man Probes]

G2TM1: 5' TGGGAGGGCGATCGCAATCT 3' (SEQ ID NO: 10, corresponding to the 5048- to 5067-positions of the nucleotide sequence of the prototype)

G2TM2: 5' AGATTGCGATCGCCCTCCCA 3' (SEQ ID NO: 11, corresponding to a nucleotide sequence that is complementary to the 5048- to 5067-positions of the nucleotide sequence of the prototype)

The 5'-terminus and the 3'-terminus of all the Taq-Man probes used in the present example were labeled with TET and TAMARA, respectively (labeling was performed in accordance with the method described in *Nucleic Acids Research* (1993, 21 (16): 3761-3766)).

[Molecular Beacon Probes (the Lowercase Letters Denote Stem Portions)]

G2MB1: 5' ccgtcgTGGGAGGGCGATCGCAATCTcgacgg 3' (SEQ ID NO: 121, corresponding to the 5048- to 5067-positions of the nucleotide sequence of the prototype)

G2MB2: 5' cgtgctGGGAGGGCGATCGCAAgcacg 3' (SEQ ID NO: 12, corresponding to the 5049- to 5064-positions of the nucleotide sequence of the prototype)

G2MB3: 5' ccgtcgAGATTGCGATCGCCCTCCCAcgacgg 3' (SEQ ID NO: 122, corresponding to a nucleotide sequence that is complementary to the 5048- to 5067-positions of the nucleotide sequence of the prototype)

G2MB4: 5' ccgtcgATTGCGATCGCCCTCCCAcgacgg 3' (SEQ ID NO: 123, corresponding to a nucleotide sequence that is complementary to the 5050- to 5067-positions of the nucleotide sequence of the prototype)

G2MB5: 5' ccgtggATTGCGATCGCCCTCCCccacgg 3' (SEQ ID NO: 13, corresponding to a nucleotide sequence that is complementary to the 5048- to 5066-positions of the nucleotide sequence of the prototype)

G2MB6: 5' cgtggaATTGCGATCGCCCTCCCtccacg 3' (SEQ ID NO: 124, corresponding to a nucleotide sequence that is complementary to the 5048- to 5066-positions of the nucleotide sequence of the prototype)

G2MB7: 5' cctgcATTGCGATCGCCCTCCCAgcagg 3' (SEQ ID NO: 125, corresponding to a nucleotide sequence that is complementary to the 5048- to 5067-positions of the nucleotide sequence of the prototype)

The 5'-terminus and the 3'-terminus of all the molecular beacon probes used in the present example were labeled with TET and DABCYL, respectively (labeling was performed in accordance with the method described in Nature Biotechnology (1996, 14: 303-308)).

[Detection of virus]

(1) The detection method of the present invention was performed on the RNA samples extracted from stool specimens collected from 44 cases of non-bacterial gastroenteritis from which NLV particles were detected through electron microscopy performed in the Saitama Institute of Public Health during the period from 1998 to 2000, the specimens being the same as those employed in the above-described test to investigate highly conserved regions of NLv (GII) genes.

First, each of the RNA samples was subjected to reverse transcription reaction. Briefly, each of the RNA samples (8 μL) was mixed with a 12 μL solution for reverse transcription reaction. (The solution was prepared as follows: A dNTP solution (10 mM, 1 μL), random hexamer (75 pmol), RNasin (30 units, Promega, USA), SuperScript II RNaseH (−) Reverse Transcriptase (200 units, Gibco BRL, USA), DTT (100 mM, 1 μL), and a 5-fold diluted reverse transcription buffer (250 mM, Tris-HCl (pH 8.3), 375 mM KCl, 15 mM $MgCl_2$) were mixed, and the mixture was diluted with sterilized distilled water to attain a total volume of 12 μL.) The mixture was allowed to react at 42° C. for one hour or more. Subsequently, the resultant mixture was subjected to enzyme inactivation reaction for 15 minutes at 70° C., whereby a cDNA sample corresponding to each of the RNA samples (RT products) was prepared. Separately, a reaction mixture was prepared as follows: A buffer (25 μL), RT products (5 μL), primer (50 nM each), and fluorescent probe (Taq-Man probe G2TM1, 5-20 pmol) were mixed, and the mixture was diluted with sterilized distilled water to attain a total volume of 50 μL. The reaction mixture was subjected to PCR reaction by use of a nucleic acid obtained through mixing G2FA, G2RA1, and G2RA2, and G2RA2 (gene amplification primers) as a primer set for gene amplification, and a Taq-Man universal buffer Kit (ABI, USA) (PCR cycle:50° C. for two minutes→95° C. for 10 minutes→(95° C. for one minute→56° C. for three minutes)×50 cycles)). The fluorescence intensity was monitored over time during the reaction by use of ABI7700 (ABI, USA).

A cDNA fragment of SzuGII strain was subjected to cloning by use of pT7blue vector (Novagen, USA) through a conventional method. The fragment has a nucleotide sequence corresponding to the 5207- to 5696-positions of the nucleotide sequence of the cDNA of the prototype (standard strain) of NLVs (GII). Through use of the thus-cloned cDNA as a positive control specific to NLVs (GII), NLV (GII) gene detection was performed in accordance with the aforementioned procedure. In all the cases in which the primers and probes of Set A or B were used, the following were confirmed: $10^1$ to $10^7$ copy genes of NLVs (GII) can be detected (detection limit: $10^1$ copy genes/reaction), and NLVs (GII) can be quantitatively detected by reference to Ct values (threshold cycle number).

Among the aforementioned stool specimens which had been collected from 44 patients of non-bacterial gastroenteritis, 28 cases (63.6%) were found to be NLV (GII) positive, whereas the remaining 16 cases (36.4%) were found to be NLV (GII) negative. However, in all these 16 cases, WLVs (GI) were detected by another method. Taking the results regarding these two types of NLVs (GII and GI) together, the detection rate of NLVs was found to be 100%.

In cases where a system similar to the above and the following combination of gene amplification primers were used, results similar to those described above were obtained: (combination: a mixture of G2FB1, G2FB2, G2FB3, G2RA1, and G2RA2; and a mixture of G2FA, G2RB1, G2RB2, and G2RB3).

Also, when the gene detection probe was a Taq-Man probe G2TM2 (instead of G2TM1), or a molecular beacon probe G2MB1 to 7, analogous results were obtained.

(2) In order to demonstrate that the detection method of the present invention can be carried out on food, the method was performed through use of fresh oysters instead of the aforementioned stool specimens as test specimens.

From each of the 40 fresh oyster individuals, the midgut gland was removed, and sterilized distilled water was added thereto. Subsequently, the midgut gland was subjected to three cycles of freezing and thawing, whereby the tissues of the midgut gland were lyzed. The lyzed tissues were subjected to centrifugation at 10,000×g for 20 minutes. From the supernatant (140 μL) obtained through the centrifugation, nucleic acid was extracted through use of QIA Viral RNA (QIAGEN, USA) in accordance with the manufacturer's protocol. The extract was suspended in sterilized distilled water (50 μL). Through use of the suspension as an RNA sample of each fresh oyster, the detection method of the present invention was carried out by use of a molecular beacon probe G2MB1 as a gene detection probe in accordance with the procedure described in (1) above.

As a result, NLVs (GII) were detected in two fresh oyster individuals.

The results obtained in (1) and (2) clarified that the detection method of the present invention enables rapid, accurate detection of NLVs (GII) Moreover, as described above, through use of a nucleic acid probe specific to NLVs (GII) as a primer for gene detection, by monitoring the gene amplification process, the detection method of the present invention enables quantitative detection of NLVs (GII). In conclusion, the present invention provides a virus detection method of very high sensitivity and efficiency.

Industrial Applicability

The present invention has identified a highly conserved gene region in the genes of NLVs (GII), and on the basis of this finding, a rapid, accurate means for detecting NLVs is provided.

The invention claimed is:

1. A method of detecting a Norwalk-like virus (GII) in a sample comprising:

(a) performing a nucleic acid amplification reaction on a sample using at least two oligonucleotide primers, wherein a first oligonucleotide primer comprises a nucleotide sequence of at least 10 consecutive nucleotides of a region consisting of nucleotides 138 to 178 of the polynucleotide sequence set forth in SEQ ID NO:14 and a second oligonucleotide primer comprises a nucleotide sequence complementary to at least 10 consecutive nucleotides of a region consisting of nucleotides 230 to 257 of the polynucleotide sequence set forth in SEQ ID NO:14, and (b) detecting an amplification product, thereby detecting a Norwalk-like virus (GII) in a sample.

2. The method according to claim 1, wherein the first oligonucleotide comprises primer corresponds to between 15 and 30 consecutive nucleotides of the region consisting of nucleotides 138 to 178 of the polynucleotide sequence set forth in SEQ ID NO:14 and the second oligonucleotide primer is complementary to between 15 and 28 consecutive nucleotides of the region consisting of nucleotides 230 to 257 of the polynucleotide sequence set forth in SEQ ID NO:14.

3. The method according to claim 1, wherein the first oligonucleotide primer is an oligonucleotide primer of SEQ ID NO:1, and said second oligonucleotide primer is an oligonucleotide primer of SEQ ID NO: 5 and/or 6.

4. The method according to claim 1, wherein said amplification product comprises a polynucleotide sequence of positions 192 to 217 of SEQ ID NO:14 and a polynucleotide sequence complementary to positions 192 to 217 of SEQ ID NO:14.

5. The method according to claim 1, wherein said detecting an amplification product is performed using an oligonucleotide probe comprising a polynucleotide sequence complementary to the amplification product.

6. The method according to claim 1, wherein said detecting an amplification product is performed using an oligonucleotide probe selected from the group consisting of SEQ ID NOs: 10, 11, 12, 13, 121, 122, 123, 124 and 125.

7. The method according to claim 6, wherein the oligonucleotide probe is a molecular beacon probe or a labeled probe.

8. A method of detecting a Norwalk-like virus (GII) in a sample comprising:

(a) performing a nucleic acid amplification reaction on a sample to obtain an amplification product, said amplification product comprising a polynucleotide sequence complementary to positions 192 to 217 of SEQ ID NO:14, and (b) detecting the amplification product using an oligonucleotide probe, said oligonucleotide probe comprising a polynucleotide sequence complementary to the amplification product.

9. The method according to claim 8, wherein said oligonucleotide probe is selected from the group consisting of SEQ ID NOs: 10, 11, 12, 13, 121, 122, 123, 124 and 125.

10. The method according to claim 8, wherein the oligonucleotide probe is a molecular beacon probe or a labeled probe.

11. The method according to claim 8, wherein said nucleic acid amplification reaction is performed using at least two oligonucleotide primers, wherein a first oligonucleotide primer comprises a nucleotide sequence of at least 10 consecutive nucleotides of positions 138 to 178 of the polynucleotide sequence set forth in SEQ ID NO:14 and a second oligonucleotide primer comprises a nucleotide sequence complementary to a region of at least 10 consecutive nucleotides of positions 230 to 257 of the polynucleotide sequence set forth in SEQ ID NO:14.

12. The method according to claim 11, wherein said first oligonucleotide primer is an oligonucleotide primer of SEQ ID NO:1 and said second oligonucleotide primer is an oligonucleotide primer of SEQ ID NO: 5 and/or 6.

* * * * *

SEQUENCE LISTING

```
<160> NUMBER OF SEQ ID NOS: 125

<210> SEQ ID NO 1
<211> LENGTH: 26
<212> TYPE: DNA
<213> ORGANISM: Norwalk-like Virus (GII)
<220> FEATURE:
<221> NAME/KEY: misc_feature
<222> LOCATION: (9)..(9)
<223> OTHER INFORMATION: n is a, c, g, or t

<400> SEQUENCE: 1

cargarbcna tgttyagrtg gatgag                                          26


<210> SEQ ID NO 2
<211> LENGTH: 20
<212> TYPE: DNA
<213> ORGANISM: Norwalk-like Virus (GII)

<400> SEQUENCE: 2

gghccmbmdt tytacagcaa                                                 20


<210> SEQ ID NO 3
<211> LENGTH: 20
<212> TYPE: DNA
<213> ORGANISM: Norwalk-like Virus (GII)

<400> SEQUENCE: 3

gghccmbmdt tytacaagaa                                                 20


<210> SEQ ID NO 4
<211> LENGTH: 20
<212> TYPE: DNA
<213> ORGANISM: Norwalk-like Virus (GII)
<220> FEATURE:
<221> NAME/KEY: misc_feature
```

-continued

<222> LOCATION: (18)..(18)
<223> OTHER INFORMATION: n is a, c, g, or t

<400> SEQUENCE: 4
gghccmbmdt tytacarnaa 20

<210> SEQ ID NO 5
<211> LENGTH: 21
<212> TYPE: DNA
<213> ORGANISM: Norwalk-like Virus (GII)

<400> SEQUENCE: 5
tcgacgccat cttcattcac a 21

<210> SEQ ID NO 6
<211> LENGTH: 20
<212> TYPE: DNA
<213> ORGANISM: Norwalk-like Virus (GII)

<400> SEQUENCE: 6
tcaytcgacg ccatcttcat 20

<210> SEQ ID NO 7
<211> LENGTH: 23
<212> TYPE: DNA
<213> ORGANISM: Norwalk-like Virus (GII)

<400> SEQUENCE: 7
ccaccwgcat aaccattrta cat 23

<210> SEQ ID NO 8
<211> LENGTH: 23
<212> TYPE: DNA
<213> ORGANISM: Norwalk-like Virus (GII)

<400> SEQUENCE: 8
ccaccwgcat gcccattrta cat 23

<210> SEQ ID NO 9
<211> LENGTH: 23
<212> TYPE: DNA
<213> ORGANISM: Norwalk-like Virus (GII)
<220> FEATURE:
<221> NAME/KEY: misc_feature
<222> LOCATION: (6)..(6)
<223> OTHER INFORMATION: n is a, c, g, or t

<400> SEQUENCE: 9
ccrccngcat rhccrttrta cat 23

<210> SEQ ID NO 10
<211> LENGTH: 20
<212> TYPE: DNA
<213> ORGANISM: Norwalk-like Virus (GII)

<400> SEQUENCE: 10
tgggagggcg atcgcaatct 20

<210> SEQ ID NO 11
<211> LENGTH: 20
<212> TYPE: DNA
<213> ORGANISM: Norwalk-like Virus (GII)

<400> SEQUENCE: 11

-continued agattgcgat cgccctccca 20

<210> SEQ ID NO 12
<211> LENGTH: 27
<212> TYPE: DNA
<213> ORGANISM: Artificial Sequence
<220> FEATURE:
<223> OTHER INFORMATION: probe

<400> SEQUENCE: 12
cgtgctggga gggcgatcgc aagcacg 27

<210> SEQ ID NO 13
<211> LENGTH: 29
<212> TYPE: DNA
<213> ORGANISM: Artificial Sequence
<220> FEATURE:
<223> OTHER INFORMATION: probe

<400> SEQUENCE: 13
ccgtggattg cgatcgccct cccccacgg 29

<210> SEQ ID NO 14
<211> LENGTH: 600
<212> TYPE: DNA
<213> ORGANISM: Norwalk-like Virus (GII)

<400> SEQUENCE: 14
ctgaaacaat gattccacac tcccaaagac ccatacaatt aatgtcccta ctgggagagg 60
ccgcactcca cggcccagca ttctacagca aaattagcaa gctagtcatt gcagagttga 120
aggaaggtgg catggacttt tacgtgccca gacaagagcc aatgttcaga tggatgagat 180
tctcagatct gagcacgtgg gagggcgatc gcaatctggc tcccagtttt gtgaatgaag 240
atggcgtcga gtgacgccaa cccatctgat gggtccgcag ccaacctcgt cccagaggtc 300
aacaatgagg ttatggctct ggagcccgtt gttggtgccg ctattgcggc acctgtagcg 360
ggccaacaaa atataattga cccctggatt agaaataatt ttgtacaagc ccctggtgga 420
gagtttacag tgtcccctag aaacgctcca ggtgagatac tatggagcgc gcccttgggc 480
cctgatttga atccctatct ttctcacttg tccagaatgt ataatggtta tgcaggtggt 540
tttgaagtgc aagtgatcct tgcggggaac gcgttcaccg ccgggaaagt tatatttgca 600

<210> SEQ ID NO 15
<211> LENGTH: 600
<212> TYPE: DNA
<213> ORGANISM: Norwalk-like Virus (GII)

<400> SEQUENCE: 15
ctgaaacaat gataccacac tcccaaagac ccatacaact aatgtctttg ctgggcgagg 60
ccgcactcca cggcccagca ttctacagca aaattagcaa gctagtcatt gcagaactga 120
aggaaggtgg catggatttt tacgtgccca gacaagagcc aatgttcaga tggatgagat 180
tctcagatct gagcacgtgg gagggcgatc gcaatctggc tcccagcttt gtgaatgaag 240
atggcgtcga atgacgccaa cccatctgat gggtccgcag ccaacctcgt cccagaggtc 300
aataatgagg ttatggctct ggagcccgtt gttggtgccg ctattgcggc acctgtggcg 360
ggccaacaaa acgtaattga cccctggatt agaaacaatt ttgtacaagc ccctggtgga 420
gagttcacag tgtcccctag aaacgctcca ggtgagatac tgtggagcgc gcccttgggc 480
cctgatctga acccctatct ttctcatttg tccagaatgt acaatggtta tgcaggtggt 540
tttgaagtgc aagtaatcct cgcggggaat gcgttcaccg ccgggaaagt catatttgca    600

<210> SEQ ID NO 16
<211> LENGTH: 600
<212> TYPE: DNA
<213> ORGANISM: Norwalk-like Virus (GII)

<400> SEQUENCE: 16
ttgagtcaat gatcccacac tctcagaggc ccatacagct tatgtcactc ttaggtgaag     60
cagcactgca tgaaccatca ttctacagca agatcagcaa gcttgtgata tctgaactga    120
aagaaggtgg aatggatttt tacgtgccca ggcaagaacc catgttcaga tggatgagat    180
tctcagattt gagcacgtgg gagggcgatc gcaatcttgc tcccagtctt gtgaatgaag    240
atggcgtcga atgacgccgc tccatctact gatggtgcag ccggcctcgt gccagaaagt    300
aataatgagg tcatggctct tgaacccgtg gctggcgccg ccttggcagc cccggtcacc    360
ggtcaaacaa atataataga cccttggatt agagcaaatt ttgtccaggc ccctaatggt    420
gaatttacag tttctccccg caatgcccct ggtgaagtgc tattgaatct agagttgggt    480
ccagaattga atccttatct ggcacattta gcaagaatgt ataacgggta tgccggtggg    540
atggaggtgc aggtcatgtt ggctgggaac gcgttcacag ccggcaaatt ggtcttcgcc    600

<210> SEQ ID NO 17
<211> LENGTH: 600
<212> TYPE: DNA
<213> ORGANISM: Norwalk-like Virus (GII)

<400> SEQUENCE: 17
ctgaaacaat gataccacat tcccaaaggc ccatacagtt gatgtctctg ctaggtgaag     60
ctgcattgca cggtccagca ttctacagca aaatcagtaa actagtcatt tcagagttga    120
aggaaggtgg catggacttt tacgtgccca ggcaagagcc gatgttcaga tggatgagat    180
tctcagacct gagcacgtgg gagggcgatc gcaatctggc tcccagtttt gtgaatgaag    240
atggcgtcga atgacgccgc cccatctaat gatggtgcag ccggtctcgt accagaggtc    300
aacaacgaga cgatggccct cgaaccggtg gctggggctt ctatagccgc ccctctaacc    360
ggtcaaaata atgtgataga cccctggatt agaatgaact ttgtccaagc cccaaatgga    420
gaattcacag tgtctccccg caattctcct ggtgaaatct tgctaaattt ggaattaggc    480
cctgaattaa atccattctc agcacacctt tcaagaatgt ataatggtta tgccggcggg    540
gttgaagtgc aggtactact cgctgggaac gcgttcacag cgggaaaact ggtgtttgca    600

<210> SEQ ID NO 18
<211> LENGTH: 600
<212> TYPE: DNA
<213> ORGANISM: Norwalk-like Virus (GII)

<400> SEQUENCE: 18
gtgaaaccat gataccacat gcgcagagac ccgtgcagct catggcacta ctgggagagt     60
cctccctaca tggaccctca ttttacagca aggtcagcaa gctggttata tctgaactta    120
aggagggagg aatggatttt tatgtgccca gacaagagtc aatgttcagg tggatgaggt    180
tctcagatct aagcacatgg gagggcgatc gcaatctggc ccccagtttt gtgaatgaag    240
atggcgtcga atgacgctgc tccatctaat gatggtgccg cctgcctcgt cccagagatc    300
aacaatgagg caatggcgct agagccagtg gccggttcag cgatagcagc tcccctcact    360

-continued

```
ggccagcaaa atataattga tccctggatt atgaataatt ttgtacaagc acctggtggt    420

gagtttacag tgtcacccag gaattcccct ggtgaagtgc ttcttaactt ggagttaggt    480

ccagaaataa atccttattt ggctcatctc gctagaatgt acaatggtta tgcaggtgga    540

tttgaagtgc aagtggtcct agctggaaat gcgtttacag caggaaagat tatctttgca    600
```

<210> SEQ ID NO 19
<211> LENGTH: 600
<212> TYPE: DNA
<213> ORGANISM: Norwalk-like Virus (GII)

<400> SEQUENCE: 19

```
gtgaaaccat gataccacat acgcagagac ccgtgcagct catggcactg ctgggagaat     60

cctccctaca tggaccctca ttttacagca aggttagcaa gctggttata tctgaactta    120

aggagggagg aatggacttt tatgtgccca gacaagagtc aatgttcagg tggatgaggt    180

tctcagatct aagcacatgg gagggcgatc gcaatctggc tcccagtttt gtgaatgaag    240

atggcgtcga atgacgctgc tccatctaat gatggtgccg ccggcctcgt cccagagatc    300

aacaatgagg caatggcgct agatccagtg gcgggtgcag cgatagcagc acccctcact    360

ggccagcaaa atataattga tccctggatt atgaataact ttgtgcaagc acctggtggt    420

gagtttacag tgtcacctag gaattcccct ggtgaagtgc ttcttaattt ggaattaggt    480

ccagaaataa atccctattt ggctcatctt gctagaatgt acaatggtta tgcaggtggg    540

tttgaagtgc aagtggtcct ggctggaaat gcgtttacag cagcaaaggt gatctttgca    600
```

<210> SEQ ID NO 20
<211> LENGTH: 600
<212> TYPE: DNA
<213> ORGANISM: Norwalk-like Virus (GII)

<400> SEQUENCE: 20

```
ctgaaacaat gatatccaca ctcccgaaga cccatacgct aatgtcactg ttaggtgaag     60

cagcactgca tggaccatca ttctacagta agattattaa gctagttatt gcagagctga    120

aggaaggtgg catggacttt tacgtgccta gacaagaacc aatgttccgg tggatgaggt    180

tctcagactt gagcacgtgg gagggcgatc gcaatctggc tcccagcttt gtgaatgaag    240

atggcgtcga atgacgccac tccatctaat gatggtgccg ccggcctcgt cccagagatc    300

aacaatgagg caatggcgct agacccagtg gcgggtgcag cgatagcagc acccctcact    360

ggtcagcaaa acataattga tccctggatt atgaataatt ttgtgcaagc acctggtggt    420

gagtttacag tgtcccctag gaatccccct ggtgaagtgc ttcttaattt ggaattgggc    480

ccagaaataa acccctattt ggcccatctt gctagaatgt ataatggtta tgcaggtgga    540

tttgaagtgc aggtagtcct ggctgggaat gcgtttacag caggaaagat aatctttgca    600
```

<210> SEQ ID NO 21
<211> LENGTH: 600
<212> TYPE: DNA
<213> ORGANISM: Norwalk-like Virus (GII)

<400> SEQUENCE: 21

```
ctgaaacaat gatatccaca ctcccaaaga cccatacact aatgtctttg ctgggcgagg     60

ccgcactcca cggcccagca ttctacagca aaattagcaa gctagtcatt gcagaactga    120

aggaaggtgg catggatttt tacgtgccca gacaagagcc aatgttcaga tggatgagat    180

tctcagatct gagcacgtgg gagggcgatc gcaatctggc tcccagcttt gtgaatgaag    240
```

-continued atggcgtcga atgacgccaa cccatctgat gggtccgcag ccaacctcgt cccagaggtc 300
aataatgagg ttatggctct ggagcccgtt gttggtgccg ctattgcggc acctgtggcg 360
ggccaacaaa acgtaattga cccctggatt agaaacaatt ttgtacaagc ccctggtgga 420
gagttcacag tgtcccctag aaacgctcca ggtgagatac tgtggagcgc gcccttgggc 480
cctgatctga accoctatct ttctcatttg tccagaatgt acaatggtta tgcaggtggt 540
tttgaagtgc aagtaatcct cgcggggaac gcgttcaccg ccgggaaagt catatttgca 600

<210> SEQ ID NO 22
<211> LENGTH: 600
<212> TYPE: DNA
<213> ORGANISM: Norwalk-like Virus (GII)

<400> SEQUENCE: 22
gtgaaaccat gatatccact gtgctgaaga ccgagacgct catggcacta ctgggagaat 60
cctccctaaa tggaccctca ttttacagca aggtcagcaa gctggttata tctgaactta 120
aggagggagg aatggatttt tatgtgccca gacaagagtc aatgttcagg tggatgaggt 180
tctcagatct aagcacatgg gagggcgatc gcaatctggc ctccagtttt gtgaatgaag 240
atggcgtcga atcgcgctgc tccatctaat gatggtgccg cctgcctcgt cccagagatc 300
aacaatgagg caatggcgct agagccagtg gcgggtgcag cgatagcagc gcccctcact 360
ggccagcaaa atataattga tccctggatt atgaataatt ttgtgcaagc acctggtggt 420
gagtttacag tgtcacccag gaattcccct ggtgaagtgc ttcttaattt ggaattaggt 480
ccagaaataa atccttattt ggctcatctt gctagaatgt acaatggtta tgcaggtgga 540
tttgaagtgc aagtggtcct ggctggaaat gcgtttacag cagcaaaaat tatctttgca 600

<210> SEQ ID NO 23
<211> LENGTH: 600
<212> TYPE: DNA
<213> ORGANISM: Norwalk-like Virus (GII)

<400> SEQUENCE: 23
ctgaaacaat gataccacac tcccaaagac ccatacaatt gatgtctttg ctgggcgagg 60
ctgcactcca cggcccagca ttctacagca aaatcagcaa gctggtcatt gcagagctga 120
aggaaggtgg catggatttt tacgtgccca gacaagagcc aatgttcaga tggatgaggt 180
tctcagatct gagcacgtgg gagggcgatc gcaatctggc tcccagtttt gtgaatgaag 240
atggcgtcga gtgacgccgc tccatctaat gatggtgcag ccggtcttgt accagaggct 300
aacaatgaga ccatggcact tgaaccggtg gctggggctt caatagccgc cccactcacc 360
ggtcaaaaca atattataga cccctggatt agattaaatt ttgtgcaggc tcccaatggg 420
gagttcacgg tttcaccccg caactcgccc ggggaagtcc tattaaactt ggaattaggc 480
cccgaactaa atccatacct agcacacctt tctagaatgt ataatggtta tgcaggtggg 540
gttgaggtgc aagtactact ggctgggaat gcgttcacag ctggaaaatt ggtgtttgcg 600

<210> SEQ ID NO 24
<211> LENGTH: 600
<212> TYPE: DNA
<213> ORGANISM: Norwalk-like Virus (GII)

<400> SEQUENCE: 24
acgagagcat ggttccccat tctcagcgag ccacacagct catggccctt cttggtgagg 60

-continued

```
cctcattgca tggcccccag ttttacaaga aagttagcaa gatggtcatc aatgagatta    120

agagtggtgg tctggaattt tatgtgccca gacaagaggc catgtttagg tggatgagat    180

tctctgacct cagcacatgg gagggcgatc gcaatcttgc tcccgagggt gtgaatgaag    240

atggcgtcga atgacgccgc tccatcgaat gatggtgctg ccaacctcgt accagaggcc    300

aacaatgagg ttatggcact tgaaccggtg gtaggagcct caatcgcagc tcctgttgtc    360

ggtcagcaaa atataattga cccctggatt agagaaaatt ttgtccaagc accacagggc    420

gagtttactg tttcgccaag gaattcgcct ggtgagatgc ttttaaacct tgagttgggc    480

ccagaactta acccctattt gagtcatttg tcccccatgt acaacggata tgctggtggc    540

atgcaggttc aggtggtcct agctgggaat gcgttcacag ctgggaaaat catctttgcc    600
```

```
<210> SEQ ID NO 25
<211> LENGTH: 600
<212> TYPE: DNA
<213> ORGANISM: Norwalk-like Virus (GII)

<400> SEQUENCE: 25

acgagagcat ggttccccat tctcagcgag ccacacagct catggccctt cttggtgagg     60

cctcattgca tggcccccag ttttacaaga aagttagcaa gatggtcatc aatgagatta    120

agagtggtgg tctggaattt tatgtgccca gacaagaggc catgtttagg tggatgagat    180

tctctgacct cagcacatgg gagggcgatc gcaatcttgc tcccgagggt gtgaatgaag    240

atggcgtcga atgacgccgc tccatcgaat gatggtgctg ccaacctcgt accagaggcc    300

aacaatgagg ttatggcact tgaaccggtg gtaggagcct caatcgcagc tcctgttgtc    360

ggtcagcaaa atataattga cccctggatt agagaaaatt ttgtccaagc accacagggc    420

gagtttactg tttcgccaag gaattcgcct ggtgagatgc ttttaaacct tgagttgggc    480

ccagaactta acccctattt gagtcatttg tcccccatgt acaacggata tgctggtggc    540

atgcaggttc aggtggtcct agctgggaat gcgttcacag ctgggaaaat catctttgcc    600
```

```
<210> SEQ ID NO 26
<211> LENGTH: 600
<212> TYPE: DNA
<213> ORGANISM: Norwalk-like Virus (GII)

<400> SEQUENCE: 26

atgaaagcat ggtcccccac tcccaacggg ccacacaact catggccctt cttggtgaag     60

cttcattaca cggaccccaa ttctacaaga aggtcagtaa gatggttatc agtgagatta    120

agagtggtgg tctggaattt tatgtgccca gacaagaggc catgtttagg tggatgagat    180

tctctgacct cagcacatgg gagggcgatc gcaatcttgc tcccgagagt gtgaatgaag    240

atggcgtcga atgacgctgc tccatcgaat gatggtgctg ccaacctcgt accagaggcc    300

aacaatgagg ttatggcact tgaaccggtg gtgggagcct caattgcagc tcctgtcgtc    360

ggtcaacaaa atataattga cccctggatt agagaaaatt ttgttcaggc accacagggt    420

gagtttactg tttcaccaag aaactcgcct ggtgagatgc ttttaaatct tgaattaggc    480

ccagagctca atccttacct gagtcattta tcccgcatgt ataatggtta tgctggtggc    540

atgcaggttc aggtggtcct agctgggaac gcgttcacag ctggtaaaat catctttgcc    600
```

```
<210> SEQ ID NO 27
<211> LENGTH: 600
<212> TYPE: DNA
<213> ORGANISM: Norwalk-like Virus (GII)
```

-continued

<400> SEQUENCE: 27
atgaaagcat ggtcccccac tcccaacggg ccacacaact catggccctt cttggtgaag 60
cttcattaca cggaccccaa ttctacaaga aggtcagtaa gatggttatc agtgagatta 120
agagtggtgg tctggaattt tatgtgccca gacaagaggc catgtttagg tggatgagat 180
tctctgacct cagcacatgg gagggcgatc gcaatcttgc tcccgagagt gtgaatgaag 240
atggcgtcga atgacgctgc tccatcgaat gatggtgctg ccaacctcgt accagaggcc 300
aacaatgagg ttatggcact tgaaccggtg gtgggagcct caattgcagc tcctgtcgtc 360
ggtcaacaaa atataattga cccctggatt agagaaaatt ttgttcaggc accacagggt 420
gagtttactg tttcaccaag aaactcgcct ggtgagatgc ttttaaatct tgaattaggc 480
ccagagctca atccttacct gagtcattta tcccgcatgt ataatggtta tgctggtggc 540
atgcaggttc aggtggtcct agctgggaac gcgttcacag ctggtaaaat catctttgcc 600

<210> SEQ ID NO 28
<211> LENGTH: 600
<212> TYPE: DNA
<213> ORGANISM: Norwalk-like Virus (GII)

<400> SEQUENCE: 28
gtgaaaccat gataccacat gcgcagagac ccgtgcagct catggcacta ctgggagaat 60
cctccctgca tggaccctca ttctacagca aggtcagcaa gctggttata tctgaactta 120
aggagggagg aatggatttt tatgtgccca gacaagagtc aatgtttagg tggatgaggt 180
tctcagatct gagcacatgg gagggcgatc gcaatctggc tcccagtttt gtgaatgaag 240
atggcgtcga atgacgctgc tccatctaat gatggtgccg ccggcctcgt cccagagatc 300
aacaatgagg caatggcgct agagccagtg gcgggcgcag cgatagcagc gcccctcact 360
ggccagcaaa atataattga tccctggatt atgaataatt ttgtgcaagc acctggtggt 420
gagtttacag tgtcacctag gaattcccct ggtgaagtgc ttcttaattt ggaattaggt 480
ccagaaataa acccctattt ggctcatctt gctagaatgt acaatggtta tgcaggtgga 540
tttgaagtgc aagtggtcct agctggaaat gcgtttacgg caggaaaggt tatctttgca 600

<210> SEQ ID NO 29
<211> LENGTH: 600
<212> TYPE: DNA
<213> ORGANISM: Norwalk-like Virus (GII)

<400> SEQUENCE: 29
ttgaaagcat gattccccac tcccagagag caacccagct aatggccctc cttggggaag 60
cctcgttgca tggtccccag ttttacaaaa aggtgagtaa aatggtcatc aatgagatca 120
agagtggtgg tctggagttt tacgtgccca gacaggaggc catgttcaga tggatgagat 180
tttcagacct cagcacgtgg gagggcgatc gcaatctggc tcccgagaat gtgaatgaag 240
atggcgtcga atgacgcagc tccatcgaat gatggcgcgg ctggcctcgt accagagatc 300
aaccatgagg tcatggccat agaacctgtt gcaggggcct ctttagcagc ccctgtcgta 360
ggacaactca atataattgt cccctggatt agaaataatt ttggacaagc ccctcgtgga 420
gagtttatag tgtaccctag aatcgctcca ggtgaatttt tattagatct agagttaggc 480
cctgagttga acccctacct tgctcacctt gcacgcatgt ataatgggca tgcaggtggt 540
atggaggtgc agatagtgct tgctgggaat gcgttcacag cgggcaaaat cctgtttgca 600

-continued

<210> SEQ ID NO 30
<211> LENGTH: 600
<212> TYPE: DNA
<213> ORGANISM: Norwalk-like Virus (GII)

<400> SEQUENCE: 30
gtgaaaccat gataccacat gcgcagagac ccgtgcagct catggcacta ctgggagaat 60
cctccctgca tggaccctca ttctacagca aggtcagcaa gctggttata tctgaactta 120
aggagggagg aatggatttt tatgtgccca gacaagagtc aatgtttagg tggatgaggt 180
tctcagatct aagcacatgg gagggcgatc gcaatctggc tcccagtttt gtgaatgaag 240
atggcgtcga atgacgctgc tccatctaat gatggtgccg ccggcctcgt cccagagatc 300
aacaatgagg caatggcgct agagccagtg gcgggcgcag cgatagcagc gcccctcact 360
ggccagcaaa atataattga tccctggatt atgaataatt ttgtgcaagc acctggtggt 420
gagtttacag tgtcacctag gaattcccct ggtgaagtgc ttcttaattt ggaattaggt 480
ccagaaataa acccctattt ggctcatctt gctagaatgt acaatggtta tgcaggtgga 540
tttgaagtgc aagtggtcct agctggaaat gcgtttacag caggaaaggt tatctttgca 600

<210> SEQ ID NO 31
<211> LENGTH: 507
<212> TYPE: DNA
<213> ORGANISM: Norwalk-like Virus (GII)

<400> SEQUENCE: 31
atgaaacaat gatacctcac tctcagaggc ccatacaact catggcccta cttggtgaag 60
cctctctaca cggaccctct ttctacagca aaattagcaa attggtcata actgaactca 120
aggaaggtgg aatggatttt tacgtgccaa gacaagagcc tatgtttagg tggatgagat 180
tctctgactt gagcacgtgg gagggcgatc gcaatctggc tcccagtttt gtgaatgaag 240
atggcgtcga atgacgctgc tccatcaaat gatggtgccg ccggcctcgt gccagaaagt 300
aataatgagg caatggccct ggaacccgtg gtgggggtgt ctttagccgc ccctgtcact 360
ggccaaacta atataataga cccctggatt agaactaatt ttgtccaagc ccctaatggt 420
gaatttacag tttcccctag aaattcccct ggagagatat tggtcaattt ggagttgggt 480
ccagaactga atccttatct ggcacat 507

<210> SEQ ID NO 32
<211> LENGTH: 513
<212> TYPE: DNA
<213> ORGANISM: Norwalk-like Virus (GII)

<400> SEQUENCE: 32
atgagacaat gattccacac ttccagagac ccatacaact aatgtcattg ctgggggaag 60
cagcattgca tggaccagct ttttacaaga aagttagcaa attagttatc actgagctca 120
aagagggtgg gatggatttc tatgtaccaa gacaggaacc catgttcaga tggatgagat 180
tctcagacct cagtacttgg gagggcgatc gcaatcttgc tcccgaaggt gtgaatgaag 240
atggcgtcga atgacgctgc tccatctaat gatggtgccg ccggcctcgt cccagagatc 300
aacaatgagg caatggcgct agacccagtg gcgggtgcag caatagcagc accccttact 360
ggccagcaaa atataattga tccctggatt atgaataact ttgtgcaagc acctggtggt 420
gagttcacag tgtcacctag aaattcccct ggtgaagtgt tacttaattt ggaattgggt 480
ccagaaataa atccctactt ggcccatctt gct 513

<210> SEQ ID NO 33
<211> LENGTH: 505
<212> TYPE: DNA
<213> ORGANISM: Norwalk-like Virus (GII)
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (101)..(102)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:

-continued

<221> NAME/KEY: misc_feature
<222> LOCATION: (128)..(128)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (170)..(170)
<223> OTHER INFORMATION: n is a, c, g, or t
<220> FEATURE:
<221> NAME/KEY: misc_feature
<222> LOCATION: (179)..(179)
<223> OTHER INFORMATION: n is a, c, g, or t
<220> FEATURE:
<221> NAME/KEY: misc_feature
<222> LOCATION: (218)..(218)
<223> OTHER INFORMATION: n is a, c, g, or t
<220> FEATURE:
<221> NAME/KEY: misc_feature
<222> LOCATION: (227)..(228)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (489)..(489)
<223> OTHER INFORMATION: n is a, c, g, or t

<400> SEQUENCE: 33
ntgaaaccat gattccacan tcncagagac ccntncagct natgncantn ctgggngant 60
cntcnttgca tggaccnncn ttttacaaca aggtcagcaa nntggttatc tctgagctna 120
angagggngg aatggatttt tatgtgccca gacaagagnc catgtttagn tggatgagnt 180
tctcagacct cagcacatgg gagggcgatc gcaatctngc tcccaanngt gtgaatgaag 240
atggcgtcga atgacgctgc tccatctaat gatggtgccg ccggcctcgt cccagagatc 300
aacaatgagg caatggcgct aganccagtg gcgggtgcag cnatagcagc gcccctcact 360
ggccagcaaa atataattga tccctggatt atgaataant ttgtgcaagc acctggtggt 420
gagttnacag tgtcacctag naattcncct ggtgaagtgc ttcttaattt ggaattaggt 480
ccagaaatna atccctactg gctct 505

<210> SEQ ID NO 34
<211> LENGTH: 516
<212> TYPE: DNA
<213> ORGANISM: Norwalk-like Virus (GII)

<400> SEQUENCE: 34

-continued atgagacaat gataccccac tctcaaagac ccatacagct tatggcactg cttggtgagg 60
cctcccttca cggaccctct ttctacagca agattagtaa attggtcata actgaactca 120
aagaaggtgg gatggatttt tacgtgccaa gacaggaacc tatgttcagg tggatgaggt 180
tttctgacct gagcacgtgg gagggcgatc gcaatctggc tcccagtttt gtgaatgaag 240
atggcgtcga atgacgccgc tccatctaat gatggtgcag ccggtctcgt accagaggtc 300
aacaacgaga caatggcact tgagccagtt gcgggagctt caatcgccgc ccctttaact 360
ggtcaaaaca atgtaataga cccctggatt agattaaatt ttgtacaagc ccccaatggt 420
gagttcacgg tttccccccg aaactcgcct ggtgaaattt tgttaaattt ggagttaggg 480
cctgaattga atccatattt agcccattta gcaaga 516

<210> SEQ ID NO 35
<211> LENGTH: 506
<212> TYPE: DNA
<213> ORGANISM: Norwalk-like Virus (GII)

<400> SEQUENCE: 35
atgagacaat gataccccac tctcaaagac ccatacagct tatggcactg cttggtgagg 60
cctcccttca cggaccctct ttctacagca agattagtaa attggtcata actgaactca 120
aagaaggtgg gatggatttt tacgtgccaa gacaggaacc tatgttcagg tggatgaggt 180
tttctgacct gagcacgtgg gagggcgatc gcaatctggc tcccagtttt gtgaatgaag 240
atggcgtcga atgacgccgc tccatctaat gatggtgcag ccggtctcgt accagaggtc 300
aacaacgaga caatggcact tgagccagtt gcgggagctt caatcgccgc ccctttaact 360
ggtcaaaaca atgtaataga cccctggatt agattaaatt ttgtacaagc ccccaatggt 420
gagttcacgg tttccccccg aaactcgcct ggtgaaattt tgttaaattt ggagttaggg 480
cctgaattga atccatattt agccca 506

<210> SEQ ID NO 36
<211> LENGTH: 511
<212> TYPE: DNA
<213> ORGANISM: Norwalk-like Virus (GII)

<400> SEQUENCE: 36
atgagacaat gattccacac tcccagaggc ccatacaact aatgtcattg ctgggggagg 60
cagcattaca cggaccagct ttctacaaga aagtcagtaa attagttatc actgagctca 120
aagagggtgg aatggatttt tacgtgccaa ggcaggaacc tatgtttagg tggatgagat 180
tctctgacct cagcacttgg gagggcgatc gcaatcttgc tcccgaaggt gtgaatgaag 240
atggcgtcga atgacgctac tccatcaaat gatggtgctg ccggcctcgt gccagaaagt 300
aacaatgagg caatggctct ggaacccgtg gtgggggcgt ctttagccgc ccctgtcact 360
ggccaaacta atataataga cccctggatt agaactaatt ttgtccaagc ccctaatggt 420
gaattcacag tttcccctag aaattcccct ggagagatat tggtcaattt ggagttgggt 480
ccagaactga acccttatct ggcacagtta g 511

<210> SEQ ID NO 37
<211> LENGTH: 511
<212> TYPE: DNA
<213> ORGANISM: Norwalk-like Virus (GII)

<400> SEQUENCE: 37

-continued

```
atgagacaat gataccccac tctcaaagac ccatacagct tatggcactg cttggtgagg      60

cctcccttca cggaccctct ttctacagca agattagtaa attggtcata actgaactca     120

aagaaggtgg gatggatttt tacgtgccaa gacaggaacc tatgttcagg tggatgaggt     180

tttctgacct gagcacgtgg gagggcgatc gcaatctggc tcccagtttt gtgaatgaag     240

atggcgtcga atgacgccgc tccatctaat gatggtgcag ccggtctcgt accagaggtc     300

aacaacgaga caatggcact tgagccagtt gcgggagctt caatcgccgc ccctttaact     360

ggtcaaaaca atgtaataga cccctggatt agattaaatt ttgtacaagc cccaatggt      420

gagttcacgg tttccccccg aaactcgcct ggtgaaattt tgttaaattt ggagttaggg     480

cctgaattga atccatattt agcccattta g                                    511
```

<210> SEQ ID NO 38
<211> LENGTH: 515
<212> TYPE: DNA
<213> ORGANISM: Norwalk-like Virus (GII)

<400> SEQUENCE: 38

```
atgagacaat gatacctcac tctcagaggc caatacaact catgtctcta cttggtgaag      60

ccgccctaca cggcccatca ttttacagca aaatcagcaa gctggttatc acagaactaa     120

aggaaggtgg catggatttt tacgtgccca ggcaagagcc catgtttagg tggatgagat     180

tctcagactt gagcacgtgg gagggcgatc gcaatctggc tcccagtttt gtgaatgaag     240

atggcgtcga atgacgccgc tccatctact gatggtgcag ccggcctcgt gccagaaagt     300

aataatgagg tcatggctct tgaacccgtg gctggtgccg ctttggcagc cccggtcacc     360

ggccaaacaa atattataga cccttggatt agagcaaatt ttgtccaggc ccctaatggt     420

gaatttacag tttctccccg taatgcccct ggtgaagtgc tattgaatct agagttgggt     480

ccagaattaa atccttatct ggcacattta gcaag                                515
```

<210> SEQ ID NO 39
<211> LENGTH: 508
<212> TYPE: DNA
<213> ORGANISM: Norwalk-like Virus (GII)

<400> SEQUENCE: 39

```
ctgaaacaat gattccacat tcccaaagac ccatacaatt gatgtcccta ctgggagagg      60

ccgcactcca cggcccagca ttctacagca aaattagcaa gttagttatt gcagagctaa     120

aagaaggtgg catggatttt tacgtgccca gacaagagcc aatgttcaga tggatgagat     180

tctcagatct gagcacgtgg gagggcgatc gcaatctggc tcccagtttt gtgaatgaag     240

atggcgtcga atgacgccaa cccatctgat gggtccacag ccaacctcgt cccagaggtc     300

aacaatgagg ttatggcttt ggagcccgtt gttggtgccg ctattgcggc acctgtagcg     360

ggccaacaaa atgtaattga cccctggatt agaaataatt ttgtacaagc ccctggtgga     420

gagtttacag tatcccctag aaacgctccg ggtgagatac tatggagcgc gcccttgggc     480

cctatttgaa cccctacctt ctcttggc                                        508
```

<210> SEQ ID NO 40
<211> LENGTH: 512
<212> TYPE: DNA
<213> ORGANISM: Norwalk-like Virus (GII)

<400> SEQUENCE: 40

```
ctgaaacaat gattccacat tcccaaagac ccatacaatt gatgtcccta ctgggagagg      60
```

-continued

```
ccgcactcca cggcccagca ttctacagca aaattagcaa gttagttatt gcagagctaa    120

aagaaggtgg catggatttt tacgtgccca gacaagagcc aatgttcaga tggatgagat    180

tctcagatct gagcacgtgg gagggcgatc gcaatctggc tcccagtttt gtgaatgaag    240

atggcgtcga atgacgccaa cccatctgat gggtccacag ccaacctcgt cccagaggtc    300

aacaatgagg ttatggcttt ggagcccgtt gttggtgccg ctattgcggc acctgtagcg    360

ggccaacaaa atgtaattga cccctggatt agaaataatt ttgtacaagc ccctggtgga    420

gagtttacag tatcccctag aaacgctccg ggtgagatac tatggagcgc gcccttgggc    480

cctgatttga acccctacct ttctcacttg gc                                  512


<210> SEQ ID NO 41
<211> LENGTH: 417
<212> TYPE: DNA
<213> ORGANISM: Norwalk-like Virus (GII)

<400> SEQUENCE: 41

aatcagcaag ctggtcattg cagagctgaa ggaaggtggc atggattttt acgtgcccag     60

acaagagcca atgttcagat ggatgaggtt ctcagatctg agcacgtggg agggcgatcg    120

caatctggct cccagttttg tgaatgaaga tggcgtcgag tgacgccgct ccatctaatg    180

atggtgcagc cggtcttgta ccagaggcta acaatgagac catggcactt gaaccggtgg    240

ctggggcttc aatagccgcc ccactcaccg gtcaaaacaa tattatagac ccctggatta    300

gattaaattt tgtgcaggct cccaatgggg agttcacggt ttcacccccgc aactcgcccg    360

gtgaagtcct attaaacttg gaattaggcc ccgaactaaa tccataccta gcacacc       417


<210> SEQ ID NO 42
<211> LENGTH: 421
<212> TYPE: DNA
<213> ORGANISM: Norwalk-like Virus (GII)

<400> SEQUENCE: 42

aatcagcaag ctggtcatca cagaactaaa ggaaggtggc atggattttt acgtgcccag     60

gcaagagccc atgtttaggt ggatgagatt ctcagacttg agcacgtggg agggcgatcg    120

caatctggct cccagttttg tgaatgaaga tggcgtcgaa tgacgccgct ccatctactg    180

atggtgcagc cggcctcgtg ccagaaagta ataatgaggt catggctctt gaacccgtgg    240

ctggtgccgc tttggcagcc ccggtcaccg gccaaacaaa tattatagac ccttggatta    300

gagcaaattt tgtccaggcc cctaatggtg aatttacagt ttctccccgt aatgcccctg    360

gtgaagtgct attgaatcta gagttgggtc cagaattaaa tctttatctg gctcttttag    420

c                                                                    421


<210> SEQ ID NO 43
<211> LENGTH: 422
<212> TYPE: DNA
<213> ORGANISM: Norwalk-like Virus (GII)

<400> SEQUENCE: 43

ggtcagtaag atggttatca gtgagatcaa gagtggtggt ctggagtttt atgtgcccag     60

acaagaggcc atgtttaggt ggatgagatt ctctgacctc agcacatggg agggcgatcg    120

caatcttgct cccgagagtg tgaatgaaga tggcgtcgaa tgacgctgct ccatcgaatg    180

atggtgctgc caacctcgta ccagaggcca acaatgaggt tatggcactt gaaccggtgg    240
```

-continued

```
tgggagcctc aattgcagct cctgtcgtcg gtcaacaaaa tataattgac ccctggatta    300

gagaaaattt tgttcaggca ccacagggtg agtttactgt ttcaccaaga aactcgcctg    360

gtgagatgct tttaaatctt gaattaggcc cagagctcaa tccttacctg agtcatttat    420

cc                                                                   422


<210> SEQ ID NO 44
<211> LENGTH: 422
<212> TYPE: DNA
<213> ORGANISM: Norwalk-like Virus (GII)

<400> SEQUENCE: 44

aattagcaag ttagttattg cagagctaaa agaaggtggc atggattttt acgtgcccag     60

acaagagcca atgttcagat ggatgagatt ctcagatctg aacacgtggg agggcgatcg    120

caatctggct cccagttttg tgaatgaaga tggcgtcgaa tgacgccaac ccatctgatg    180

ggtccacagc caacctcgtc ccagaggtca acaatgaggt tatggctttg gagcccgttg    240

ttggtgccgc tattgcggca cctgtagcgg gccaacaaaa tgtaattgac ccctggatta    300

gaaataattt tgtacaagcc cctggtggag agtttacagt atcccctaga aacgctccgg    360

gtgagatact atggagcgcg cccttgggcc ctgatttgaa cccctacctt tctcatttgg    420

cc                                                                   422


<210> SEQ ID NO 45
<211> LENGTH: 422
<212> TYPE: DNA
<213> ORGANISM: Norwalk-like Virus (GII)

<400> SEQUENCE: 45

aattagcaag ttggttattg cagagctaaa agaaggtggc atggattttt acgtgcccag     60

acaagagcca atgttcagat ggatgagatt ctcagatctg agcacgtggg agggcgatcg    120

caatctggct cccagttttg tgaatgaaga tggcgtcgaa tgacgccaac ccatctgatg    180

ggtccacagc caacctcgtc ccagaggtca acaatgaggt tatggctttg gagcccgttg    240

ttggtgccgc tattgcggca cctgtagcgg gccaacaaaa tgtaattgac ccctggatta    300

gaaataattt tgtacaagcc cctggtggag agtttacagt atcccctaga aacgctccgg    360

gtgagatact atggagcgcg cccttgggcc ctgatttgaa cccctacctt tctcatttgg    420

cc                                                                   422


<210> SEQ ID NO 46
<211> LENGTH: 410
<212> TYPE: DNA
<213> ORGANISM: Norwalk-like Virus (GII)

<400> SEQUENCE: 46

aattagcaag ttagttattg cagagctaaa agaaggtggc atggattttt acgtgcccag     60

acaagagcca atgttcagat ggatgagatt ctcagatctg agcacgtggg agggcgatcg    120

caatctggct cccagttttg tgaatgaaga tggcgtcgaa tgacgccaac ccatctgatg    180

ggtccacagc caacctcgtc ccagaggtca acaatgaggt tatggctttg gagcccgttg    240

ttggtgccgc tattgcggca cctgtagcgg gccaacaaaa tgtaattgac ccctggatta    300

gaaataattt tgtacaagcc cctggtggag agtttacagt atcccctaga aacgctccgg    360

gtgagatact atggagcgcg cccttgggcc ctgatttgaa cccctacctt              410
```

-continued

<210> SEQ ID NO 47
<211> LENGTH: 422
<212> TYPE: DNA
<213> ORGANISM: Norwalk-like Virus (GII)

<400> SEQUENCE: 47
ggtcagcaag ctggttatat ctgaacttaa ggagggagga atggattttt atgtgcccag 60
acaagagtca atgtttaggt ggatgaggtt ctcagatcta agcacatggg agggcgatcg 120
caatctggct cccagttttg tgaatgaaga tggcgtcgaa tgacgctgct ccatctaatg 180
atggtgccgc cggcctcgtc ccagagatca acaatgaggc aatggcgcta gagccagtgg 240
cgggcgcagc gatagcagcg cccctcactg gccagcaaaa tataattgat ccctggatta 300
tgaataattt tgtgcaagca cctggtggtg agtttacagt gtcacctagg aattcccctg 360
gtgaagtgct tcttaatttg gaattaggtc cagaaataaa cccctatttg gctcatcttg 420
ct 422

<210> SEQ ID NO 48
<211> LENGTH: 422
<212> TYPE: DNA
<213> ORGANISM: Norwalk-like Virus (GII)

<400> SEQUENCE: 48
ggtcagcaag ctggttatat ctgaacttaa ggagggagga atggattttt atgtgcccag 60
acaagagtca atgtttaggt ggatgaggtt ctcagatcta agcacatggg agggcgatcg 120
caatctggct cccagttttg tgaatgaaga tggcgtcgaa tgacgctgct ccatctaatg 180
atggtgccgc cggcctcgtc ccagagatca acaatgaggc aatggcgcta gagccagtgg 240
cgggcgcagc gatagcagcg ccactcactg gccagcaaaa tataattgat ccctggatta 300
tgaataattt tgtgcaagca cctggtggtg agtttacagt gtcacctagg aattcccctg 360
gtgaagtgct tcttaatttg gaattaggtc cagaaataaa cccctatttg gctcatcttg 420
ct 422

<210> SEQ ID NO 49
<211> LENGTH: 422
<212> TYPE: DNA
<213> ORGANISM: Norwalk-like Virus (GII)

<400> SEQUENCE: 49
ggtcagcaag ctggttatat ctgaacttaa ggagggagga atggattttt atgtgcccag 60
acaagagtca atgtttaggt ggatgaggtt ctcagatcta agcacatggg agggcgatcg 120
caatctggct cccagttttg tgaatgaaga tggcgtcgaa tgacgctgct ccatctaatg 180
atggtgccgc cggcctcgtc ccagagatca acaatgaggc aatggcgcta gagccagtgg 240
cgggcgcagc gatagcagcg cccctcactg gccagcaaaa tataattgat ccctggatta 300
tgaataattt tgtgcaagca cctggtggtg agtttacagt gtcacctagg aattcccctg 360
gtgaagtgct tcttaatttg gaattaggtc cagaaataaa cccctatttg gctcatcttg 420
ct 422

<210> SEQ ID NO 50
<211> LENGTH: 422
<212> TYPE: DNA
<213> ORGANISM: Norwalk-like Virus (GII)

<400> SEQUENCE: 50

-continued

```
agttagcaaa ttagttatca ctgagctcaa agagggtggg atggatttct atgtaccaag      60

acaggaaccc atgttcagat ggatgagatt ctcagacctc agtacttggg agggcgatcg     120

caatcttgct cccgaaggtg tgaatgaaga tggcgtcgaa tgacgctgct ccatctaatg     180

atggtgccgc cggcctcgtc ccagagatca acaatgaggc aatggcgcta gacccagtgg     240

cgggtgcagc aatagcagca ccccttactg gccagcaaaa tataattgat ccctggatta     300

tgaataactt tgtgcaagca cctggtggtg agttcatagt gtcacctaga aattctcctg     360

gtgaagtgtt acttaatttg gaattgggtc cagaaataaa tccctacttg gcccatcttg     420

ct                                                                     422
```

```
<210> SEQ ID NO 51
<211> LENGTH: 422
<212> TYPE: DNA
<213> ORGANISM: Norwalk-like Virus (GII)

<400> SEQUENCE: 51

ggtcagcaag ctggttatat ctgaacttaa ggagggagga atggattttt atgtgcccag      60

acaagagtca atgtttaggt ggatgaggtt ctcagatcta agcacatggg agggcgatcg     120

caatctggct cccagttttg tgaatgaaga tggcgtcgaa tgacgctgct ccatctaatg     180

atggtgccgc cggcctcgtc ccagagatca acaatgaggc aatggcgcta gacccagtgg     240

cgggtgcagc aatagcagca ccccttactg gccagcaaaa tataattgat ccctggatta     300

tgaataactt tgtgcaagca cctggtggtg agttcacagt gtcacctaga aattctcctg     360

gtgaagtgtt acttaatttg gaattaggtc cagaaataaa cccctatttg gctcatcttg     420

ct                                                                     422
```

```
<210> SEQ ID NO 52
<211> LENGTH: 422
<212> TYPE: DNA
<213> ORGANISM: Norwalk-like Virus (GII)

<400> SEQUENCE: 52

ggtcagcaag ctggttatat ctgaacttaa ggagggagga atggattttt atgtgcccag      60

acaagagtca atgtttaggt ggatgaggtt ctcagatcta agcacatggg agggcgatcg     120

caatctggct cccagttttg tgaatgaaga tggcgtcgaa tgacgctgct ccatctaatg     180

atggtgccgc cggcctcgtc ccagagatca acaatgaggc aatggcgcta gagccagtgg     240

cgggcgcagc gatagcagcg cccctcactg gccagcaaaa tataattgat ccctggatta     300

tgaataattt tgtgcaagca cctggtggtg agtttacagt gtcacctagg aattcccctg     360

gtgaagtgct tcttaatttg gaattaggtc cagaaataaa cccctatttg gctcatcttg     420

ct                                                                     422
```

```
<210> SEQ ID NO 53
<211> LENGTH: 422
<212> TYPE: DNA
<213> ORGANISM: Norwalk-like Virus (GII)

<400> SEQUENCE: 53

ggtcagcaag ctagttatat ctgaacttaa ggagggagga atggattttt atgtgcccag      60

acaagagtca atgtttaggt ggatgaggtt ctcagatcta agcacatggg agggcgatcg     120

caatctggct cccagttttg tgaatgaaga tggcgtcgaa tgacgctgct ccatctaatg     180

atggtgccgc cggcctcgtc ccagagatca acaatgaggc aatggcgcta gagccagtgg     240
```

-continued cgggcgcagc gatagcagcg cccctcactg gccagcaaaa tataattgat ccctggatta 300
tgaataattt tgtgcaagca cctggtggtg agtttacagt gtcacctagg aattcccctg 360
gtgaagtgct tcttaatttg gaattaggtc cagaaataaa cccttatttg gctcatcttg 420
ct 422

<210> SEQ ID NO 54
<211> LENGTH: 418
<212> TYPE: DNA
<213> ORGANISM: Norwalk-like Virus (GII)

<400> SEQUENCE: 54
aatcagcaag ctggtcattg cagagctgaa ggaaggtggc atggattttt acgtgcccag 60
gcaagagcct atgttcagat ggatgaggtt ttcagatctg agcacgtggg agggcgatcg 120
caatctggct cccagttttg tgaatgaaga tggcgtcgaa tgacgccgct ccatctaatg 180
atggtgcagc cggcctcgtg ccagaaagta acaatgaggt tatggctctt gaacctgttg 240
ctggggcatc tttagctgcc cctgtgactg gtcaaactaa tataattgac ccatggatca 300
gaatgaattt tgttcaagcc ccaaatggag aattcactgt ttccccaaga aattcccctg 360
gagaagtact cctaaatttg gaattgggtc ctgaattaaa cccttatctg gcacacct 418

<210> SEQ ID NO 55
<211> LENGTH: 418
<212> TYPE: DNA
<213> ORGANISM: Norwalk-like Virus (GII)

<400> SEQUENCE: 55
aatcagcaag ctggtcattg cagagctgaa ggaaggtggc atggattttt acgtgcccag 60
gcaagagcct atgttcagat ggatgaggtt ttcagatctg agcacgtggg agggcgatcg 120
caatctggct cccagttttg tgaatgaaga tggcgtcgaa tgacgccgct ccatctaatg 180
atggtgcagc cggcctcgtg ccagaaagta acaatgaggt tatggctctt gaacctgttg 240
ctggggcatc tttagctgcc cctgtgactg gtcaaactaa tataattgac ccatggatca 300
gaatgaattt tgttcaagcc ccaaatggag aattcactgt ttccccaaga aattcccctg 360
gagaagtact cctaaatttg gaattgggtc ctgaattaaa cccttatctg gcacacct 418

<210> SEQ ID NO 56
<211> LENGTH: 422
<212> TYPE: DNA
<213> ORGANISM: Norwalk-like Virus (GII)

<400> SEQUENCE: 56
ggtgagtaaa atggtcatca atgagatcaa gagtggtggt ctggagtttt acgtgcccag 60
acaggaggcc atgttcaggt ggatgagatt ttcagacctc agcacgtggg agggcgatcg 120
caatctggct cccgagaatg tgaatgaaga tggcgtcgaa tgacgcagct ccatcgaatg 180
atggcgcggc tggcctcgta ccagagatca accatgaggt catggccata gaacctgttg 240
caggggcatc tttagcagcc cctgtcgtag gacaacttaa cataattgat ccctggatta 300
gaaataattt tgtgcaagcc cctgctggag aatttactgt ttcacccaga aatgctccag 360
gtgaattttt gttagattta gagttaggcc ctgaattgaa cccctacctt gctcaccttg 420
ca 422

<210> SEQ ID NO 57

-continued

<211> LENGTH: 419
<212> TYPE: DNA
<213> ORGANISM: Norwalk-like Virus (GII)

<400> SEQUENCE: 57

```
aatcagcaag ctggtcattg cagagctgaa ggaaggtggc atggattttt acgtgcccag     60

gcaagagcct atgttcagat ggatgaggtt ttcagatctg agcacgtggg agggcgatcg    120

caatctggct cccagttttg tgaatgaaga tggcgtcgaa tgacgccgct ccatctaatg    180

atggtgcagc cggcctcgtg ccagaaagta acaatgaggt tatggctctt gaacctgttg    240

ctggggcatc tttagcagcc cctgtgactg gtcaaactaa tataattgac ccatggatca    300

gaatgaattt tgttcaagcc ccaaatggag aattcactgt ttccccaaga aattcccctg    360

gagaagtact cctaaatttg gaattgggtc ctgaattaaa cccttatctg gcacacctt     419
```

<210> SEQ ID NO 58
<211> LENGTH: 417
<212> TYPE: DNA
<213> ORGANISM: Norwalk-like Virus (GII)

<400> SEQUENCE: 58

```
aatcagcaag ctggtcattg cagagctgaa ggaaggtggc atggattttt acgtgcccag     60

gcaagagcct atgttcagat ggatgaggtt ttcagatctg agcacgtggg agggcgatcg    120

caatctggct cccagttttg tgaatgaaga tggcgtcgaa tgacgccgct ccatctaatg    180

atggtgcagc cggcctcgtg ccagaaagta acaatgaggt tatggctctt gaacctgttg    240

ctggggcatc tttagcagcc cctgtgactg gtcaaactaa tataattgac ccatggatca    300

gaatgaattt tgttcaagcc ccaaatggag aattcactgt ttccccaaga aattcccctg    360

gagaagtact cctaaatttg gaattgggtc ctgaattaaa cccttatctg gcacacc       417
```

<210> SEQ ID NO 59
<211> LENGTH: 422
<212> TYPE: DNA
<213> ORGANISM: Norwalk-like Virus (GII)

<400> SEQUENCE: 59

```
aatcagcaag ctggtcattg cagagctgaa ggaaggtggc atggattttt acgtgcccag     60

gcaagagcct atgttcagat ggatgaggtt ttcagatctg agcacgtggg agggcgatcg    120

caatctggct cccagttttg tgaatgaaga tggcgtcgaa tgacgccgct ccatctaatg    180

atggtgcagc cggcctcgtg ccagaaagta acaatgaggt tacggctctt gaacctgttg    240

ctggggcatc tttagctgcc cctgtgactg gtcaaactaa tataattgac ctatggacca    300

gaatgaatct tgttcaagcc ccaaatggag aattcactgt ttccccaaga aattcccctg    360

gagaagtact cctaaatttg gaattgggtc ctgaattaaa cccttatctg gcacacctat    420

ct                                                                   422
```

<210> SEQ ID NO 60
<211> LENGTH: 422
<212> TYPE: DNA
<213> ORGANISM: Norwalk-like Virus (GII)

<400> SEQUENCE: 60

```
aatcagcaag ctggtcattg cagagctgaa ggaaggtggc atggattttt acgtgcccag     60

gcaagagcct atgttcagat ggatgaggtt ttcagatctg agcacgtggg agggcgatcg    120

caatctggct cccagttttg tgaatgaaga tggcgtcgaa tgacgccgct ccatctaatg    180
```

-continued

```
atggtgcagc cggcctcgtg ccagaaagta acaatgaggt tatggctctt gaacctgttg    240

ctggggcatc tttagctgcc cctgtgactg gtcaaactaa tataattgac ccatggatcg    300

gaatgaattt tgttcaagcc ccaaatggag aattcactgt ttccccaaga aattcccctg    360

gagaagtact cctaaatttg gaattgggtc ctgaattaaa cccttatctg gcacacctat    420

ct                                                                   422
```

<210> SEQ ID NO 61
<211> LENGTH: 422
<212> TYPE: DNA
<213> ORGANISM: Norwalk-like Virus (GII)

<400> SEQUENCE: 61

```
aatcagcaag ctggtcattg cagagctgaa ggaaggtggc atggattttt acgtgcccag     60

gcaagagcct atgttcagat ggatgaggtt ttcagatctg agcacgtggg agggcgatcg    120

caatctggct cccagttttg tgaatgaaga tggcgtcgaa tgacgccgct ccatctaatg    180

atggtgcagc cggcctcgtg ccagaaagta acaatgaggt tatggctctt gaacctgttg    240

ctggggcatc tttagctgcc cctgtgactg gtcaaactaa tataattgac ccatggatca    300

gaatgaattt tgttcaagcc ccaaatggag aattcactgt ttccccaaga aattcccctg    360

gagaagtact cctaaatttg gaattgggtc ctgaattaaa cccttatctg gcacacctat    420

ct                                                                   422
```

<210> SEQ ID NO 62
<211> LENGTH: 416
<212> TYPE: DNA
<213> ORGANISM: Norwalk-like Virus (GII)

<400> SEQUENCE: 62

```
agatagcaaa ttagttatca ctgagctcaa agagggtggg atggatttct ttgtaccaag     60

acaggaaccc atgttcagat ggatgagatt ctcagacctc agtacttggg agggcgatcg    120

caatcttgct cccgaaggtg tgaatgaaga tggcgtcgaa tgacgctgct ccatctaatg    180

atggtgccgc cggcctcgtc ccagagatca acaatgaggc aatggcgcta gacccagtgg    240

cgggtgcagc aatagcagca ccccttactg gccagcaaaa tataattgat ccctggatta    300

tgaataactt tgtgcaagca cctggtggtg agttcacagt gtcacctaga aattctcctg    360

gtgaagtgtt acttaatttg gaattgggtc cagaaataaa tccctacttg gcccat        416
```

<210> SEQ ID NO 63
<211> LENGTH: 418
<212> TYPE: DNA
<213> ORGANISM: Norwalk-like Virus (GII)

<400> SEQUENCE: 63

```
ggacagtaag atggttatca gtgagatcaa gagtggtggt ctggagtttt ttgtgcccag     60

acaagaggcc atgtttaggt ggatgagatt ctctgacctc agcacatggg agggcgatcg    120

caatcttgct cccgagagtg tgaatgaaga tggcgtcgaa tgacgctgct ccatcgaatg    180

atggtgctgc caacctcgta ccagaggcca acaatgaggt tatggcactt gaaccggtgg    240

tgggagcctc aattgcagct cctgtcgtcg gtcaacaaaa tataattgac ccctggatta    300

gagaaaattt tgttcaggca ccacagggtg agtttactgt ttcaccaaga aactcgcctg    360

gtgagatgct tttaaatctt gaattaggcc cagagctcaa tccttacctg agtcattt      418
```

-continued

<210> SEQ ID NO 64
<211> LENGTH: 418
<212> TYPE: DNA
<213> ORGANISM: Norwalk-like Virus (GII)

<400> SEQUENCE: 64

```
ggacagtaag atggttatca gtgagatcaa gagtggtggt ctggagtttt ttgtgcccag     60

acaagaggcc atgtttaggt ggatgagatt ctctgacctc agcacatggg agggcgatcg    120

caatcttgct cccgagagtg tgaatgaaga tggcgtcgaa tgacgctgct ccatcgaatg    180

atggtgctgc caacctcgta ccagaggcca acaatgaggt tatggcactt gaaccggtgg    240

tgggagcctc aattgcagct cctgtcgtcg gtcaacaaaa tataattgac ccctggatta    300

gagaaaattt tgttcaggca ccacagggtg agtttactgt ttcaccaaga aactcgcctg    360

gtgagatgct tttaaatctt gaattaggcc cagagctcaa tccttacctg agtcattt      418
```

<210> SEQ ID NO 65
<211> LENGTH: 418
<212> TYPE: DNA
<213> ORGANISM: Norwalk-like Virus (GII)

<400> SEQUENCE: 65

```
ggacagtaag atggttatca gtgagatcaa gagtggtggt ctggagtttt ttgtgcccag     60

acaagaggcc atgtttaggt ggatgagatt ctctgacctc agcacatggg agggcgatcg    120

caatcttgct cccgagagtg tgaatgaaga tggcgtcgaa tgacgctgct ccatcgaatg    180

atggtgctgc caacctcgta ccagaggcca acaatgaggt tatggcactt gaaccggtgg    240

tgggagcctc aattgcagct cctgtcgtcg gtcaacaaaa tataattgac ccctggatta    300

gagaaaattt tgttcaggca ccacagggtg agtttactgt ttcaccaaga aactcgcctg    360

gtgagatgct tttaaatctt gaattaggcc cagagctcaa tccttacctg agtcattt      418
```

<210> SEQ ID NO 66
<211> LENGTH: 418
<212> TYPE: DNA
<213> ORGANISM: Norwalk-like Virus (GII)

<400> SEQUENCE: 66

```
aatcagcaag ctggtcatca cagaactaaa ggaaggtggc atggattttt tcgtgcccag     60

gcaagagccc atgtttaggt ggatgagatt ctcagacttg agcacgtggg agggcgatcg    120

caatctggct cccagttttg tgaatgaaga tggcgtcgaa tgacgccgct ccatctactg    180

atggtgcagc cggcctcgtg ccagaaagta ataatgaggt catggctctt gaacccgtgg    240

ctggtgccgc tttggcagcc ccggtcaccg gccaaacaaa tattatagac ccttggatta    300

gagcaaattt tgtccaggcc cctaatggtg aatttacagt ttctccccgt aatgcccctg    360

gtgaagtgct attgaatcta gagttgggtc cagaattaaa tccttatctg gcacattt      418
```

<210> SEQ ID NO 67
<211> LENGTH: 422
<212> TYPE: DNA
<213> ORGANISM: Norwalk-like Virus (GII)

<400> SEQUENCE: 67

```
gattagtaaa ttggtcataa ctgaactcaa agaaggtggg atggattttt tcgtgccaag     60

gcaggaacct atgttcaggt ggatgaggtt ttctgacttg agcacgtggg agggcgatcg    120

caatctggct cccagttttg tgaatgaaga tggcgtcgaa tgacgccgct ccatctactg    180
```

-continued

```
atggtgcagc cggcctcgta ccagaggtca acaacgagac aatggcactt gaaccagttg    240

cgggagcttc aatcgctgcc cccttaactg gtcaaaacaa tgtaatagac ccctggatta    300

gattaaattt tgtacaagcc cccaatggtg agttcacggt ttccccccga aactcgcctg    360

gtgaaatttt gttaaatttg gagttaggac ctgaattgaa cccatattta gcccatttag    420

ca                                                                    422
```

<210> SEQ ID NO 68
<211> LENGTH: 422
<212> TYPE: DNA
<213> ORGANISM: Norwalk-like Virus (GII)

<400> SEQUENCE: 68

```
gattagtaaa ttggtcataa ctgaactcaa agaaggtggg atggattttt tcgtgccaag     60

gcaggaacct atgttcaggt ggatgaggtt ttctgacttg agcacgtggg agggcgatcg    120

caatctggct cccagttttg tgaatgaaga tggcgtcgaa tgacgccgct ccatctactg    180

atggtgcagc cggcctcgta ccagaggtca acaacgagac aatggcactt gaaccagttg    240

cgggagcttc aatcgctgcc cccttaactg gtcaaaacaa tgtaatagac ccctggacta    300

gattaaatct tgtacaagcc cccaatggtg agttcacggt ttccccccga aactcgcctg    360

gtgaaatttt gttaaatttg gagttaggac ctgaattgaa cccatattta gcccatttag    420

ca                                                                    422
```

<210> SEQ ID NO 69
<211> LENGTH: 422
<212> TYPE: DNA
<213> ORGANISM: Norwalk-like Virus (GII)

<400> SEQUENCE: 69

```
ggtcagtaag atggttatca gtgagatcaa gagtggtggt ctggagtttt ttgtgcccag     60

acaagaggcc atgtttaggt ggatgagatt ctctgacctc agcacatggg agggcgatcg    120

caatcttgct cccgagagtg tgaatgaaga tggcgtcgaa tgacgctgct ccatcgaatg    180

atggtgctgc caacctcgta ccagaggcca acaatgaggt tatggcactt gaaccggtgg    240

tgggagcctc aattgcagct cctgtcgtcg gtcaacaaaa tataattgac ccctggatta    300

gagaaaattc tgttcaggca ccacagggtg agtttactgt ttcaccaaga aactcgcctg    360

gtgagatgct tttaaatctt gaattaggcc cagagctcaa tccttacctg agtcatttat    420

cc                                                                    422
```

<210> SEQ ID NO 70
<211> LENGTH: 422
<212> TYPE: DNA
<213> ORGANISM: Norwalk-like Virus (GII)

<400> SEQUENCE: 70

```
gattagtaaa ttggtcataa ctgaactcaa agaaggtggg atggattttt tcgtgccaag     60

gcaggaacct atgttcaggt ggatgaggtt ttctgacttg agcacgtggg agggcgatcg    120

caatctggct cccagttttg tgaatgaaga tggcgtcgaa tgacgccgct ccatctactg    180

atggtgcagc cggcctcgta ccagaggtca acaacgagac aatggcactt gaaccagttg    240

cgggagcttc aatcgctgcc cccttaactg gtcaaaacaa tgtaatagac ccctggatta    300

gattaaattt tgtacaagcc cccaatggtg agttcacggt ttccccccga aactcgcctg    360
```

-continued gtgaaatttt gttaaatttg gagttaggac ctgaattgaa cccatattta gcccatttag 420
ca 422

<210> SEQ ID NO 71
<211> LENGTH: 410
<212> TYPE: DNA
<213> ORGANISM: Norwalk-like Virus (GII)

<400> SEQUENCE: 71
aattagcaag ttagttattg cagagctaaa agaaggtggc atggattttt tcgtgcccag 60
acaagagcca atgttcagat ggatgagatt ctcagatctg agcacgtggg agggcgatcg 120
caatctggct cccagttttg tgaatgaaga tggcgtcgaa tgacgccaac ccatctgatg 180
ggtccacagc caacctcgtc ccagaggtca acaatgaggt tatggctttg gagcccgttg 240
ttggtgccgc tattgcggca cctgtagcgg gccaacaaaa tgtaattgac ccctggatta 300
gaaataattt tgtacaagcc cctggtggag agtttacagt atcccctaga aacgctccgg 360
gtgagatact atggagcgcg cccttgggcc ctgatttgaa cccctacctt 410

<210> SEQ ID NO 72
<211> LENGTH: 422
<212> TYPE: DNA
<213> ORGANISM: Norwalk-like Virus (GII)

<400> SEQUENCE: 72
attaagcaag ttagttattg cagagctaaa agaaggtggc atggattttt tcgtgcccag 60
acaagagcca atgttcagat ggatgagatt ctcagatctg agcacgtggg agggcgatcg 120
caatctggct cccagttttg tgaatgaaga tggcgtcgaa tgacgccaac ccatctgatg 180
ggtccacagc caacctcgtc ccagaggtca acaatgaggt tatggctttg gagcccgttg 240
ttggtgccgc tattgcggca cctgtagcgg gccaacaaaa tgtaattgac ccctggatta 300
gaaataattt tgtacaagcc cctggtggag agtttacagt atcccctaga aacgctccgg 360
gtgagatact atggagcgcg cccttgggcc ctgatttgaa cccctacctt tctcatttgg 420
cc 422

<210> SEQ ID NO 73
<211> LENGTH: 422
<212> TYPE: DNA
<213> ORGANISM: Norwalk-like Virus (GII)

<400> SEQUENCE: 73
ggacagtaag atggttatca gtgagatcaa gagtggtggt ctggagtttt ttgtgcccag 60
acaagaggcc atgtttaggt ggatgagatt ctctgacctc agcacatggg agggcgatcg 120
caatcttgct cccgagagtg tgaatgaaga tggcgtcgaa tgacgctgct ccatcgaatg 180
atggtgctgc caacctcgta ccagaggcca acaatgaggt tatggcactt gaaccggtgg 240
tgggagcctc aattgcagct cctgtcgtcg gtcaacaaaa tataattgac ccctggatta 300
gagaaaattt tgttcaggca ccacagggtg agtttactgt ttcaccaaga aactcgcctg 360
gtgagatgct tttaaatctt gaattaggcc cagagctcaa tccttacctg agtcatttat 420
cc 422

<210> SEQ ID NO 74
<211> LENGTH: 422
<212> TYPE: DNA
<213> ORGANISM: Norwalk-like Virus (GII)

-continued

<400> SEQUENCE: 74
aatcagcaag ctggttatca cagaactaaa ggaaggtggc atggattttt tcgtgcccag 60
gcaagagccc atgtttaggt ggatgagatt ctcagacttg agcacgtggg agggcgatcg 120
caatctggct cccagttttg tgaatgaaga tggcgtcgaa tgacgccgct ccatctactg 180
atggtgcagc cggcctcgtg ccagaaagta ataatgaggt catggctctt gaacccgtgg 240
ctggtgccgc tttggcagcc ccggtcaccg gccaaacaaa tattatagac ccttggatta 300
gagcaaattt tgtccaggcc cctaatggtg aatttacagt ttctccccgt aatgcccctg 360
gtgaagtgct attgaatcta gagttgggtc cagaattaaa tccttatctg gcacatttag 420
ca 422

<210> SEQ ID NO 75
<211> LENGTH: 422
<212> TYPE: DNA
<213> ORGANISM: Norwalk-like Virus (GII)

<400> SEQUENCE: 75
aatcagcaag ctggttatca cagaactaaa ggaaggtggc atggattttt tcgtgcccag 60
gcaagagccc atgtttaggt ggatgagatt ctcagacttg agcacgtggg agggcgatcg 120
caatctggct cccagttttg tgaatgaaga tggcgtcgaa tgacgccgct ccatctactg 180
atggtgcagc cggcctcgtg ccagaaagta ataatgaggt catggctctt gaacccgtgg 240
ctggtgccgc tttggcagcc ccggtcaccg gccaaacaaa tattatagac ccttggatta 300
gagcaaattt tgtccaggcc cctaatggtg aatttacagt ttctccccgt aatgcccctg 360
gtgaagtgct attgaatcta gagttgggtc cagaattaaa tccttatctg gcacatttag 420
ca 422

<210> SEQ ID NO 76
<211> LENGTH: 422
<212> TYPE: DNA
<213> ORGANISM: Norwalk-like Virus (GII)

<400> SEQUENCE: 76
ggtcagcaag ctggttatat ctgaacttaa ggagggagga atggattttt ttgtgcccag 60
acaagagtca atgtttaggt ggatgaggtt ctcagatcta agcacatggg agggcgatcg 120
caatctggct cccagttttg tgaatgaaga tggcgtcgaa tgacgctgct ccatctaatg 180
atggtgccgc cggcctcgtc ccagagatca acaatgaggc aatggcgcta gagccagtgg 240
cgggtgcagc gatagcagcg cccctcactg gccagcaaaa tataattgat ccctggatta 300
tgaataattt tgtgcaagca cctggtggtg agtttacagt gtcacctagg aattctcctg 360
gtgaagtgct tctcaatttg gaattaggtc cagaaataaa tccctatttg gctcatcttg 420
ct 422

<210> SEQ ID NO 77
<211> LENGTH: 422
<212> TYPE: DNA
<213> ORGANISM: Norwalk-like Virus (GII)

<400> SEQUENCE: 77
agttagcaaa ttagttatca ctgagctcaa agagggtggg atggatttct ttgtaccaag 60
acaggaaccc atgttcagat ggatgagatt ctcagacctc agtacttggg agggcgatcg 120

-continued

```
caatcttgct cccgaaggtg tgaatgaaga tggcgtcgaa tgacgctgct ccatctaatg    180

atggtgccgc cggcctcgtc ccagagatca acaatgaggc aatggcgcta gacccagtgg    240

cgggtgcagc gatagcagcg cccctcactg gccagcaaaa tataattgat ccctggatta    300

tgaataactt tgtgcaagca cctggtggtg agttcacagt gtcacctaga aattctcctg    360

gtgaagtgtt acttaatttg gaattgggtc cagaaataaa tccctacttg gcccatcttg    420

ct                                                                   422

<210> SEQ ID NO 78
<211> LENGTH: 422
<212> TYPE: DNA
<213> ORGANISM: Norwalk-like Virus (GII)

<400> SEQUENCE: 78

aatcagcaag ctggttatca cagaactaaa ggaaggtggc atggattttt tcgtgcccag     60

gcaagagccc atgtttaggt ggatgagatt ctcagacttg agcacgtggg agggcgatcg    120

caatctggct cccagttttg tgaatgaaga tggcgtcgaa tgacgccgct ccatctactg    180

atggtgcagc cggcctcgtg ccagaaagta ataatgaggt catggctctt gaacccgtgg    240

ctggtgccgc tttggcagcc ccggtcaccg gccaaacaaa tattatagac ccttggatta    300

gagcaaattt tgtccaggcc cctaatggtg aatttacagt ttctccccgt aatgcccctg    360

gtgaagtgct attgaatcta gagttgggtc cagaattaaa tccttatctg gcacatttag    420

ca                                                                   422

<210> SEQ ID NO 79
<211> LENGTH: 422
<212> TYPE: DNA
<213> ORGANISM: Norwalk-like Virus (GII)

<400> SEQUENCE: 79

aatcagcaag ctggtcatca cagaactaaa ggaaggtggc atggattttt tcgtgcccag     60

gcaagagccc atgtttaggt ggatgagatt ctcagacttg agcacgtggg agggcgatcg    120

caatctggct cccagttttg tgaatgaaga tggcgtcgaa tgacgccgct ccatctactg    180

atggtgcagc cggcctcgtg ccagaaagta ataatgaggt catggctctt gaacccgtgg    240

ctggtgccgc tttggcagcc ccggtcaccg gccaaacaaa tattatagac ccttggatta    300

gagcaaattt tgtccaggcc cctaatggtg aatttacagt ttctccccgt aatgcccctg    360

gtgaagtgct attgaatcta gagttgggtc cagaattaaa tccttatctg gcacatttag    420

ca                                                                   422

<210> SEQ ID NO 80
<211> LENGTH: 422
<212> TYPE: DNA
<213> ORGANISM: Norwalk-like Virus (GII)

<400> SEQUENCE: 80

aatcagcaag ctggtcatca cagaactaaa ggaaggtggc atggattttt tcgtgcccag     60

gcaagagccc atgtttaggt ggatgagatt ctcagacttg agcacgtggg agggcgatcg    120

caatctggct cccagttttg tgaatgaaga tggcgtcgaa tgacgccgct ccatctactg    180

atggtgcagc cggcctcgtg ccagaaagta ataatgaggt catggctctt gaacccgtgg    240

ctggtgccgc tttggcagcc ccggtcaccg gccaaacaaa tattatagac ccttggatta    300
```

-continued

```
gagcaaattt tgtccaggcc cctaatggtg aatttacagt ttctccccgt aatgcccctg    360

gtgaagtgct attgaatcta gagttgggtc cagaattaaa tccttatctg gcacatttag    420

ca                                                                   422
```

<210> SEQ ID NO 81
<211> LENGTH: 296
<212> TYPE: DNA
<213> ORGANISM: Norwalk-like Virus (GII)

<400> SEQUENCE: 81

```
tgctcccgaa ggtgtgaatg aagatggcgt cgaatgacgc tgctccatct aatgatggtg     60

ccgccggcct cgtcccagag atcaacaatg aggcaatggc gctagaccca gtggcgggtg    120

cagcaatagc agcacccctt actggccagc aaaatataat tgatccctgg attatgaata    180

actttgtgca agcacctggt ggtgagttca cagtgtcacc tagaaattct cctggtgaag    240

tgttacttaa tttggaattg ggtccagaaa taaatcccta cttggcccat cttgct        296
```

<210> SEQ ID NO 82
<211> LENGTH: 296
<212> TYPE: DNA
<213> ORGANISM: Norwalk-like Virus (GII)

<400> SEQUENCE: 82

```
tgctcccgaa ggtgtgaatg aagatggcgt cgaatgacgc tgctccatct aatgatggtg     60

ccgccggcct cgtcccagag atcaacaatg aggcaatggc gctagaccca gtggcgggtg    120

cagcaatagc agcacccctt actggccagc aaaatataat tgatccctgg attatgaata    180

actttgtgca agcacctggt ggtgagttca cagtgtcacc tagaaattct cctggtgaag    240

tgttacttaa tttggaattg ggtccagaaa taaatcccta cttggcccat cttgct        296
```

<210> SEQ ID NO 83
<211> LENGTH: 296
<212> TYPE: DNA
<213> ORGANISM: Norwalk-like Virus (GII)

<400> SEQUENCE: 83

```
tgctcccgaa ggtgtgaatg aagatggcgt cgaatgacgc tgctccatct aatgatggtg     60

ccgccggcct cgtcccagag atcaacaatg aggcaatggc gctagaccca gtggcgggtg    120

cagcaatagc agcacccctt actggccagc aaaatataat tgatccctgg attatgaata    180

actttgtgca agcacctggt ggtgagttca cagtgtcacc tagaaattct cctggtgaag    240

tgttacttaa tttggaattg ggtccagaaa taaatcccta cttggcccat cttgct        296
```

<210> SEQ ID NO 84
<211> LENGTH: 403
<212> TYPE: DNA
<213> ORGANISM: Norwalk-like Virus (GII)

<400> SEQUENCE: 84

```
tgggagggcg atcgcaatct ggctcccagt tttgtgaatg aagatggcgt cgaatgacgc     60

tgctccatct aatgatggtg ccgccggcct cgtcccagag atcaacaatg aggcaatggc    120

gctagaccca gtggcgggtg cagcgatagc agcgcccctc actggccagc aaaatataat    180

tgatccctgg attatgaata actttgtgca agcacctggt ggtgagttca cagtgtcacc    240

taggaattcc cctggtgaag tgcttcttaa tttggagtta ggtccagaaa taaaccccta    300

tttggctcac cttgctagaa tgtacaatgg ttatgcaggt ggatttgaag tgcaagtggt    360
```

-continued cctagctgga aatgcgttta cagcaggaaa ggttatcttt gca 403

<210> SEQ ID NO 85
<211> LENGTH: 384
<212> TYPE: DNA
<213> ORGANISM: Norwalk-like Virus (GII)

<400> SEQUENCE: 85
tggctcccag ttttgtgaat gaagatggcg tcgaatgacg ccgctccatc tactgatggt 60
gcagccggcc tcgtgccaga aagtaataat gaggtcatgg ctcttgagcc cgtggctggt 120
gctgccttgg cagccccggt caccggtcaa acaaatatta tagacccttg gattagagca 180
aattttgtcc aggcccctaa tggtgaattt acagtttctc cccgtaatgc ccctggtgaa 240
gtgctattaa atctagaatt gggtccagaa ttaaatcctt atctggcaca tttagcaaga 300
atgtacaacg ggtatgccgg tgggatggag gtgcaggtca tgctagctgg gaacgcgttc 360
acagctggca aattggtctt cgct 384

<210> SEQ ID NO 86
<211> LENGTH: 366
<212> TYPE: DNA
<213> ORGANISM: Norwalk-like Virus (GII)

<400> SEQUENCE: 86
atgaagatgg cgtcgaatga cgccgctcca tctaatgatg gtgcagccgg tcttgtacca 60
gaggctaaca atgagaccat ggcacttgaa ccggtggctg gggcttcaat agccgcccca 120
ctcaccggcc aaaacaatat tatagacccc tggattagat taaattttgt gcaggctccc 180
aatggagagt tcacggtttc accccgcaac tcacccgggg aagtcctatt aaatttggaa 240
ttaggccccg aactaaatcc atacctagca cacctttcta gaatgtataa tggttatgca 300
ggtggggttg aggtgcaagt actactggct gggaatgcgt tcacagctgg aaaattggtg 360
tttgcc 366

<210> SEQ ID NO 87
<211> LENGTH: 366
<212> TYPE: DNA
<213> ORGANISM: Norwalk-like Virus (GII)

<400> SEQUENCE: 87
atgaagatgg cgtcgaatga cgccaaccca tctgatgggt ccacagccaa cctcgtccca 60
gaggtcaaca atgaggttat ggctttggag cccgttgttg gtgccgctat tgcggcacct 120
gtagcgggcc aacaaaatgt aattgacccc tggattagaa ataattttgt acaagcccct 180
ggtggagagt ttacagtatc ccctagaaac gctccgggtg agatactatg gagcgcgccc 240
ttaggccctg atttgaaccc ctacctttct catttggcca gaatgtacaa tggttatgca 300
ggtggttttg aagtgcaggt aatcctcgcg gggaacgcgt tcaccgccgg gaaaatcata 360
tttgca 366

<210> SEQ ID NO 88
<211> LENGTH: 366
<212> TYPE: DNA
<213> ORGANISM: Norwalk-like Virus (GII)

<400> SEQUENCE: 88
atgaagatgg cgtcgaatga cgccaaccca tctgatgggt ccacagccaa cctcgtccca 60

-continued gaggtcaaca atgaggttat ggctttggag cccgttgtcg gtgccgctat tgcggcacct 120
gtagcgggcc aacaaaatgt aattgacccc tggattagaa ataattttgt acaagcccct 180
ggtggagagt ttacagtatc ccctagaaac gctccgggtg agatactatg gagcgcgccc 240
ttgggccctg atttgaaccc ctacctttct catttggcca gaatgtacaa tggttatgca 300
ggtggttttg aagtgcaggt aatcctcgcg gggaacgcgt tcaccgccgg gaaaatcata 360
tttgca 366

<210> SEQ ID NO 89
<211> LENGTH: 366
<212> TYPE: DNA
<213> ORGANISM: Norwalk-like Virus (GII)

<400> SEQUENCE: 89
atgaagatgg cgtcgaatga cgccaaccca tctgatgggt ccacagccaa cctcgtccca 60
gaggtcaaca atgaggttat ggctttggag cccgttgttg gtgccgctat tgcggcacct 120
gtagcgggcc aacaaaatgt aattgacccc tggattagaa ataattttgt acaagcccct 180
ggtggagagt ttacagtatc ccctagaaac gctccgggtg agatactatg gagcgcgccc 240
ttgggccctg atttgaaccc ttacctttct catttggcca gaatgtacaa tggttatgca 300
ggtggttttg aagtgcaggt aatcctcgcg gggaacgcgt tcaccgccgg gaaaatcata 360
tttgca 366

<210> SEQ ID NO 90
<211> LENGTH: 366
<212> TYPE: DNA
<213> ORGANISM: Norwalk-like Virus (GII)

<400> SEQUENCE: 90
atgaagatgg cgtcgaatga cgccaaccca tctgatgggt ccacagccaa cctcgtccca 60
gaggtcaaca atgaggttat ggctttggag cccgttgttg gtgccgctat tgcggcacct 120
gtagcgggcc aacaaaatgt aattgacccc tggattagaa ataattttgt acaagcccct 180
ggtggagagt ttacagtatc ccctagaaac gctccgggtg agatactatg gagcgcgccc 240
ttaggccctg atttgaaccc ctacctttct catttggcca gaatgtacaa tggttatgca 300
ggtggttttg aagtgcaggt aatcctcgcg gggaacgcgt tcaccgccgg gaaaatcata 360
tttgca 366

<210> SEQ ID NO 91
<211> LENGTH: 366
<212> TYPE: DNA
<213> ORGANISM: Norwalk-like Virus (GII)

<400> SEQUENCE: 91
atgaagatgg cgtcgaatga cgccaaccca tctgatgggt ccacagccaa cctcgtccca 60
gaggtcaaca atgaggttat ggctttggag cccgttgttg gtgccgctat tgcggcacct 120
gtagcgggcc aacaaaatgt aattgacccc tggattagaa ataattttgt acaagcccct 180
ggtggagagt ttacagtatc ccctagaaac gctccgggtg agatactatg gagcgcgccc 240
ttaggccctg atttgaaccc ctacctttct catttggcca gaatgtacaa tggttatgca 300
ggtggttttg aagtgcaggt aatcctcgcg gggaacgcgt tcaccgccgg gaaaatcata 360
tttgca 366

-continued

<210> SEQ ID NO 92
<211> LENGTH: 366
<212> TYPE: DNA
<213> ORGANISM: Norwalk-like Virus (GII)

<400> SEQUENCE: 92
atgaagatgg cgtcgaatga cgccaaccca tctgatgggt ccacagccaa cctcgtccca 60
gaggtcaaca atgaggttat ggctttggag cccgttgttg gtgccgctat tgcggcacct 120
gtagcgggcc aacaaaatgt aattgacccc tggattagaa ataattttgt gcaagcccct 180
ggtggagagt ttacagtatc ccctagaaac gctccgggtg agatactatg gagcgcgccc 240
ttaggccctg atttgaaccc ctacctttct catttggcca gaatgtacaa tggttatgca 300
ggtggttttg aagtgcaagt aatcctcgcg gggaacgcgt tcaccgccgg gaaaatcata 360
tttgca 366

<210> SEQ ID NO 93
<211> LENGTH: 366
<212> TYPE: DNA
<213> ORGANISM: Norwalk-like Virus (GII)

<400> SEQUENCE: 93
atgaagatgg cgtcgaatga cgccaaccca tctgatgggt caacagccaa cctcgtccca 60
gaggtcaaca atgaggttat ggctttggag cccgttgttg gtgccgctat tgcggcacct 120
gtagcgggcc aacaaaatgt aattgacccc tggattagaa ataattttgt acaagcccct 180
ggtggagagt ttacagtatc ccctagaaac gctccgggtg agatactatg gagcgcgccc 240
ttaggccctg atttgaaccc ctacctttct catttggcca gaatgtacaa tggttatgca 300
ggtggttttg aagtgcaggt aatcctcgcg gggaacgcgt tcaccgccgg gaaaatcata 360
tttgca 366

<210> SEQ ID NO 94
<211> LENGTH: 366
<212> TYPE: DNA
<213> ORGANISM: Norwalk-like Virus (GII)

<400> SEQUENCE: 94
atgaagatgg cgtcgaatga cgccaaccca tctgatgggt ccacagccaa cctcgtccca 60
gaggtcaaca atgaggttat ggctttggag cccgttgttg gtgccgctat tgcggcacct 120
gtagcgggcc aacaaaatgt aattgacccc tggattagaa ataattttgt acaagcccct 180
ggtggagagt ttacagtatc ccctagaaac gctccgggtg agatactatg gagcgcgccc 240
ttaggccctg atttgaaccc ctacctttct catttggcca gaatgtacaa tggttatgca 300
ggtggttttg aagtgcaggt aatcctcgcg gggaacgcgt tcaccgccgg gaaaatcata 360
tttgca 366

<210> SEQ ID NO 95
<211> LENGTH: 366
<212> TYPE: DNA
<213> ORGANISM: Norwalk-like Virus (GII)

<400> SEQUENCE: 95
atgaagatgg cgtcgaatga cgccaaccca tctgatgggt ccacagccaa cctcgtccca 60
gaggtcaaca atgaggttat ggctttggag cccgttgttg gtgccgctat tgcggcacct 120
gtagcgggcc aacaaaatgt aattgacccc tggattagaa ataattttgt acaagcccct 180

-continued

```
ggtggagagt ttacagtgtc ccctagaaac gctccgggtg agatactatg gagcgcgccc    240

ttaggccctg acttgaaccc ctacctttct catttggcca gaatgtacaa tggttatgca    300

ggtggttttg aagtgcaggt aatcctcgcg gggaacgcgt tcaccgccgg gaaaatcata    360

tttgca                                                               366
```

<210> SEQ ID NO 96
<211> LENGTH: 366
<212> TYPE: DNA
<213> ORGANISM: Norwalk-like Virus (GII)

<400> SEQUENCE: 96

```
atgaagatgg cgtcgaatga cgccaaccca tctgatgggt ccacagccaa cctcgtccca     60

gaggtcaaca atgaggttat ggctttggag cccgttgttg gtgccgccat tgcggcacct    120

gtagcgggcc aacaaaatgt aattgacccc tggattagaa ataattttgt acaagcccct    180

ggtggagagt ttacagtgtc ccctaggaac gctccgggtg agatactatg gagcgcgccc    240

ttgggccctg atttgaaccc ctacctttct cacttggcca gaatgtataa tggttatgca    300

ggtggttttg aagtgcaggt aatcctcgcg gggaacgcgt tcaccgccgg gaaaatcata    360

tttgca                                                               366
```

<210> SEQ ID NO 97
<211> LENGTH: 366
<212> TYPE: DNA
<213> ORGANISM: Norwalk-like Virus (GII)

<400> SEQUENCE: 97

```
atgaagatgg cgtcgaatga cgccaaccca tctgatgggt ccacagccaa cctcgtccca     60

gaagtcaaca atgaggttat ggctttggag cccgttgttg gtgccgctat tgcggcacct    120

gtagcgggcc aacaaaatgt aattgacccc tggattagaa ataattttgt acaagcccct    180

ggtggagagt ttacagtgtc ccctagaaac gctccgggtg aaatactatg gagcgcgccc    240

ttgggccctg atttgaaccc ctacctttcc catttggcca gaatgtacaa tggttatgca    300

ggtggttttg aagtgcaggt aatcctcgcg gggaacgcgt tcaccgccgg gaaaatcata    360

tttgca                                                               366
```

<210> SEQ ID NO 98
<211> LENGTH: 366
<212> TYPE: DNA
<213> ORGANISM: Norwalk-like Virus (GII)

<400> SEQUENCE: 98

```
atgaagatgg cgtcgagtga cgctgctcca tctgcggatg gtgcgggcaa cctcgtccca     60

gagagtcaac aagaggtatt gcccctcgcc cccgttgcgg gcgctgcact agcggcaccc    120

gtagtggggc agacaaacat aattgacccc tggattaaag aaaattttgt tcaagccccc    180

cagggtgagt ttacagtctc acctaaaaat tctcctggtg aaattttagt caatttggaa    240

ttgggaccca aactcaaccc ctatctggat cacctctcac gcatgtacaa ttcatatgct    300

ggtggtatag atgttatggt ggtgttggcg ggtaacgcct tcacagccgg taaggttcta    360

atagca                                                               366
```

<210> SEQ ID NO 99
<211> LENGTH: 366
<212> TYPE: DNA
<213> ORGANISM: Norwalk-like Virus (GII)

-continued

<400> SEQUENCE: 99
atgaagatgg cgtcgaatga cgcagctcca tcgaatgatg gcgcggctgg cctcgtacca 60
gagatcaacc atgaggtcat ggccatagaa cctgttgcag gggcctcttt agcagcccct 120
gtcgtaggac aacttaatat aattgatccc tggattagaa ataattttgt acaagcccct 180
gctggagaat ttactgtttc acctagaaat gctccgggtg aatttttgtt agatttagag 240
ctaggccctg aattaaaccc ctatcttgct caccttgcac gcatgtataa tgggcatgct 300
ggtggtatgg aggtgcagat agtgcttgct gggaatgcgt tcacagcggg caaaatcctg 360
tttgca 366

<210> SEQ ID NO 100
<211> LENGTH: 366
<212> TYPE: DNA
<213> ORGANISM: Norwalk-like Virus (GII)

<400> SEQUENCE: 100
atgaagatgg cgtcgaatga cgccaaccca tctgatgggt ccacagccaa cctcgtccca 60
gaggtcaaca atgaggttat ggctttggaa cccgttgttg gtgccgctat tgcggcacct 120
gtagcgggcc aacaaaatgt aattgacccc tggattagaa ataattttgt acaagcccct 180
ggtggagagt ttacagtatc ccctagaaac gctccgggtg agatactatg gagcgcgccc 240
ttgggccctg atttgaaccc ctacctttct catttggcca gaatgtacaa tggttatgca 300
ggtggttttg aagtgcaggt aatcctcgcg gggaacgcgt tcaccgccgg gaaaatcata 360
tttgca 366

<210> SEQ ID NO 101
<211> LENGTH: 366
<212> TYPE: DNA
<213> ORGANISM: Norwalk-like Virus (GII)
<220> FEATURE:
<221> NAME/KEY: misc_feature
<222> LOCATION: (61)..(61)
<223> OTHER INFORMATION: n is a, c, g, or t

<400> SEQUENCE: 101
atgaaratgg cgtcgaatga cgccgctcca tctaatgatg gtgcagccgg tctcgtacca 60
naggtcaaca acgaracrat ggcactcgaa ccggtggctg gggcttccat agccgcccct 120
ctaaccggtc aaaacaatgt gatagacccc tggattagaa tgaactttgt tcaagcccca 180
aatggtgaat ttacagtgtc tccccgtaac tctcctggtg aaattctgtt aaatttagaa 240
ttaggtcctg aattaaatcc attcttagca cacctttcaa ggatgtwtaa tggttatgct 300
ggtggggttg aaatgcaggt gctacttgct gggaacgcgt tcacagcagg aaaactactg 360
tttgca 366

<210> SEQ ID NO 102
<211> LENGTH: 366
<212> TYPE: DNA
<213> ORGANISM: Norwalk-like Virus (GII)

<400> SEQUENCE: 102
atgaagatgg cgtcgaatga cgctactcca tcaaatgatg gtgccgccgg cctcgtgcca 60
gaaagtaata atgaggcaat ggctctggaa cccgtggctg gggcgtcttt agccgcccct 120
gtcactggcc aaactaatat aatagacccc tggattagaa ctaattttgt ccaagcccct 180

-continued

```
aatggtgaat tcacagtttc ccctaaaaat tcccctggag agatattggt caatttggag    240

ttgggtccag aactgaaccc ttatctggca catttagcta ggatgtacaa tggttatgcg    300

ggtggtatgg aggtgcaagt gatgcttgcg ggaacgcgt tcactgctgg caagatcatc    360

tttgcc                                                               366
```

<210> SEQ ID NO 103
<211> LENGTH: 366
<212> TYPE: DNA
<213> ORGANISM: Norwalk-like Virus (GII)

<400> SEQUENCE: 103

```
atgaagatgg cgtcgaatga cgcagctcca tctaatgatg gtgcagcagg cctcgtacca     60

garatcaaca atgaggtcat gcccccttgag cccgtggctg gtgcatcgct ggcgacacca    120

gttgttgggc aacaaaacat aattgatccc tggataagaa ataattttgt gcaagcccct    180

gcaggtgagt ttacagtctc ccctaggaat tcccccggtg aaatcctgct tgatttagag    240

ttgggaccag aattgaaccc ctaccttgct catttggctc gtatgtataa tggacacgct    300

ggtggcatgg aagtgcaaat tgtgttggct gggaatgcgt tcacagctgg caagatcgta    360

tttgct                                                               366
```

<210> SEQ ID NO 104
<211> LENGTH: 366
<212> TYPE: DNA
<213> ORGANISM: Norwalk-like Virus (GII)

<400> SEQUENCE: 104

```
atgaagatgg cgtcgaatga cgctgctcca tctaatgatg gtgccgccgg cctcgctcca     60

gagatcaaca atgaggcaat ggcgctagag ccagtggcgg gtgcagcgat agcagcgccc    120

ctcactggcc agcaaaatat aattgatccc tggattatga ataattttgt gcaagcacct    180

ggtggtgagt ttacagtgtc acctaggaat tctcctggtg aagtgcttct taatttggaa    240

ttaggtccag aaataaatcc ctatttggct catcttgcta gaatgtacaa tggttatgca    300

ggtggatttg aagtgcaagt ggtcctagct ggaaatgcgc ttacagcagg aaagggtatc    360

tttgca                                                               366
```

<210> SEQ ID NO 105
<211> LENGTH: 366
<212> TYPE: DNA
<213> ORGANISM: Norwalk-like Virus (GII)

<400> SEQUENCE: 105

```
atgaagatgg cgtcgaatsa cgccaaccca tctgatgggt ccacagccaa cctcgtcyca     60

gaggtcaaca atgaggttat ggctttggag cccgttgttg gtgccgctat tgcagcacct    120

gtagcgggcc aacaaaatgt aattgacccc tggattagaa ataattttgt acaagcccct    180

ggtggagagt ttacagtatc ccctaaaaac gctccgggtg agatactatg gagcgcgccc    240

ttgggccctg atttgaaccc ctacctttct catttggcca gaatgtacaa tggttatgca    300

ggtggttttg aagtgcaggt aatcctcgcg gggaacgcgt tcaccgccgg gaaaatcata    360

tttgca                                                               366
```

<210> SEQ ID NO 106
<211> LENGTH: 366
<212> TYPE: DNA
<213> ORGANISM: Norwalk-like Virus (GII)

-continued

<400> SEQUENCE: 106
atgaagatgg cgtcgaatga cgctgctcca tctaatgatg gtgccgccgg cctcgtccca 60
gagatcaaca atgaggcaat ggcgctagag ccagtggcgg gtgcagcgat agcagcgccc 120
ctcactggcc agcaaaatat aattgatccc tggattatga ataattttgc gcaagcacct 180
ggtggtgagt ttacagtgtc acctaggaac tcccctggtg aagtgcttct taatttggaa 240
ttaggtccag aaataaatcc ctatttggct catcttgcta gaatgtacaa tggttatgca 300
ggtggatttg aagtgcaagt ggtcctagct ggaaatgcgt ttacagcagg aaaggttatc 360
tttgca 366

<210> SEQ ID NO 107
<211> LENGTH: 366
<212> TYPE: DNA
<213> ORGANISM: Norwalk-like Virus (GII)

<400> SEQUENCE: 107
atgaagatgg cgtcgagtga cgccgctcca tctaatgatg gtgcagccgg tctcgtacca 60
gaggctaacg wtgagaccat ggcacttgaa ccggtggctg gggcttcaat agccgcccca 120
ctcaccggcc aaaacaatat tatagacccc tggattarat taaactttgt gcaggctccc 180
aatggaragt tcacggtttc accccgcaac tcacctgggg aagtcctact aaatttggaa 240
ttaggccccg aactaaatcc atatctggca cacctttcta aaatgtataa tggttatgca 300
ggtggggttg aggtgcaagt actactggct gggwacgcgt tcacagctgg aaaattggtg 360
ttcgcc 366

<210> SEQ ID NO 108
<211> LENGTH: 366
<212> TYPE: DNA
<213> ORGANISM: Norwalk-like Virus (GII)

<400> SEQUENCE: 108
atgaagatgg cgtcgaatga cgccaaccca tctgatgggt ccacagccaa cctcgtccca 60
gaggtcaaca atgaggttat ggctttggag cccgttgttg gtgccgctat cgcggcacct 120
gtagcgggcc aacaaaatgt aattgacccc tggattagaa gtaattttgt acaagcccct 180
ggtggagagt ttacagtatc ccctagaaac gctccaggtg agatactatg gagcgcgccc 240
ttgggccctg atttgaaccc ctacctttct catttggcca gaatgtacaa tggttatgca 300
ggtggtcttg aagtgcaggt agtcctcgcg ggaaacgcgt tcaccgccgg gaaaatcata 360
tttgca 366

<210> SEQ ID NO 109
<211> LENGTH: 366
<212> TYPE: DNA
<213> ORGANISM: Norwalk-like Virus (GII)

<400> SEQUENCE: 109
atgaaratgg cgtcgaatga cgctgctcca tcgaatgatg gtgctgccaa cctcgtacca 60
gaggccagca atgaggttat ggcacttgaa ccggtggtgg gagcctcaat cgcagctcct 120
gttgtcggtc agcaaaatat aattgacccc tggattagag aaaattttgt ccaagcacca 180
cagggcgagt tcactgtttc accaaggaat tcgcctggtg agatgctctt aaaccttgag 240
ttgggcccag aacttaatcc ctatttgagt catttgtccc gcatgtacaa cggatatgct 300

-continued ggtggcatgc aggttcaggt ggtcctagct gggaatgcgt kcacagctgg gaaaatcatc 360
tttgcc 366

<210> SEQ ID NO 110
<211> LENGTH: 366
<212> TYPE: DNA
<213> ORGANISM: Norwalk-like Virus (GII)

<400> SEQUENCE: 110
atgaagatgg cgtcgaatga cgccgctcca tctactgatg gtgcagccgg cctcgtgcca 60
gaaagtaata atgaggtcat ggctcttgag cccgtggctg gtgctgcctt ggcagccccg 120
gtcaccggtc aaacaaatat tatagaccct tggattagag caaattttgt ccaggcccct 180
aatggcgaat ttacagtttc tccccgtaat gcccctggtg aagtgctatt aaatctagaa 240
ttgggtccag aattaaatcc ttatctggca catttagcaa gaatgtacaa cgggtatgcc 300
ggtgggatgg aggtgcaggt catgctagct gggaacgcgt tcacagctgg caaattggtc 360
ttcgct 366

<210> SEQ ID NO 111
<211> LENGTH: 345
<212> TYPE: DNA
<213> ORGANISM: Norwalk-like Virus (GII)

<400> SEQUENCE: 111
gctgctccgt ctaatgatgg tgctgccggc ctcgttccag agatcaacaa tgaggcaatg 60
gcgctagagc cagtagcggg tgcagcaata gcagcacccc tcactggtca gcaaaatata 120
attgatccct ggattatgaa taattttgtg caggcacctg gtggtgagtt tacagtgtca 180
cccagaaact cccctggtga agtgcttctt aatttagaat taggtccaga aataaatccc 240
tatttggctc accttgctag aatgtacaat ggttatgcag gcgggtttga agtgcaggta 300
gtcctggctg gtaatgcgtt cacagcagga aagataatct ttgca 345

<210> SEQ ID NO 112
<211> LENGTH: 345
<212> TYPE: DNA
<213> ORGANISM: Norwalk-like Virus (GII)

<400> SEQUENCE: 112
gctgctccgt ctaacgatgg tgccgccggc ctcgtcccag agatcaacaa tgaggcaatg 60
gcgctagacc cagtggcggg tgcagcgata gcagcgcccc tcactggaca gcaaaacata 120
attgatccct ggattatgaa taattttgtg caagcacctg gtggtgagtt tacagtgtca 180
cctaggaatt cccctggtga agtgcttcta aatttagaat taggcccaga aataaacccc 240
tatctggctc accttgctag gatgtacaat ggttatgcag gtggatttga agtgcaggta 300
gtcctggctg gaaatgcgtt tacagcagga aaggtgatct ttgca 345

<210> SEQ ID NO 113
<211> LENGTH: 345
<212> TYPE: DNA
<213> ORGANISM: Norwalk-like Virus (GII)

<400> SEQUENCE: 113
gctactccat caaatgatgg tgccgccggc ctcgtgccag aaagtaataa tgaggcaatg 60
gctctggaac ccgtggtggg ggcgtcttta gccgcccctg tcactggcca aactaatata 120
atagacccct ggattagaac taattttgtc caagccccta atggtgaatt cacagtctcc 180

```
cctagaaatt cccctggaga gatattggtc aatttggagt tgggtccaga actgaaccct    240

tatctggcac atttagctag gatgtacaat ggttatgcgg gtggtatgga ggtgcaagag    300

atgctcgcgg ggaacgcgtt cactgctggc aagatcatct ttgcc                    345


<210> SEQ ID NO 114
<211> LENGTH: 345
<212> TYPE: DNA
<213> ORGANISM: Norwalk-like Virus (GII)

<400> SEQUENCE: 114

gccgctccat ctaatgatgg tgcagccggt ctcgtgccag aggtcaacaa cgagacgatg     60

gcactcgaac cggtggctgg ggcttccata gccgcccctc taaccggtca aaacaatgtg    120

atagacccct ggattaggat gaactttgtt caagccccaa atggtgaatt tacagtatct    180

ccccgtaatt ctcctggtga aattctgtta aatttagaat taggtcctga attaaatcca    240

ttcttagcac acctttcaag gatgtacaat ggttatgctg gcggggttga agtgcaggtg    300

ctacttgctg ggaacgcgtt cacagcagga aaactagtgt ttgca                    345


<210> SEQ ID NO 115
<211> LENGTH: 345
<212> TYPE: DNA
<213> ORGANISM: Norwalk-like Virus (GII)

<400> SEQUENCE: 115

gctactccat caaatgatgg tgccgccggc ctcgtgccag aaagtaataa tgaggcaatg     60

gctctggaac ccgtggtggg ggcgtcttta gccgcccctg tcactggcca aactaatata    120

atagacccct ggattagaac taattttgtc caagccccta atggtgaatt cacagtctcc    180

cctagaaatt cccctgggga gatatcggtc aatttggagt tgggtccaga actggaccct    240

tatctggcac atttagctag gatgtacaat ggttatgcgg gtggtatgga ggtgcaagtg    300

atgctcgcgg ggaacgcgtt cactgctggc aaggtcatct ttgcc                    345


<210> SEQ ID NO 116
<211> LENGTH: 345
<212> TYPE: DNA
<213> ORGANISM: Norwalk-like Virus (GII)

<400> SEQUENCE: 116

gctactccat caaatgatgg tgccgccggc ctcgtgccag aaagtaataa tgaggcaatg     60

gctctggaac ccgtggtggg ggcgtcttta gccgcccctg tcactggcca aactaatata    120

atagacccct ggattagaac taattttgtc caagcccccca atggtgaatt tacagtttcc    180

cctagaaatt cccctggaga gatattggtc aatttggagt tgggtccaga actgaaccct    240

tatctggcac atttagctag gatgtacaat ggttatgcgg gtggtatgga agtgcaagtg    300

atgctcgcgg ggaacgcgtt cactgctggc aagatcatct ttgcc                    345


<210> SEQ ID NO 117
<211> LENGTH: 345
<212> TYPE: DNA
<213> ORGANISM: Norwalk-like Virus (GII)

<400> SEQUENCE: 117

gctgctccgt ctaacgatgg tgccgccggc ctcgtcccag agatcaacaa tgaggcaatg     60

gcgctagagc cagtggcagg tgcagcaata gcagcacctc tcactggcca gcaaaatata    120
```

-continued

```
attgatccct ggattatgaa taactttgtg caagcacctg gtggtgagtt tacagtgtca    180

cctaggaact cccctggtga agtacttctc aatttagaat taggtccaga aataaaccct    240

tatttggctc accttgctag gatgtacaat ggttatgcag gtgggtttga ggtgcaggta    300

gtcctggctg gaaatgcgtt tacagcagga aaggtgatct ttgca                    345
```

<210> SEQ ID NO 118
<211> LENGTH: 343
<212> TYPE: DNA
<213> ORGANISM: Norwalk-like Virus (GII)

<400> SEQUENCE: 118

```
tgctccatct aatgatggtg ccgccggcct cgtcccagag atcaacaatg aggcaatggc     60

gctagaccca gtggcgggtg cagcgatagc agcacccctc actggtcagc aaaacataat    120

tgatccctgg attatgaata attttgtgca agcacctggt ggtgagttta cagtgtcccc    180

taggaattcc cctggtgaag tgcttcttaa tttggaattg ggcccagaaa taaaccctta    240

tttggcccat cttgctagaa tgtataatgg ttatgcaggt ggatttgaag tgcaggtggt    300

cctggctggg aatgcgttca cagcaggaaa gataatcttt gca                      343
```

<210> SEQ ID NO 119
<211> LENGTH: 343
<212> TYPE: DNA
<213> ORGANISM: Norwalk-like Virus (GII)

<400> SEQUENCE: 119

```
      tgctccatct aatgatggtg ccgccggcct cgtcccagag atcaacaatg aggcaatggc     60
gctagaccca gtggcgggtg cagcgatagc agcacccctc actggtcagc aaaacataat    120

tgatccctgg attatgaata attttgtgca agcacctggt ggtgagttta cagtgtcccc    180

taggaattcc cctggtgaag tgcttcttaa tttggaattg ggcccagaaa taaaccctta    240

tttggcccat cttgctagaa tgtataatgg ttatgcaggt ggatttgaag tgcaggtggt    300

cctggctggg aatgcgttca cagcaggaaa gataatcttt gca                      343
```

<210> SEQ ID NO 120
<211> LENGTH: 343
<212> TYPE: DNA
<213> ORGANISM: Norwalk-like Virus (GII)

<400> SEQUENCE: 120

```
agctccatcg aatgatggcg cggctggcct cgtaccagag atcaaccatg aggtcatggc     60

catagaacct gttgcagggg cctctttagc agcccctgtc gtaggacaac ttaatataat    120

tgatccctgg attagaaata attttgtgca agcccctgct ggagaattta ctgtttcacc    180

tagaaatgct ccaggtgaat ttctgttaga tctagagtta ggccctgaat tgaacccccta    240

ccttgctcac cttgcacgca tgtataatgg gcatgcaggt ggtatggagg tgcagatagt    300

gcttgctggg aatgcgttca cagcgggcaa aatcctgttt gca                      343
```

<210> SEQ ID NO 121
<211> LENGTH: 32
<212> TYPE: DNA
<213> ORGANISM: Artificial Sequence
<220> FEATURE:
<223> OTHER INFORMATION: probe

<400> SEQUENCE: 121

```
ccgtcgtggg agggcgatcg caatctcgac gg                                   32
```

-continued

```
<210> SEQ ID NO 122
<211> LENGTH: 32
<212> TYPE: DNA
<213> ORGANISM: Artificial Sequence
<220> FEATURE:
<223> OTHER INFORMATION: probe

<400> SEQUENCE: 122

ccgtcgagat tgcgatcgcc ctcccacgac gg                                 32


<210> SEQ ID NO 123
<211> LENGTH: 30
<212> TYPE: DNA
<213> ORGANISM: Artificial Sequence
<220> FEATURE:
<223> OTHER INFORMATION: probe

<400> SEQUENCE: 123

ccgtcgattg cgatcgccct cccacgacgg                                    30


<210> SEQ ID NO 124
<211> LENGTH: 29
<212> TYPE: DNA
<213> ORGANISM: Artificial Sequence
<220> FEATURE:
<223> OTHER INFORMATION: probe

<400> SEQUENCE: 124

cgtggaattg cgatcgccct ccctccacg                                     29


<210> SEQ ID NO 125
<211> LENGTH: 28
<212> TYPE: DNA
<213> ORGANISM: Artificial Sequence
<220> FEATURE:
<223> OTHER INFORMATION: probe

<400> SEQUENCE: 125

cctgcattgc gatcgccctc ccagcagg                                      28
```